US009833509B2

(12) United States Patent
Vissman et al.

(10) Patent No.: US 9,833,509 B2
(45) Date of Patent: Dec. 5, 2017

(54) BIOCERAMIC COMPOSITIONS AND BIOMODULATORY USES THEREOF

(71) Applicant: Multiple Energy Technologies LLC, Washington, PA (US)

(72) Inventors: Shannon Vissman, Upper St. Clair, PA (US); Francisco Jose Cidral-Filho, Washington, PA (US); Francisco de Paula Moreira, Florianópolis (BR); Steven Midttun, Boca Raton, FL (US)

(73) Assignee: MULTIPLE ENERGY TECHNOLOGIES LLC, Washington, PA (US)

( * ) Notice: Subject to any disclaimer, the term of this patent is extended or adjusted under 35 U.S.C. 154(b) by 0 days.

(21) Appl. No.: 14/702,467

(22) Filed: May 1, 2015

(65) Prior Publication Data

US 2015/0335742 A1 Nov. 26, 2015

Related U.S. Application Data

(60) Provisional application No. 62/115,567, filed on Feb. 12, 2015, provisional application No. 62/064,939, (Continued)

(51) Int. Cl.
*B32B 1/02* (2006.01)
*A61K 41/00* (2006.01)
(Continued)

(52) U.S. Cl.
CPC .......... *A61K 41/0052* (2013.01); *A61K 33/00* (2013.01); *A61K 33/08* (2013.01);
(Continued)

(58) Field of Classification Search
CPC ....... B32B 1/02; Y10T 428/1352; A41B 1/00; A61K 33/00; A61K 33/08; C04B 33/04; A61N 5/0613; A61M 21/02
See application file for complete search history.

(56) References Cited

U.S. PATENT DOCUMENTS 2,929,414 A 3/1960 Lienhard
3,969,551 A 7/1976 Ellsworth
(Continued)

FOREIGN PATENT DOCUMENTS

BR PI0801804 A2 2/2009
BR 10805782 A2 8/2010
(Continued)

OTHER PUBLICATIONS

Australian Patent Application No. 2013323956 Examiner's Report No. 3 dated Jan. 22, 2016.
(Continued)

*Primary Examiner* — Marc A Patterson
(74) *Attorney, Agent, or Firm* — Wilson Sonsini Goodrich & Rosati

(57) ABSTRACT

The subject matter described herein is directed to articles, compositions, systems, and methods of using and preparing bioceramic compositions and to the bioceramic compositions. A bioceramic composition of the disclosure radiates infrared energy or rays and can be used in the treatment of various conditions.

15 Claims, 51 Drawing Sheets

Related U.S. Application Data filed on Oct. 16, 2014, provisional application No. 62/062,686, filed on Oct. 10, 2014, provisional application No. 62/018,085, filed on Jun. 27, 2014, provisional application No. 61/988,837, filed on May 5, 2014.

(51) Int. Cl.

| | |
|---|---|
| *C04B 33/04* | (2006.01) |
| *A61N 5/06* | (2006.01) |
| *A61M 21/02* | (2006.01) |
| *D06M 11/36* | (2006.01) |
| *D06M 11/45* | (2006.01) |
| *D06M 11/46* | (2006.01) |
| *D06M 11/79* | (2006.01) |
| *A61K 33/00* | (2006.01) |
| *A61K 33/08* | (2006.01) |
| *A61K 33/22* | (2006.01) |
| *A61K 33/24* | (2006.01) |
| *B32B 1/08* | (2006.01) |
| *A41B 1/00* | (2006.01) |
| *A61M 21/00* | (2006.01) |
| *A61F 7/00* | (2006.01) |
| *D06M 15/643* | (2006.01) |

(52) U.S. Cl.
CPC .............. *A61K 33/22* (2013.01); *A61K 33/24* (2013.01); *A61M 21/02* (2013.01); *A61N 5/0613* (2013.01); *A61N 5/0616* (2013.01); *A61N 5/0625* (2013.01); *C04B 33/04* (2013.01); *D06M 11/36* (2013.01); *D06M 11/45* (2013.01); *D06M 11/46* (2013.01); *D06M 11/79* (2013.01); *A61F 2007/0088* (2013.01); *A61M 2021/0016* (2013.01); *A61N 2005/066* (2013.01); *A61N 2005/0643* (2013.01); *A61N 2005/0645* (2013.01); *A61N 2005/0656* (2013.01); *A61N 2005/0659* (2013.01); *C04B 2235/9607* (2013.01); *D06M 15/643* (2013.01)

(56) References Cited

U.S. PATENT DOCUMENTS

| | | | |
|---|---|---|---|
| 4,175,556 A | | 11/1979 | Freezer |
| 4,344,908 A | * | 8/1982 | Smith .................... B29C 70/10 264/203 |
| 4,680,822 A | | 7/1987 | Fujino et al. |
| 4,968,531 A | * | 11/1990 | Maeda .................... A61F 7/02 427/160 |
| 5,208,089 A | | 5/1993 | Norris |
| 5,258,228 A | | 11/1993 | Komuro |
| 5,296,531 A | | 3/1994 | Belde et al. |
| 5,299,335 A | | 4/1994 | Ivester et al. |
| 5,645,934 A | | 7/1997 | Marcolongo et al. |
| 5,820,348 A | * | 10/1998 | Fricke .................... F01D 5/027 188/268 |
| D405,885 S | | 2/1999 | Pinter |
| 5,894,067 A | | 4/1999 | Kim |
| 5,935,550 A | | 8/1999 | Mohri et al. |
| 5,972,215 A | | 10/1999 | Kammel |
| 5,972,815 A | | 10/1999 | Bae |
| 6,074,754 A | | 6/2000 | Jacobsen et al. |
| 6,207,077 B1 | | 3/2001 | Burnell-Jones |
| 6,207,600 B1 | | 3/2001 | Nakajima et al. |
| 6,264,907 B1 | | 7/2001 | Matsuda et al. |
| 6,506,403 B1 | | 1/2003 | Yu |
| 6,516,229 B1 | | 2/2003 | Wey |
| 6,645,517 B2 | | 11/2003 | West et al. |
| 6,651,256 B1 | * | 11/2003 | Swift .................... A42B 1/004 2/15 |
| 6,669,882 B2 | | 12/2003 | Seok |
| 6,797,377 B1 | | 9/2004 | Delucia et al. |
| 6,884,256 B2 | | 4/2005 | Huang et al. |
| 6,951,900 B2 | | 10/2005 | Blanchard et al. |
| 7,056,845 B2 | | 6/2006 | Waeber et al. |
| 7,063,801 B2 | | 6/2006 | Sato |
| 7,074,499 B2 | | 7/2006 | Schnurer et al. |
| 7,311,209 B2 | | 12/2007 | Bentz et al. |
| D598,660 S | | 8/2009 | Schaller |
| 7,824,350 B2 | | 11/2010 | Lu |
| D629,210 S | | 12/2010 | Hong |
| D631,971 S | | 2/2011 | Turtzo et al. |
| 8,104,482 B2 | | 1/2012 | Komuro |
| 8,231,968 B2 | | 7/2012 | Lin et al. |
| D664,739 S | | 8/2012 | Gibson |
| D667,226 S | | 9/2012 | Levy |
| 8,333,018 B2 | | 12/2012 | Lin et al. |
| 8,366,757 B2 | | 2/2013 | Oliveira et al. |
| 8,388,750 B2 | | 3/2013 | Gay et al. |
| 8,409,262 B2 | | 4/2013 | Lin et al. |
| 8,491,825 B2 | | 7/2013 | Lin et al. |
| D704,455 S | | 5/2014 | Blakely et al. |
| 8,815,158 B2 | | 8/2014 | Zheng et al. |
| 8,968,819 B2 | | 3/2015 | Hirata |
| 8,980,775 B2 | | 3/2015 | Francy et al. |
| 9,044,384 B2 | | 6/2015 | Canova et al. |
| 9,120,959 B2 | | 9/2015 | Hara et al. |
| D746,543 S | | 1/2016 | McClain |
| 9,376,576 B2 | | 6/2016 | Jung et al. |
| 2002/0014716 A1 | * | 2/2002 | Seok .................... C08K 3/34 264/140 |
| 2002/0042641 A1 | | 4/2002 | Johnson et al. |
| 2002/0195751 A1 | | 12/2002 | Kim et al. |
| 2004/0043174 A1 | | 3/2004 | Schnurer et al. |
| 2004/0087430 A1 | | 5/2004 | Sola |
| 2004/0202899 A1 | | 10/2004 | Komuro |
| 2004/0225049 A1 | | 11/2004 | Komuro |
| 2005/0060807 A1 | * | 3/2005 | Kaizuka .................... A47G 9/007 5/636 |
| 2005/0066448 A1 | | 3/2005 | Waeber et al. |
| 2005/0171584 A1 | | 8/2005 | Slingo |
| 2005/0227047 A1 | | 10/2005 | Sutter et al. |
| 2005/0241069 A1 | | 11/2005 | Lin |
| 2006/0137701 A1 | | 6/2006 | Snaidr |
| 2006/0275348 A1 | | 12/2006 | Komuro |
| 2007/0116775 A1 | | 5/2007 | Lee |
| 2009/0065732 A1 | | 3/2009 | Yeh et al. |
| 2009/0137171 A1 | | 5/2009 | Waeber et al. |
| 2009/0171266 A1 | | 7/2009 | Harris |
| 2009/0267271 A1 | | 10/2009 | Kim |
| 2010/0186917 A1 | | 7/2010 | Simonson et al. |
| 2010/0282433 A1 | | 11/2010 | Blackford |
| 2011/0021098 A1 | | 1/2011 | Tabellion et al. |
| 2011/0027548 A1 | | 2/2011 | Nusser et al. |
| 2011/0059037 A1 | | 3/2011 | Canova et al. |
| 2011/0112461 A1 | | 5/2011 | Hirata |
| 2011/0208099 A1 | | 8/2011 | Naghavi et al. |
| 2012/0060344 A1 | | 3/2012 | Smeets |
| 2012/0135485 A1 | | 5/2012 | Koros et al. |
| 2014/0079920 A1 | | 3/2014 | Blakely |
| 2014/0087040 A1 | | 3/2014 | Vissman et al. |
| 2014/0173801 A1 | | 6/2014 | Bell |
| 2014/0187413 A1 | | 7/2014 | Lagaron Cabello et al. |
| 2014/0197562 A1 | * | 7/2014 | Piccinini .................... C08J 9/0061 264/54 |
| 2014/0209594 A1 | | 7/2014 | Besner |
| 2014/0255664 A1 | | 9/2014 | Gartmann et al. |
| 2014/0264186 A1 | | 9/2014 | Spatz et al. |
| 2014/0324132 A1 | | 10/2014 | Wey |
| 2015/0017856 A1 | | 1/2015 | Davis et al. |
| 2015/0224230 A1 | | 8/2015 | Hirata |
| 2015/0291868 A1 | | 10/2015 | Rajagopalan et al. |
| 2015/0335742 A1 | | 11/2015 | Vissman et al. |
| 2016/0136386 A1 | | 5/2016 | Vissman et al. |
| 2016/0136452 A1 | | 5/2016 | Vissman et al. |
| 2016/0143838 A1 | | 5/2016 | Canova et al. |

(56) References Cited

U.S. PATENT DOCUMENTS

| | | | |
|---|---|---|---|
| 2016/0151300 | A1 | 6/2016 | Madvin |
| 2017/0049890 | A1 | 2/2017 | Vissman et al. |

FOREIGN PATENT DOCUMENTS

| | | | |
|---|---|---|---|
| BR | MU9000125 | U2 | 9/2011 |
| BR | MU9001019 | U2 | 1/2012 |
| CN | 1887784 | A | 1/2007 |
| CN | 102553623 | A | 7/2012 |
| EP | 1816254 | A1 | 8/2007 |
| EP | 2900621 | A1 | 8/2015 |
| EP | 3140004 | A1 | 3/2017 |
| GB | 883264 | A | 11/1961 |
| GB | 1093041 | A | 11/1967 |
| GB | 1378140 | A | 12/1974 |
| GB | 2073613 | A | 10/1981 |
| GB | 2463264 | A | 3/2010 |
| JP | 07331501. | | 12/1995 |
| JP | 2000119987 | A | 4/2000 |
| JP | 2008308353 | A | 12/2008 |
| JP | 09225045 | A. | 1/2010 |
| KR | 20050046213 | A | 5/2005 |
| KR | 200500461213 | | 5/2005 |
| KR | 100783486 | B1 * | 12/2007 |
| KR | 20100009129 | A | 1/2010 |
| KR | 101067409 | B1 | 9/2011 |
| WO | WO-02059414 | A2 | 8/2002 |
| WO | WO-2006007753 | A1 | 1/2006 |
| WO | WO-2009118419 | A1 | 10/2009 |
| WO | WO-2009124367 | A2 | 10/2009 |
| WO | WO-2013053587 | A1 | 4/2013 |
| WO | WO-2013182568 | A2 | 12/2013 |
| WO | WO-2013182568 | A3 | 1/2014 |
| WO | WO-2015171467 | A1 | 11/2015 |

OTHER PUBLICATIONS

Chinese Patent Application No. 201380049767.7 Office Action dated Jan. 22, 2016.
Eurasia Patent Application No. 201590577 Office Action Jan. 18, 2016.
U.S. Appl. No. 14/965,741 First Action Interview dated Apr. 18, 2016.
U.S. Appl. No. 14/965,746 Office Action dated Mar. 24, 2016.
U.S. Appl. No. 29/495,157 Ex Parte Quayle Office Action dated May 9, 2016.
U.S. Appl. No. 29/495,157 Restriction Requirement dated Feb. 11, 2016.
Australia Patent Application No. 2013323956 Notice of Acceptance dated Apr. 13, 2016.
Colombia Patent Application No. NC2016/0003955 Office Action dated Oct. 20, 2016.
U.S. Appl. No. 14/965,741 Office Action dated Feb. 9, 2017.
Australian Patent Application No. 2013323956 Patent Examination Report No. 2 dated Nov. 6, 2015.
Lai et al., Effects of far-infrared irradiation on myofascial neck pain: A randomized, double-bind, placebo-controlled pilot study. The Journal of Alternative and Complementary Medicine, 0(0):1-7 (2013).
Leung et al., Physiological effects of bioceramic material: Harvard step, resting metabolic rate and treadmill running assessments. Chinese Journal of Physiology, 56(x):1-7 (2013).
Tuduvz, LLC, Far Infrared therapy: Healing with far infrared therapy. Website (online), Apr. 13, 2014 (retrieved on Aug. 11, 2015), www.endtimeessentials.com/far-infrared-therapy.
U.S. Appl. No. 13/760,546 Office Action dated Sep. 23, 2015.
Chinese Patent Application No. 201380049767.7 Office Action dated Sep. 20, 2016.
Colombia Patent Application No. 15-090.148 Official Action dated Jun. 17, 2016.
Columbia Patent Application No. 15-090.148 Official Action dated Nov. 11, 2016.
Eurasian Patent Application No. 201590577 Office Action dated Aug. 30, 2016.
Japanese Patent Application No. 11335966-A dated May 1998 to Kusakari et al.
Korean Patent Application No. 1020100009129-A dated Jan. 2010 to Kim.
PCT/US2015/028910 International Preliminary Report on Patentability dated Nov. 17, 2016.
U.S. Appl. No. 13/760,546 Office Action dated Dec. 13, 2016.
U.S. Appl. No. 13/760,546 Office Action dated Jun. 17, 2016.
U.S. Appl. No. 14/965,741 First Action Interview Office Action Summary dated Sep. 14, 2016.
U.S. Appl. No. 14/965,746 Office Action dated Aug. 25, 2016.
Emer et al., University of Southern Santa Catarina, Laboratory of Experimental Neuroscience Far Infrared Emitted by Bioceramics Reduced Hypernociception of Inflammatory Origin in Mice Study presented at the 45th Congress of Pharmacology and Experimental Therapeutics, Ribeirao Preto, SP, Brazil, 2013, 4 pages, 2014.
U.S. Appl. No. 13/760,546 Office Action dated Jun. 15, 2017.
U.S. Appl. No. 14/965,741 Office Action dated Jul. 3, 2017.
Eurasian Patent Application No. 201590577 Office Action dated Apr. 4, 2017.
U.S. Appl. No. 14/965,746 Office Action dated Mar. 23, 2017.
Agathocleous et al. Preliminary Results of a Phase I/II Study of Weekly or Twice Weekly Bortezomib in Combination with Rituximab, in Patients with Follicular Lymphoma, Mantle Cell Lymphoma and Waldenstrom's Macroglobulinaemia. Blood (ASH Annual Meeting Abstracts) 110:Abstract 2559 (2007).
Australian Patent Application No. 2013323956 Examination Report dated May 29, 2015.
Cidral-Filho et al. Effect of Far Infrared Emitted by Bioceramics on Clinical Measures of Physical Fitness, May 7, 2014, vol. 20, Issue No. 5, A71.
Cidral-Filho et al. Far Infrared Emitted by Ceramic Materials Increases Paw Temperature and Reduces Mechanical Hypersensitivity and Knee Edema in a Rat Model of Monoiodoacetate-Induced Osteoarthritis, Jul. 28-30, 2014, vol. 3, Issue No. 2.
Cidral-Filho et al. Neurobiological Mechanisms and Perspectives on Far-Infrared Emitting Ceramic Materials for Pain Relief, 2014, vol. 4, Issue No. 2, 1000159.
Emeraline, et al. Effect of Far Infrared Emitted by Bioceramics on Parameters of Physical Performance in Mice, May 7, 2014, vol. 20, Issue No. 5, A34-A34.
Emeraline, et al. Far Infrared Emitted by Bioceramics Reduces Mechanical and Thermal Hyperalgesia in an Animal Model of Chronic Inflammatory Pain, May 7, 2014, vol. 20, Issue No. 5.
Emeraline, et al. Far Infrared Therapy Emitted by Bioceramics Improves Pstural Sway in Young Brazilian University Judokas, May 7, 2014, vol. 20, Issue No. 5, A73-A73.
EP Application No. 13842936.0 Extended European Search Report dated Jul. 17, 2015.
European Patent Application No. 13842936 Extended European Search Report dated Jul. 17, 2015.
Far Infrared Emitted by Bioceramics Reduced Hypernociception of Inflammatory Origin in Mice Study by University of Southern Santa Catarina Laboratory of Experimental Neuroscience. Feb. 2014.
Lai, et al. Effects of Far-Infrared Irradiation on Myofascial Neck Pain: a Randomized, Double-Blind, Placebo-Controlled Pilot Study, Feb. 2014, vol. 20, Issue No. 2, 123-129.
Leung, et al. Physiological Effects of Bioceramic Material: Harvard Step, Resting Metabolic Rate and Treadmill Running Assessments, Dec. 21, 2013, vol. 56, Issue No. 6, 1-7.
Martins, et al. Far-Infrared Emitting Ceramic Meterial-Impregnated Fabrics Reduces Pain and Improves Quality of Life in Patients with Fibromyalgia: Double-Blinded Randomized Placebo Controlled Trial, Mar. 13, 2015, Abstract ID 1007.
Martins, et al. Neuromodulation by Far-Infrared Emitting Ceramic Material in an Animal Model of Persistent Inflammatory Pain, Mar. 13, 2015, Abstract.
PCT/US2015/028910 International Search Report and Written Opinion Dated Sep. 1, 2015.

(56) References Cited

OTHER PUBLICATIONS

Tuduvz LLC Far Infrared Therapy. Healing with Far Infrared Therapy. Website. (Accessed Sep. 11, 2015).
XP-002740908 Manufacturing method and its material of painting medium having bio-ceramics, KR 2005 0046213 A, May 18, 2005.
XP002740909, Method for preparing porous tourmaline slab with photocatalytic performance, CN 102 553 623 A, Jul. 11, 2012.
XP002740910, Porcelain tile and its manufacturing method. JP 2008 308353, Dec. 25, 2008.
Aksenov, M.Y.; Markesbery, W.R. "Changes in thiol content and expression of glutathione redox system genes in the hippocampus and cerebellum in Alzheimer disease." NeurosciLett, v. 302, p. 141-145, 2001.
Bagnato et al., "Far infrared emitting plaster in knee osteoarthritis: a single blinded, randomised clinical trial", Reumatismo, 64 (6): 388-394, 2012.
Bannister, J.V.; Calabrese, L. Assays for superoxide dismutase. Methods Biochem Anal, v. 32, p. 279-312, 1987.
Beever, "Far-infrared saunas for treatment of cardiovascular risk factors" Canadian Family Physician, vol. 55:691-696, Jul. 2009.
Cidral-Filho, F. and D. Martins. "Neurobiological Mechanisms and Perspectives on Far-Infrared Emitting Ceramic Materials for Pain Relief" J Yoga Phys Ther 4 (2):159, 2014.
Colombia Patent Application No. 15-090.148 Official Action dated May 17, 2015.
Conrado et al., "Reduction in body measurements after use of a garment made with synthetic fibers embedded with ceramic nanoparticles", Journal of Cosmetic Dermatology, 10, 1, 30-35, 2011.
eSilva et al., "Effects of the Use of MIG3 Bioceramics Fabrics Use—Long Infrared Emitter—in Pain, Intolerance to Cold and Periodic Limb Movements in Post-Polio Syndrome", Arq Neuropsiquiatr 2009; 67(4): 1049-1053.
Esterbauer, H., Cheeseman, K.H. "Determination of aldehydic lipid peroxidation products: malonaldehyde and 4-hydroxynonenal." Methods Enzymol, v. 186, p. 407-421, 1990).
Gale et al., "Infrared therapy for chronic low back pain: A randomized, controlled trial", Pain Res Manage, vol. 11, No. 3, p. 193-197, Autumn 2006.
Hong, R. "Effects of Heat Therapy using a far infrared rays heating element for dysmenorrhea in high school girls". J Korean Acad. Nurs vol. 41 No. 1, 141-148, 2011.
Hsieh et al., Local and Systemic Cardiovascular Effects from Monochromatic Infrared Therapy in Patients with Knee Osteoarthritis: A Double-Blind, Randomized, Placebo-Controlled Study, Evidence-Based Complementary and Alternative Medicine, vol. 2012, Article ID 583016, 9 pages.
Ke Y. et al. "Effects of Somatothermal Far-Infrared Ray on Primary Dysmenorrhea: A Pilot Study". Evidence-Based Complementary and Alternative Medicine, vol. 2012, Article ID 240314, doi: 10.1155/2012/240314, 8 pages.
Kim et al., "Bioceramic Effects to Enhance Secondary Metabolites Production in Tissue Culture of Some Medicinal Plants", Korean J. Medicinal Crop Sci. 12(2) : 118-122 (2004).
Ko et al., Effect of Ceramic-Impregnated "Thermoflow" Gloves on Patients with Raynaud's Syndrome: Randomized, Placebo-Controlled Study, Alternative Medicine Review, Aug. 2002; vol. 7(4), pp. 328-335.
Koo et al. The application of PCMMcs and Sic by commercially direct dual-complex coating on textile polymer. Applied Surface Science 255:8313-8318. 2009.
Leung et al., "Biological effects of melt spinning fabrics composed of 1% bioceramic material", Textile Research Journal, 82(11) 1121-1130, downloaded from trj.sagepub.com Mar. 11, 2013.
Leung et al., "Bone and Joint Protection Ability of Ceramic Material with Biological Effects", Chinese Journal of Physiology 55(1): 47-54, 2012.
Leung et al., "Direct and Indirect Effects of Ceramic Far Infrared Radiation on the Hydrogen Peroxide-scavenging Capacity and on Murine Macrophages under Oxidative Stress", Journal of Medical and Biological Engineering, 31(5): 345-351, 2010.
Leung et al., Effects of Far Infrared Rays Irradiated from Ceramic Material (BIOCERAMIC) on Psychological Stress-Conditioned Elevated Heart Rate, Blood Pressure, and Oxidative Stress-Suppressed Cardiac Contractility, Chinese Journal of Physiology 55(5): 323-330, 2012.
Leung et al., "In vitro cell study of the Possible Anti-inflammatory and Pain Relief Mechanism of Far-infrared Ray-emitting Ceramic Material", J. Med. and Biol. Eng. 33(2): 179-184.
Leung et al., "Protective effect of non-ionized radiation from far infrared ray emitting ceramic material (cFIR) against oxidative stress on human breast epithelial cells", Articles in Press, J. Med. Biol. Eng. (Jul. 28, 2012), doi: 10.5405/jmbe.1133, 25 pages.
Leung T. et al. Physical-chemical Test Platform for Room Temperature, Far-infrared Ray Emitting Ceramic Materials (cFIR). Published online on Oct. 12, 2011; doi: 10.1002/jccs.201190101, J. of the Chinese Chemical Society, 58:653-658, 2011.
Levine, et al., "Determination of carbonyl content in oxidatively modified proteins." Methods Enzymol, v. 186, p. 464-478, 1990.
Liau et al., "Inhibitory Effects of Far-Infrared Ray-Emitting Belts on Primary Dysmenorrhea", International Journal of Photoenergy, vol. 2012, Art. ID 238468, 7 pages.
Lin et al., "Antioxidant Effect of Far-Infrared Radiation in Human" Journal of Public Health Frontier. Jun. 2013, vol. 2 Iss. 2, pp. 97-102.
Lin et al. Enhancement of Transdermal Delivery of Indomethacin and tamoxifen by Far-Infrared Ray-Emitting Ceramic material (BIOCERAMIC): A Pilot Study. Translational Medicine 2013, 3:1, 5 pages.
Lowry, O.H.; Rosebrough, N.J.; Farr, A. "Protein measurement with the Folin phenol reagent." J BiolChem, v. 193, p. 265-275, 1951.
PCT/US2013/060636 International Preliminary Report on Patentability dated Apr. 9, 2015.
PCT/US2013/060636 International Search Report and Written opinion dated Dec. 10, 2013.
U.S. Appl. No. 13/760,546 Office Action dated Apr. 9, 2015.
Vatansever F. and Hamblin M. Far infrared radiation (FIR): its biological effects and medical applications. Photon Lasers Med 2012; 1(4): 255-266.
"Complementary, Alternative, or Integrative Health: What's In a Name?" (Created Oct. 2008, Updated Mar. 2015), Retrieved Jul. 2015 from http://nccam.nih.gov/health/whatiscam, 5 pages.
Yoo et al., "Investigation of jewelry powders radiating far-infrared rays and the biological effects on human skin", J. Cosmet Sci., 53:175-184, (May/Jun. 2002).
York R. and Gordon I., Effect of optically modified polyethylene terephthalate fiber socks on chronic foot pain. BMC Complementary and Alternative Medicine 2009, 9:10, 7 pages.
U.S. Appl. No. 14/965,746 Office Action dated Aug. 10, 2017.
Leung et al., "In vitro cell study of the Possible Anti-inflammatory and Pain Relief Mechanism of Far-infrared Ray-emitting Ceramic Material ", J. Med. and Biol. Eng. 33(2): 179-184.
Liau et al., "Inhibitory Effects of Far- Infrared Ray-Emitting Belts on Primary Dysmenorrhea", International Journal of Photoenergy, vol. 2012, Art. ID 238468, 7 pages.

* cited by examiner

PANEL A

PANEL B

BIOCERAMIC COMPOSITIONS AND BIOMODULATORY USES THEREOF

CROSS REFERENCE

This application claims the benefit of U.S. Provisional Application No. 62/115,567, filed on Feb. 12, 2015; U.S. Provisional Application No. 62/064,939, filed on Oct. 16, 2014, U.S. Provisional Application No. 62/062,686; filed on Oct. 10, 2014, U.S. Provisional Application No. 62/018,085, filed on Jun. 27, 2014; U.S. Provisional Application No. 61/988,837, filed on May 5, 2014; the contents of each of which of which are incorporated by reference herein in their entireties.

BACKGROUND OF THE INVENTION

Infrared wavelength ranges from 0.7 to 1000 microns and is just beyond visible light on the electromagnetic spectrum. Infrared has strong physical properties and great thermal activity.

SUMMARY OF THE INVENTION

The natural resonant frequency range of water and living organisms, including man, falls within the infrared range. For example, the wavelength range of 6-18 micrometers is beneficial to the human body by virtue of its activating and energizing effect on the body. Indeed, human skin radiates 9.36 micrometer infrared wave which is very close to the resonant frequency of a water molecule—and rightly so since our bodies are about 70% water. Infrared waves are considered a safe and beneficial energy source for humans. The instant inventors have identified beneficial properties of the inventive bioceramic compositions and applications as described herein.

As described herein, bioceramics include ceramics which radiate beneficial infrared waves to living organisms. The subject matter described herein utilizes the beneficial effects of the infrared radiation. The methods, articles, systems, and compositions of matter described herein employ a unique formulation of bioceramic materials, which are ultra-fine mineral particles, that when heated by a living organism, such as the human body, emit far-infrared energy. The bioceramic materials described herein are refractory polycrystalline compounds that due to their inertness in aqueous conditions are highly biocompatible and safe for human interaction and application. The inventors have invented numerous biomodulatory or physiological applications of these bioceramic formulations, including but not limited to the regulation of cell metabolism, the induction of analgesia, muscle relaxation and modulation of inflammation and oxidative stress.

According to the laws of thermodynamics, any two bodies in contact reach thermal equilibrium through a direct microscopic exchange of kinetic energy in the form of electromagnetic radiation generated by the thermal motion of the charged particles in matter. Thus, when the bioceramic materials, articles, and compositions described herein and the human body are in contact, there is an exchange of thermal radiation, more specifically far infrared radiation. Because of the specific properties of the minerals and oxides contained in the subject matter described herein, i.e., highly refractory minerals, this emission is intensified in the spectrum of far infrared which has numerous biomodulatory or physiological effects. The inventors of the instant application have unexpectedly discovered numerous advantages of using the bioceramic materials described herein to complement or serve as the basis of a therapeutic approach for living organisms.

The subject matter described herein provides a non-invasive, safe, convenient, and effective methodology to deliver the positive effects of far-infrared therapy to a subject. For example, in some embodiments, a patient carries, wears and/or uses the bioceramic compositions, for example when applied to an article of manufacture such as a shirt, at home and/or in the course of carrying out daily activities to help extend the benefits of the treatment the patient may receive at a clinic or to improve a patient's condition during or after physical exercise.

A feature of the subject matter described herein, including the articles, compositions of matter, methods, devices, and systems, is a composition that comprises a bioceramic, provided that when heated or exposed to heat, such as the warmth of the human body, the bioceramic provides a biomodulatory physiological effect when the article is applied to a subject. In some embodiments, the article is an apparel of clothing such as a shirt.

Another feature of the subject matter described herein is a bioceramic composition of matter. For example, in one embodiment, the composition comprises (a) about 20 wt % to about 80 wt % kaolinite ($Al_2Si_2O_5(OH)_4$); (b) about 1 wt % to about 30 wt % tourmaline; (c) about 1 wt % to about 40 wt % aluminum oxide ($Al_2O_3$); (d) about 1 wt % to about 40 wt % silicon dioxide ($SiO_2$); and (e) about 1 wt % to about 20 wt % zirconium oxide ($ZrO_2$); provided that the amounts are by total weight of the bioceramic composition. In another embodiment, the composition comprises: (a) about 40 wt % to about 60 wt % kaolinite ($Al_2Si_2O_5(OH)_4$); (b) about 5 wt % to about 15 wt % tourmaline; (c) about 15 wt % to about 25 wt % aluminum oxide ($Al_2O_3$); (d) about 10 wt % to about 20 wt % silicon dioxide ($SiO_2$); and (e) about 1 wt % to about 20 wt % zirconium oxide ($ZrO_2$); provided that the amounts are by total weight of the bioceramic composition. In yet another embodiment, provided is a bioceramic composition comprising: (a) about 50 wt % kaolinite ($Al_2Si_2O_5(OH)_4$); (b) about 10 wt % tourmaline; (c) about 18 wt % aluminum oxide ($Al_2O_3$); (d) about 14 wt % silicon dioxide ($SiO_2$); and (e) about 8 wt % zirconium oxide ($ZrO_2$); provided that the amounts are by total weight of the bioceramic composition. In certain of these embodiments, the compositions of matter comprise tourmaline and the tourmaline comprises $NaFe^{2+}_3Al_6Si_6O_{18}(BO_3)_3(OH)_3OH$.

An additional feature of the subject matter described herein is the provision of a biomodulatory or physiological effect that comprises: a modulation of pain, an increase in muscle endurance, a modulation of the cardiorespiratory system, a modulation of cellular metabolism, analgesia, an anti-oxidative effect, an anti-fibromyalgia effect, a decrease in inflammation, a decrease in oxidative stress, a modulation of cytokine levels, a modulation of blood circulation, a reduction in intolerance to a cold environment, a reduction in a symptom of arthritis or vascular disease, an increase in cutaneous perfusion, a decrease in heart rate, a decrease in blood pressure, an esthetic effect such as a reduction of body measurements), reduction of weight, or a reduction in cellulite of the subject.

Yet another feature of the subject matter described herein is a non-invasive method of providing a biomodulatory or physiological effect in or to a subject comprising contacting an article comprising a bioceramic to the skin of the subject, provided that when heated or exposed to heat, the bioceramic composition provides far infrared thermal radiation and a biomodulatory or physiological effect to the subject in a non-invasive manner.

Another feature of the subject matter described herein is a method for preparing an article comprising the steps of: (a) preparing a bioceramic solution; and (b) applying the solution to the article; provided that the solution, when applied to the article, comprises about 20 wt % to about 80 wt % kaolinite ($Al_2Si_2O_5(OH)_4$); about 1 wt % to about 30 wt % tourmaline; about 1 wt % to about 40 wt % aluminum oxide ($Al_2O_3$); about 1 wt % to about 40 wt % silicon dioxide ($SiO_2$); and from about 1 wt % to about 20 wt % zirconium oxide ($ZrO_2$) further provided that the amounts are by total weight of the bioceramic composition.

An additional feature of the subject matter described herein is a method for preparing an article comprising the steps of: (a) preparing a bioceramic solution; and (b) applying the solution on the article; provided that when heated or exposed to heat, the bioceramic provides a biomodulatory or physiological effect when the article is applied to a subject.

BRIEF DESCRIPTION OF THE DRAWINGS

The novel and inventive features of the invention are set forth with particularity in the appended claims. A better understanding of the features and advantages of the present invention will be obtained by reference to the following detailed description that sets forth illustrative embodiments, in which the principles of the invention are utilized, and the accompanying drawings which in this provisional patent application are provided in the Examples section below.

FIG. 25A and FIG. 25 B illustrate a non-limiting example of the infrared transmittance of distinct bioceramic compositions of the instant disclosure. FIG. 25A illustrates the infrared transmittance of bioceramic compositions described herein comprising 18% aluminum oxide, 14% silicon dioxide, 50% kaolinite, 8% zirconium oxide, and 10% tourmaline.

DETAILED DESCRIPTION OF THE INVENTION

Figure 1:
FIG. 1 illustrates a non-limiting example of a shirt comprising a bioceramic of the instant disclosure

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

Without being limited by theory the instant inventors have discovered that the biological effects of bioceramics are based on the fact that the infrared frequency range is the natural resonant frequency range of water and living organisms. Because a considerable part of living organisms include water, the resonant frequency of water molecules radiated from the bioceramics described herein can activate the water and affect living organisms, including humans, and including the treatment of disease and biological complications and pathways.

The bioceramics of the disclosure radiate far infrared energy towards the body or away from the body of a subject. When a bioceramic radiates energy towards the body of a subject, the bioceramic provides concentrated radiant energy to cells by reflecting the far infrared energy or rays of the body heat into the subject's joints, muscles, and tissues. The far infrared energy penetrates the cells and provides biomodulatory or physiological effects, such as anti-inflammatory, analgesic, and other biomodulatory or physiological effects. When a bioceramic radiates energy away from the body of a subject, the bioceramic prevents far infrared energy from penetrating the skin of a subject, thereby providing a cooling effect.

Bioceramic Compositions

An aspect of the articles, compositions of matter, methods, devices, and systems described herein is a bioceramic composition that in certain applications provides a biomodulatory or physiological effect. For example, in some embodiments, provided is a bioceramic composition that when heated or exposed to heat provides a biomodulatory or physiological effect when the article is applied to a subject. In one embodiment, the bioceramic comprises:

a. about 20 wt % to about 80 wt % kaolinite ($Al_2Si_2O_5(OH)_4$);
b. about 1 wt % to about 30 wt % tourmaline;
c. about 1 wt % to about 40 wt % aluminum oxide ($Al_2O_3$);
d. about 1 wt % to about 40 wt % silicon dioxide ($SiO_2$); and
e. about 1 wt % to about 20 wt % zirconium oxide ($ZrO_2$); provided that the amounts are by total weight of the bioceramic composition.

In further or additional embodiments, provided is a bioceramic composition of matter that when heated or exposed to heat provides a biomodulatory or physiological effect when the article is applied to a subject, comprising:

a. about 40 wt % to about 60 wt % kaolinite ($Al_2Si_2O_5(OH)_4$);
b. about 5 wt % to about 15 wt % tourmaline;
c. about 15 wt % to about 25 wt % aluminum oxide ($Al_2O_3$);
d. about 10 wt % to about 20 wt % silicon dioxide ($SiO_2$); and
e. about 1 wt % to about 20 wt % zirconium oxide ($ZrO_2$); provided that the amounts are by total weight of the bioceramic composition. In some embodiments, the bioceramic composition comprises kaolinite in a range from about 45 wt % to about 55 wt %. In further or additional embodiments, provided is a bioceramic composition that comprises kaolinite in the range from about 47 wt % to about 53 wt %. In further or additional embodiments, provided is a bioceramic composition that contains kaolinite in a range from about 48 wt % to about 52 wt %.

In some embodiments, provided is a bioceramic composition that comprises
a. about 50 wt % kaolinite ($Al_2Si_2O_5(OH)_4$);
b. about 10 wt % tourmaline;
c. about 18 wt % aluminum oxide ($Al_2O_3$);
d. about 14 wt % silicon dioxide ($SiO_2$); and
e. about 8 wt % zirconium oxide ($ZrO_2$).

Another feature of the subject matter described herein are bioceramic compositions that include tourmaline. As used herein, the term "tourmaline" retains its meaning known in the mineral and gemstone arts. For example, tourmaline, is a group of isomorphous minerals with an identical crystal lattice. Each member of the tourmaline group has its own chemical formula, due to small differences in their elemental distribution. For example, in some embodiments, the tourmaline has the following generic formula $X_1Y_3Al_6(BO_3)_3Si_6O_{18}(OH)_4$, where: X=Na and/or Ca and Y=Mg, Li, Al, and/or $Fe^{2+}$, which is represented with the following formula, $(Na,Ca)(Mg,Li,Al,Fe^{2+})_3Al_6(BO_3)_3Si_6O_{18}(OH)_4$.

In some embodiments, the Al may be replaced by other elements. For example, in Uvite, the Al is partially replaced by Mg which expands the formula to: $(Na,Ca)(Mg,Li,Al,Fe^{2+})_3(Al,Mg,Cr)_6(BO_3)_3Si_6O_{18}(OH)_4$.

In some embodiments, the tourmaline is Buergerite which contains three O atoms and one F atom in place of the OH radical. A Buergerite molecule also contains an Fe atom that is in a 3+ oxidation state which is depicted as: $(Na,Ca)(Mg,Li,Al,Fe^{2+},Fe^{3+})_3(Al,Mg,Cr)_6(BO_3)_3Si_6O_{18}(OH,O,F)_4$. In other embodiments, the tourmaline is one or more of the following:

Schorl: $NaFe^{2+}_3Al_6(BO_3)_3Si_6O_{18}(OH)_4$;
Dravite: $NaMg_3Al_6(BO_3)_3Si_6O_{18}(OH)_4$;
Elbaite: $Na(Li,Al)_3Al_6(BO_3)_3Si_6O_{18}(OH)_4$;
Liddicoatite: $Ca(Li,Al)_3Al_6(BO_3)_3Si_6O_{18}(OH)_4$;
Uvite: $Ca(Mg,Fe^{2+})_3Al_5Mg(BO_3)_3Si_6O_{18}(OH)_4$;
Buergerite: $NaFe^{3+}_3Al_6(BO_3)_3Si_6O_{18}O_3F$.

In one embodiment, the bioceramic composition tourmaline that comprises $NaFe^{2+}_3Al_6Si_6O_{18}(BO_3)_3(OH)_3OH$.

Another aspect of the articles, compositions of matter, methods, devices, and systems described herein is a bioceramic composition of micrometer particle size. For example, in some embodiments, provided is a bioceramic composition containing a largest dimension of any particle in the bioceramic of from about 0.1 micrometer (μm) to about 250 micrometers. In further or additional embodiments, provided is a bioceramic composition, provided that the largest dimension of any particle in the bioceramic is from about 0.5 micrometers to about 25 micrometers. In some cases, a bioceramic particle can have a diameter, or cross-sectional area, of about 0.1 μm to about 1 μm, of about 0.1 μm to about 10 μm, of about 0.1 μm to about 20 μm, of about 0.1 μm to about 30 μm, of about 0.1 μm to about 40 μm, of about 0.1 μm to about 50 μm, of about 0.1 μm to about 60 μm, of about 0.1 μm to about 70 μm, of about 0.1 μm to about 80 μm, of about 0.1 μm to about 90 μm, of about 0.1 μm to about 100 μm, or other desired size. In some cases, an inlet can have a cross-sectional diameter of about 10 μm to about 100 μm, of about 10 μm to about 200 μm, of about 10 μm to about 300 μm, of about 10 μm to about 400 μm, of about 10 μm to about 500 μm, or other desired size.

In further or additional embodiments, provided is a bioceramic composition of matter that when heated or exposed to heat provides a biomodulatory or physiological effect when the article is applied to a subject, wherein the bioceramic composition comprises tourmaline, kaolinite and at least one oxide. In some cases a bioceramic of the disclosure comprises tourmaline, kaolinite, aluminum oxide and silicon dioxide. In some cases a bioceramic of the disclosure comprises tourmaline, kaolinite, aluminum oxide, silicon dioxide and one other oxide. In some cases, the other oxide is zirconium oxide. In some cases the other oxide is titanium dioxide ($TiO_2$). In some cases the other oxide is magnesium oxide (MgO).

Kaolinite, is a layered silicate mineral comprising oxides. In some cases, various oxides are comprised within the kaolinite. In some cases, a bioceramic composition comprises additional oxides that are not part of the kaolinite. In some embodiments, a bioceramic composition comprises one oxide, two oxides, three oxides, four oxides, five oxides, six oxides, seven oxides, eight oxides, nine oxides, ten oxides, eleven oxides, twelve oxides, or more oxides. In some cases, the additional oxides are highly refractory oxides.

In some embodiments, an oxide of a bioceramic composition of matter of the disclosure has various oxidation states. An oxide of the disclosure has an oxidation number of +1, +2, +3, +4, +5, +6, +7, or +8. In some cases a bioceramic composition of the disclosure will have more than one oxide wherein at least one oxide has a different oxidation number as compared to the other oxide. For example, in some cases a bioceramic composition of the disclosure comprises an aluminum oxide ($Al_2O_3$) with a +2 or a +3 oxidation state, a silicon dioxide ($SiO_2$) with a +4 oxidation state, and a zirconium oxide ($ZrO_2$) with a +4 oxidation state.

Non-limiting examples of oxides with +1 oxidation state include: copper(I) oxide ($Cu_2O$), dicarbon monoxide ($C_2O$), dichlorine monoxide ($Cl_2O$), lithium oxide ($Li_2O$), potassium oxide ($K_2O$), rubidium oxide ($Rb_2O$), silver oxide ($Ag_2O$), thallium(I) oxide ($Tl_2O$), sodium oxide ($Na_2O$), or water (Hydrogen oxide) ($H_2O$).

Non-limiting examples of oxides with +2 oxidation state include: aluminium (II) oxide (AlO), barium oxide (BaO), beryllium oxide (BeO), cadmium oxide (CdO), calcium oxide (CaO), carbon monoxide (CO), chromium (II) oxide (CrO), cobalt (II) oxide (CoO), copper(II) oxide (CuO), iron (II) oxide (FeO), lead (II) oxide (PbO), magnesium oxide (MgO), mercury (II) oxide (HgO), nickel (II) oxide (NiO), nitric oxide (NO), palladium(II) oxide (PdO), strontium oxide (SrO), sulfur monoxide (SO), disulfur dioxide ($S_2O_2$), tin (II) oxide (SnO), titanium(II) oxide (TiO), vanadium (II) oxide (VO), or zinc oxide (ZnO).

Non-limiting examples of oxides with +3 oxidation states include: aluminium oxide ($Al_2O_3$), antimony trioxide ($Sb_2O_3$), arsenic trioxide ($As_2O_3$), bismuth (III) oxide ($Bi_2O_3$), boron trioxide ($B_2O_3$), chromium (III) oxide ($Cr_2O_3$), dinitrogen trioxide ($N_2O_3$), erbium (III) oxide ($Er_2O_3$), gadolinium (III) oxide ($Gd_2O_3$), gallium (III) oxide ($Ga_2O_3$), holmium (III) oxide ($Ho_2O_3$), indium (III) oxide ($In_2O_3$), iron (III) oxide ($Fe_2O_3$), lanthanum oxide ($La_2O_3$), lutetium (III) oxide ($Lu_2O_3$), nickel (III) oxide ($Ni_2O_3$), phosphorus trioxide ($P_4O_6$), promethium (III) oxide ($Pm_2O_3$), rhodium (III) oxide ($Rh_2O_3$), samarium (III) oxide ($Sm_2O_3$), scandium oxide ($Sc_2O_3$), terbium (III) oxide ($Tb_2O_3$), thallium (III) oxide ($Tl_2O_3$), thulium (III) oxide ($Tm_2O_3$), titanium(III) oxide ($Ti_2O_3$), tungsten (III) oxide ($W_2O_3$), vanadium (III) oxide ($V_2O_3$), ytterbium (III) oxide ($Yb_2O_3$), yttrium (III) oxide ($Y_2O_3$).

Non-limiting examples of oxides with +4 oxidation states include: carbon dioxide ($CO_2$), carbon trioxide ($CO_3$), cerium (IV) oxide ($CeO_2$), chlorine dioxide ($ClO_2$), chromium (IV) oxide ($CrO_2$), dinitrogen tetroxide ($N_2O_4$), germanium dioxide ($GeO_2$), hafnium (IV) oxide ($HfO_2$), lead dioxide ($PbO_2$), manganese dioxide ($MnO_2$), nitrogen dioxide ($NO_2$), plutonium (IV) oxide ($PuO_2$), rhodium (IV) oxide ($RhO_2$), ruthenium (IV) oxide ($RuO_2$), selenium dioxide ($SeO_2$), silicon dioxide ($SiO_2$), sulfur dioxide ($SO_2$), tellurium dioxide ($TeO_2$), thorium dioxide ($ThO_2$), tin dioxide ($SnO_2$), titanium dioxide ($TiO_2$), tungsten (IV) oxide ($WO_2$), uranium dioxide ($UO_2$), vanadium (IV) oxide ($VO_2$), or zirconium dioxide ($ZrO_2$).

Non-limiting examples of oxides with +5 oxidation states include: antimony pentoxide ($Sb_2O_5$), arsenic pentoxide ($As_2O_5$), dinitrogen pentoxide ($N_2O_5$), niobium pentoxide ($Nb_2O_5$), phosphorus pentoxide ($P_2O_5$), tantalum pentoxide ($Ta_2O_5$), or vanadium (V) oxide ($V_2O_5$). Non-limiting examples of oxides with +6 oxidation states include: chromium trioxide ($CrO_3$), molybdenum trioxide ($MoO_3$), rhenium trioxide ($ReO_3$), selenium trioxide ($SeO_3$), sulfur trioxide ($SO_3$), tellurium trioxide ($TeO_3$), tungsten trioxide ($WO_3$), uranium trioxide ($UO_3$), or xenon trioxide ($XeO_3$).

Non-limiting examples of oxides with +7 oxidation states include: dichlorine heptoxide ($Cl_2O_7$), manganese heptoxide ($Mn_2O_7$), rhenium (VII) oxide ($Re_2O_7$), or technetium (VII) oxide ($Tc_2O_7$). Non-limiting examples of oxides with +8 oxidation states include: osmium tetroxide (OsO4), ruthenium tetroxide ($RuO_4$), xenon tetroxide ($XeO_4$), iridium tetroxide ($IrO_4$), or hassium tetroxide ($HsO_4$). Non-limiting examples of oxides with various states of oxidation include antimony tetroxide ($Sb_2O_4$), cobalt (II,III) oxide ($Co_3O_4$), iron (II,III) oxide ($Fe_3O_4$), lead (II,IV) oxide ($Pb_3O_4$), manganese (II,III) oxide ($Mn_3O_4$), or silver (I,III) oxide (AgO).

In further or additional embodiments a bioceramic composition of matter of the disclosure further comprises a metal. A metal can be in elemental form, such as a metal atom, or a metal ion. Non-limiting examples of metals include transition metals, main group metals, and metals of Group 3, Group 4, Group 5, Group 6, Group 7, Group 8, Group 9, Group 10, Group 11, Group 12, Group 13, Group 14, and Group 15 of the Periodic Table. Non-limiting examples of metal include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, hafnium, tantalum, tungsten, rhenium, osmium, iridium, platinum, gold, mercury, tin, lead, and bismuth.

The proportion of minerals and oxides in a bioceramic composition can optionally be altered depending on a number of variables, including, for example, the amount of thermal radiation, more specifically far infrared radiation, to be emitted, the disease or condition to be treated, the mode of administration, the requirements of the individual subject, the severity of the disease or condition being treated, or the judgment of a practitioner.

Physical Properties

Tourmaline and kaolinite have distinct granulometric, mineralogical, chemical, and physical properties depending on, for example, whether the minerals are extracted from a particular geographic region or whether the minerals are chemically synthesized. For instance, in many parts of the world a kaolinite has a pink-orange-red coloration that is associated with an amount of an impurity(ies). Often, the impurity(ies) comprises iron oxide. In some embodiments, a kaolinite of the disclosure is of a high purity level, and it is characterized by a fine white color.

In some embodiments, a purity of the tourmaline or kaolinite is associated with an amount of infrared energy that is radiated from a bioceramic composition. In some cases the kaolinite or tourmaline of a bioceramic composition of the disclosure is greater than 99% pure, greater than 98% pure, greater than 97% pure, greater than 96% pure, greater than 95% pure, greater than 94% pure, greater than 93% pure, greater than 92% pure, greater than 91% pure, greater than 90% pure, greater than 89% pure, greater than 88% pure, greater than 87% pure, greater than 86% pure, greater than 85% pure, greater than 80% pure, greater than 75% pure, greater than 70% pure, greater than 65% pure, greater than 60% pure, or greater than 55% pure.

In some embodiments, a granularity of a kaolinite or tourmaline is associated with an amount of infrared energy that is radiated from a bioceramic composition. For instance, a bioceramic composition comprising coarser-size mineral reflects a different amount of infrared energy as compared to a bioceramic composition comprising finer-size minerals. In some embodiments, the granularity of a bioceramic composition ranges from about 100 nanometers to about 0.1 micrometers, from about 100 nanometers to about 1 micrometer, from about 100 nanometers to about 10 micrometers, from about 100 nanometers to about 25 micrometers, from about 100 nanometers to about 50 micrometers, from about 100 nanometers to about 75 micrometers, from about 100 nanometers to about 100 micrometers, from about 100 nanometers to about 125 micrometers, from about 100 nanometers to about 150 micrometers, from about 100 nanometers to about 175 micrometers, from about 100 nanometers to about 200 micrometers, from about 100 nanometers to about 225 micrometers, or from about 100 nanometers to about 250 micrometers.

In some embodiments, the granularity of a bioceramic composition ranges from about 0.5 micrometers to about 1 micrometer, from about 0.5 micrometers to about 10 micrometers, from about 0.5 micrometers to about 25 micrometers, from about 0.5 micrometers to about 50 micrometers, from about 0.5 micrometers to about 75 micrometers, from about 0.5 micrometers to about 100 micrometers, from about 0.5 micrometers to about 125 micrometers, from about 0.5 micrometers to about 150 micrometers, from about 0.5 micrometers to about 175 micrometers, from about 0.5 micrometers to about 200 micrometers, from about 0.5 micrometers to about 225 micrometers, or from about 0.5 micrometers to about 250 micrometers.

Far-Infrared Emittance, Transmission, and Reflection

Yet another aspect of the articles, compositions of matter, methods, devices, and systems described herein is a bioceramic composition that emits, transmits, and/or reflects an infrared wavelength when heated or exposed to heat. In some embodiments, provided is a bioceramic. In some embodiments, provided is a bioceramic that absorbs, stores, and/or reflects thermal energy, such as far infrared energy or rays. In some embodiments, provided is a bioceramic that emits, transmits, or reflects an infrared wavelength that is far infrared and that comprises a wavelength from about 1 micrometer to about 1 millimeter. In further or additional embodiments, provided is a bioceramic composition that emits, transmits, or reflects an infrared wavelength that is from about 3 micrometers to about 15 micrometers. In further or additional embodiments, described herein is a bioceramic composition that provides a reflectance of the bioceramic at a room temperature of 25° C. is at least 80% in an infrared range between about 7 micrometers and about 12 micrometers.

The material emissivity of a bioceramic material can be measured with, for example, a calorimeter or a Flir thermographic camera. A calorimeter can be used to measure the amount of thermal energy that can be received, store, and/or release by an apparel comprising a bioceramic. A Flir thermographic camera can create a thermal image of various types of apparel comprising a bioceramic of the disclosure. A Flir thermographic camera can detect up to thousands of measurement points in each thermal image and provide emissivity data for each image.

A bioceramic composition of the disclosure is formulated to have desired refractory properties. In some embodiments a bioceramic of the disclosure reflects about 99% of the infrared energy or rays received, about 98% of the infrared energy or rays received, about 97% of the infrared energy or rays received, about 96% of the infrared energy or rays received, about 95% of the infrared energy or rays received, about 94% of the infrared energy or rays received, about 93% of the infrared energy or rays received, about 92% of the infrared energy or rays received, about 91% of the infrared energy or rays received, about 90% of the infrared energy or rays received, about 89% of the infrared energy or rays received, about 88% of the infrared energy or rays received, about 87% of the infrared energy or rays received, about 86% of the infrared energy or rays received, about 85% of the infrared energy or rays received, about 84% of the infrared energy or rays received, about 83% of the infrared energy or rays received, about 82% of the infrared energy or rays received, about 81% of the infrared energy or rays received, about 80% of the infrared energy or rays received, about 79% of the infrared energy or rays received, about 78% of the infrared energy or rays received, about 77% of the infrared energy or rays received, about 76% of the infrared energy or rays received, about 75% of the infrared energy or rays received, about 74% of the infrared energy or rays received, about 73% of the infrared energy or rays received, about 72% of the infrared energy or rays received, about 71% of the infrared energy or rays received, about 70% of the infrared energy or rays received, about 65% of the infrared energy or rays received, about 60% of the infrared energy or rays received, about 55% of the infrared energy or rays received, about 50% of the infrared energy or rays received, about 45% of the infrared energy or rays received, about 40% of the infrared energy or rays received, about 35% of the infrared energy or rays received, about 30% of the infrared energy or rays received, about 25% of the infrared energy or rays received, about 20% of the infrared energy or rays received, about 15% of the infrared energy or rays received, about 10% of the infrared energy or rays received, or about 5% of the infrared energy or rays received.

In some cases a bioceramic of the disclosure reflects greater than 99% of the infrared energy or rays received, greater than 98% of the infrared energy or rays received, greater than 97% of the infrared energy or rays received, greater than 96% of the infrared energy or rays received, greater than 95% of the infrared energy or rays received, greater than 94% of the infrared energy or rays received, greater than 93% of the infrared energy or rays received, greater than 92% of the infrared energy or rays received, greater than 91% of the infrared energy or rays received, greater than 90% of the infrared energy or rays received, greater than 89% of the infrared energy or rays received, greater than 88% of the infrared energy or rays received, greater than 87% of the infrared energy or rays received, greater than 86% of the infrared energy or rays received, greater than 85% of the infrared energy or rays received, greater than 84% of the infrared energy or rays received, greater than 83% of the infrared energy or rays received, greater than 82% of the infrared energy or rays received, greater than 81% of the infrared energy or rays received, greater than 80% of the infrared energy or rays received, greater than 79% of the infrared energy or rays received, greater than 78% of the infrared energy or rays received, greater than 77% of the infrared energy or rays received, greater than 76% of the infrared energy or rays received, greater than 75% of the infrared energy or rays received, greater than 74% of the infrared energy or rays received, greater than 73% of the infrared energy or rays received, greater than 72% of the infrared energy or rays received, greater than 71% of the infrared energy or rays received, greater than 70% of the infrared energy or rays received, greater than 65% of the infrared energy or rays received, greater than 60% of the infrared energy or rays received, greater than 55% of the infrared energy or rays received, greater than 50% of the infrared energy or rays received, greater than 45% of the infrared energy or rays received, greater than 40% of the infrared energy or rays received, greater than 35% of the infrared energy or rays received, greater than 30% of the infrared energy or rays received, greater than 25% of the infrared energy or rays received, greater than 20% of the infrared energy or rays received, greater than 15% of the infrared energy or rays received, greater than 10% of the infrared energy or rays received, or greater than 5% of the infrared energy or rays received.

In some cases a bioceramic of the disclosure reflects fewer than 99% of the infrared energy or rays received, fewer than 98% of the infrared energy or rays received, fewer than 97% of the infrared energy or rays received, fewer than 96% of the infrared energy or rays received, fewer than 95% of the infrared energy or rays received, fewer than 94% of the infrared energy or rays received, fewer than 93% of the infrared energy or rays received, fewer than 92% of the infrared energy or rays received, fewer than 91% of the infrared energy or rays received, fewer than 90% of the infrared energy or rays received, fewer than 89% of the infrared energy or rays received, fewer than 88% of the infrared energy or rays received, fewer than 87% of the infrared energy or rays received, fewer than 86% of the infrared energy or rays received, fewer than 85% of the infrared energy or rays received, fewer than 84% of the infrared energy or rays received, fewer than 83% of the infrared energy or rays received, fewer than 82% of the infrared energy or rays received, fewer than 81% of the infrared energy or rays received, fewer than 80% of the infrared energy or rays received, fewer than 79% of the infrared energy or rays received, fewer than 78% of the infrared energy or rays received, fewer than 77% of the infrared energy or rays received, fewer than 76% of the infrared energy or rays received, fewer than 75% of the infrared energy or rays received, fewer than 74% of the infrared energy or rays received, fewer than 73% of the infrared energy or rays received, fewer than 72% of the infrared energy or rays received, fewer than 71% of the infrared energy or rays received, fewer than 70% of the infrared energy or rays received, fewer than 65% of the infrared energy or rays received, fewer than 60% of the infrared energy or rays received, fewer than 55% of the infrared energy or rays received, fewer than 50% of the infrared energy or rays received, fewer than 45% of the infrared energy or rays received, fewer than 40% of the infrared energy or rays received, fewer than 35% of the infrared energy or rays received, fewer than 30% of the infrared energy or rays received, fewer than 25% of the infrared energy or rays received, fewer than 20% of the infrared energy or rays received, fewer than 15% of the infrared energy or rays received, fewer than 10% of the infrared energy or rays received, or fewer than 5% of the infrared energy or rays received.

In some embodiments, the bioceramic reflects far infrared energy towards the body of a subject and in some embodiments the bioceramic reflects far infrared energy away from the body of the subject. A bioceramic can provide a cooling effect when it reflects infrared energy away from the body. In some embodiments a bioceramic is adjacent to or near an insulator. In some embodiments, an article comprising an insulated bioceramic provides a cooling effect to a subject, provided that when heated or exposed to heat, the bioceramic reflects the far infrared rays away from the subject.

In some embodiments, an apparel of the disclosure comprises an insulator that is in contact with or is adjacent to a bioceramic. The insulator can be used in embodiments where the apparel comprising the bioceramic is fabricated to reflect far infrared energy away from the body of a subject. In some embodiments, the insulator is a material of low thermal conductivity and prevents far infrared energy from being reflected in a direction. Different types of materials can be used to reflect infrared, non-limiting examples of insulators include rubber, glass, paper, plastic, wood, cloth, foil, or styrofoam.

An apparel of the disclosure can provide a therapeutically-effective amount of infrared to a subject. In some cases the apparel is a shirt comprising a bioceramic, and when exposed to heat, the shirt comprising the bioceramic provides at least 1.5 joules/cm$^2$ of far infrared rays to a subject. In some cases the apparel is athletic apparel, a sporting accessory, or a sports equipment including, but not limited to, orthotic inserts, athletic shoes, diving suits, life preservers, shirts, shorts, wrist bands, arm bands, head bands, gloves, jackets, pants, hats, and backpacks, skis, ski poles, snowboards, skateboards, in-line skates, bicycles, surf boards, water skis, jet skis, diving equipment, ropes, chains, goggles, and/or blankets. In some embodiments, the apparel is a sporting accessory, including but not limited to a blanket. In some embodiments, the apparel is configured for use in orthotic applications, including but not limited to orthotic inserts, shoes, and the like. In some cases the apparel is a patch (e.g. a patch that is fabricated to adhere to skin or not, such as transdermal patches, transdermal hydrogel patches, etc.), adhesive tape, such as kinesio, non-adhesive tape, pads, insoles, bedding, including a sheet, a mattress, a cover, a pillow, and/or a pillow case, a body support, a foam roller, a lotion, a soap, tape, glassware, furniture, paint, ink, a label, carpet, a mat, a food and/or beverage container, a drink koozie (e.g. bottle or can), headware (e.g. a helmet, a hat, etc.), footwear (e.g. a shoe, sneaker, sandal, etc.), an earphone, a surface, a sports surface, an artificial grass, and the like. In some cases, the apparel is a shirt, a pant, a short, dresses, a skirt, jacket, a hat, an undergarment, a sock, a cap, a glove, a scarf, a diaper, a blanket, a comforter, aduvet cover, a mattress cover, a mattress pad, and the like. In another embodiment, the article is a body support selected from a knee wrap, an elbow support, a compression arm sleeve, a compression leg sleeve, a wrist wrap, and the like.

In some embodiments, the subject matter described herein provides from 1 joule/cm$^2$ to 45 joules/cm$^2$, from 2-10 joules/cm$^2$, or from 4-6 joules/cm$^2$ of far infra-red energy rays or rays to a subject. In certain embodiments, the bioceramic formulation that provides at least 1 joule/cm$^2$, 1.5 joules/cm$^2$, at least 2 joules/cm$^2$, at least 3 joules/cm$^2$, at least 4 joules/cm$^2$, at least 5 joules/cm$^2$, at least 6 joules/cm$^2$, at least 7 joules/cm$^2$, at least 8 joules/cm$^2$, at least 9 joules/cm$^2$, at least 10 joules/cm$^2$, at least 11 joules/cm$^2$, at least 12 joules/cm$^2$, at least 13 joules/cm$^2$, at least 14 joules/cm$^2$, at least 15 joules/cm$^2$, at least 16 joules/cm$^2$, at least 17 joules/cm$^2$, at least 18 joules/cm$^2$, at least 19 joules/cm$^2$, at least 20 joules/cm$^2$, at least 21 joules/cm$^2$, at least 22 joules/cm$^2$, at least 23 joules/cm$^2$, at least 24 joules/cm$^2$, at least 25 joules/cm$^2$, at least 26 joules/cm$^2$, at least 27 joules/cm$^2$, at least 28 joules/cm$^2$, at least 29 joules/cm$^2$, at least 30 joules/cm$^2$, at least 31 joules/cm$^2$, at least 32 joules/cm$^2$, at least 33 joules/cm$^2$, at least 34 joules/cm$^2$, at least 35 joules/cm$^2$, at least 36 joules/cm$^2$, at least 37 joules/cm$^2$, at least 38 joules/cm$^2$, at least 39 joules/cm$^2$, at least 40 joules/cm$^2$, at least 41 joules/cm$^2$, at least 42 joules/cm$^2$, at least 43 joules/cm$^2$, at least 44 joules/cm$^2$, or about 45 joules/cm$^2$ of far infrared energy or rays to a subject.

In some cases, an apparel of the disclosure can provide at most 1.5 joules/cm$^2$, at most 2 joules/cm$^2$, at most 3 joules/cm$^2$, at most 4 joules/cm$^2$, at most 5 joules/cm$^2$, at most 6 joules/cm$^2$, at most 7 joules/cm$^2$, at most 8 joules/cm$^2$, at most 9 joules/cm$^2$, at most 10 joules/cm$^2$, at most 11 joules/cm$^2$, at most 12 joules/cm$^2$, at most 13 joules/cm$^2$, at most 14 joules/cm$^2$, at most 15 joules/cm$^2$, at most 16 joules/cm$^2$, at most 17 joules/cm$^2$, at most 18 joules/cm$^2$, at most 19 joules/cm$^2$, at most 20 joules/cm$^2$, at most 21 joules/cm$^2$, at most 22 joules/cm$^2$, at most 23 joules/cm$^2$, at most 24 joules/cm$^2$, at most 25 joules/cm$^2$, at most 26 joules/cm$^2$, at most 27 joules/cm$^2$, at most 28 joules/cm$^2$, at most 29 joules/cm$^2$, at most 30 joules/cm$^2$, at most 31 joules/cm$^2$, at most 32 joules/cm$^2$, at most 33 joules/cm$^2$, at most 34 joules/cm$^2$, at most 35 joules/cm$^2$, at most 36 joules/cm$^2$, at most 37 joules/cm$^2$, at most 38 joules/cm$^2$, at most 39 joules/cm$^2$, at most 40 joules/cm$^2$, at most 41 joules/cm$^2$, at most 42 joules/cm$^2$, at most 43 joules/cm$^2$, at most 44 joules/cm$^2$, or at most 45 joules/cm$^2$ of far infrared energy or rays to a subject.

In some cases, an apparel of the disclosure provides between 1.5 joules/cm$^2$ and 45 joules/cm$^2$, between 1.5 joules/cm$^2$ and 40 joules/cm$^2$, between 1.5 joules/cm$^2$ and 35 joules/cm$^2$, between 1.5 joules/cm$^2$ and 30 joules/cm$^2$, between 1.5 joules/cm$^2$ and 25 joules/cm$^2$, between 1.5 joules/cm$^2$ and 20 joules/cm$^2$, between 1.5 joules/cm$^2$ and 15 joules/cm$^2$, between 1.5 joules/cm$^2$ and 10 joules/cm$^2$, between 1.5 joules/cm$^2$ and 5 joules/cm$^2$, between 2 joules/cm$^2$ and 45 joules/cm$^2$, between 2 joules/cm$^2$ and 40 joules/cm$^2$, between 2 joules/cm$^2$ and 35 joules/cm$^2$, between 2 joules/cm$^2$ and 30 joules/cm$^2$, between 2 joules/cm$^2$ and 25 joules/cm$^2$, between 2 joules/cm$^2$ and 20 joules/cm$^2$, between 2 joules/cm$^2$ and 15 joules/cm$^2$, between 2 joules/cm$^2$ and 10 joules/cm$^2$, between 2 joules/cm$^2$ and 5 joules/cm$^2$ of far infrared energy or rays to a subject. In some cases, the apparatus is a shirt, and the shirt provides at most 45 joules/cm$^2$ of far infrared energy or rays to a subject.

Infrared energy can be absorbed, reflected, or emitted by molecules. In many cases, the thermal radiation emitted by objects on or near room temperature (approximately 25° C.) is infrared.

For example, in certain applications of the subject matter described herein, infrared energy is emitted or absorbed by molecules upon rotational and/or vibrational movements. In certain embodiments, the bioceramic materials provided herein provides infrared energy elicits vibrational modes in a molecule through a change in the dipole moment. In some embodiments, absorption of heat by a bioceramic of the instant disclosure elicits vibrational modes in at least one molecule of the bioceramic through changes in the dipole moment. Further, infrared energy from the thermal radiation, in certain embodiments, is absorbed and reflected by molecules in the bioceramic when they change their rotational-vibrational energy. In further or additional embodiments, provided herein is a bioceramic that comprises a formulation of a ceramic material and vibrational technology that provides enhanced bio-modulatory properties when in contact with or applied to a subject, including as one example a human subject.

Articles

An aspect of the articles, compositions of matter, methods, devices, and systems described herein is an article comprising a composition that comprises a bioceramic, provided that when heated or exposed to heat, the bioceramic provides a biomodulatory or physiological effect when the article is applied to a subject.

In some embodiments, provided are articles that incorporate a bioceramic composition, and articles with bioceramics applied to them. In one embodiment, the bioceramic composition is present as a coating on at least a portion of the surface of the article (for example on the inside or the outside of the article) or is incorporated directly into a substrate prior to or during manufacture of the article itself. In another embodiment, the substrate is a polymeric, cloth, or metallic material.

In some embodiments, provided are bioceramic compositions that further comprise a substrate, a binder, a solvent, a polymer, or an ink. In some embodiments, provided is a bioceramic composition that further comprises a substrate that comprises at least one elastomer. In some embodiments, provided is a bioceramic composition that further comprises a polymer that is selected from the group consisting of polyoxybenzylmethylenglycolanhydride, polyvinyl chloride, polystyrene, polyethylene, polypropylene, polacrylonitrile, polyvinyl butyral, polylactic acid, and combinations thereof. In further or additional embodiments, provided is a bioceramic composition containing an elastomer that is selected from the group consisting of polychloroprene, nylon, a polyvinyl chloride elastomer, a polystyrene elastomer, a polyethylene elastomer, a polypropylene elastomer, a polyvinyl butyral elastomer, silicone, a thermoplastic elastomer, and combinations thereof.

In some embodiments, provided is an article containing a bioceramic composition that further comprises a substrate that comprises a material selected from the group consisting of wool, silk, cotton, canvas, jute, glass, nylon, polyester, acrylic, elastane, polychloroprene, expanded polytetrafluoroethylene-containing laminate fabrics, and combinations thereof. In still further or additional embodiments, provided is an article containing a bioceramic composition that further comprises a polygel.

For example, in one embodiment a polymeric article is prepared by mixing a bioceramic composition with the polymeric substrate, or alternatively applying the bioceramic to the substrate, while the substrate is in a liquid or fluid form. In some embodiments, the amount of bioceramic composition incorporated into the polymeric substrate or that is applied to the substrate can be any suitable amount that reflects a sufficient amount of far infrared energy. In one embodiment, the bioceramic composition is added in an amount from about 1 wt % to about 75 wt % by total weight of the article. In another embodiment, the bioceramic composition is added in an amount from about 0.01 wt % to about 25 wt % by total weight of the article. In yet another embodiment, the bioceramic composition is added in an amount from about 3 wt % to about 20 wt % by total weight of the article. In a further embodiment, the bioceramic composition is added in an amount from about 7 wt % to about 13 wt % by total weight of the article. In another embodiment, the polymeric substrate is in the form of a cloth substrate, such as a shirt, which is discussed in greater detail below.

The polymeric substrate includes any polymer that is useful for preparing an article. For example, the polymeric substrate includes at least one elastomeric polymer or at least one non-elastomeric polymer. As linked polymers and polymer systems, polymer blends that include continuous and/or dispersed phases, and the like.

Elastomers include, but are not limited to, viscoelastic polymers, such as, for example, natural rubbers, synthetic rubbers, rubbery, and rubber-like polymeric materials. One example of a synthetic rubber is polychloroprene (Neoprene). In one embodiment, the elastomer is selected from polychloroprene, nylon, a polyvinyl chloride elastomer, a polystyrene elastomer, a polyethylene elastomer, a polypropylene elastomer, a polyvinyl butyral elastomer, silicone, a thermoplastic elastomer, and combinations thereof.

Thermoplastic elastomers (TPEs) are composite materials obtained from the combination of an elastomeric material and a thermoplastic material. TPEs are elastomeric materials that are dispersed and crosslinked in a continuous phase of a thermoplastic material. Examples of conventional TPEs include Santoprene®, available from Advanced Elastomers Systems, Inc. and Sarlink® available from DSM Elastomers, Inc.

In one embodiment, the non-elastomer is selected from a group of polymers that includes, but is not limited to, polyoxybenzylmethylenglycolanhydride, polyvinyl chloride, polystyrene, polyethylene, polypropylene, polacrylonitrile, polyvinyl butyral, polylactic acid, and the like.

With respect to an article that includes a cloth substrate and a bioceramic composition, the bioceramic composition can be applied to the cloth by any process known in the cloth/fabric art using a liquid or fluid carrier that contains the bioceramic composition. For example, a silk-screen printing process, a dot application process, a binder solution application process, a visible repeating pattern process or any other suitable method can be employed. Silk-screen printing is a printing process which uses a form—referred to as a frame or sieve—that includes a fabric with a very fine mesh, which is left permeable to the ink in the areas of the image to be reproduced and impermeable in the other areas. A dot application process uses specific devices, such as a syringe comprising a bioceramic, to apply the ceramics to particular portions of an apparel. A binder solution application process is used to dip fabrics into solutions or slurs comprising the bioceramics—in some cases this is used to impregnate the fabric with a bioceramic. A visible repeating pattern process is used to add a single pattern or repetitions of a pattern to an apparel. In one embodiment, the bioceramic composition can be incorporated into an ink, which is then silk-screened onto at least a portion of the surface of the cloth substrate.

In another embodiment, the bioceramic composition is combined with one or more liquid polymers (e.g. polyester and/or the like). The bioceramic/polymer composition is then extruded using methods known in the art to form fibers that are used in preparing a cloth substrate.

Cloth substrates useful herein include fabric or textile substrates prepared by any method known to one of skill in the cloth fabrication art. Such techniques include, but are not limited to, weaving, knitting, crocheting, felting, knotting, bonding, and the like. Suitable starting materials for the cloth substrates include natural or synthetic (e.g. polymeric)

fibers and filaments. In one embodiment, the cloth substrate includes, but is not limited to, a material selected from wool, silk, cotton, canvas, jute, glass, nylon, polyester, acrylic, elastane, polychloroprene, expanded polytetrafluoroethylene-containing laminate fabrics (e.g. Gore-Tex® fabric), and combinations thereof.

With respect to an article that includes a metallic substrate, the bioceramic composition is optionally applied to the metal in a liquid/fluid form by any process known in the metal processing art. For example, the bioceramic composition is optionally incorporated into a liquid/fluid carrier, such as, but not limited to, a paint, sealant, varnish, and the like, and applied to at least a portion of the surface of the metallic substrate. The amount of bioceramic composition added to a paint or other liquid/fluid carrier can be any suitable amount.

Suitable metallic substrates for use herein include any metallic substrate that is useful for preparing an article that incorporates a bioceramic composition. Exemplary metallic substrates include pure metals and alloys. In one embodiment, the metallic substrate is selected from zinc, molybdenum, cadmium, scandium, titanium, vanadium, chromium, manganese, iron, cobalt, nickel, copper, zirconium, niobium, ruthenium, rhodium, palladium, silver, tantalum, tungsten, rhenium, osmium, iridium, platinum, gold, aluminum, gallium, indium, tin, and the like.

Apparel

Virtually any article that a bioceramic composition can be applied to or incorporated within is suitable. In one embodiment, the article is selected from apparel (e.g. garments, such as: jewelry, patches (e.g. patches that are fabricated to adhere to skin, such as transdermal patches, transdermal hydrogel patches, etc.), adhesive tape, such as kinesio, non-adhesive tape, pads, insoles, performance sleeves, uniforms, casual/leisure wear, bedding, including sheet, mattresses, covers, pillows, and pillow cases, body supports, supports, foam rollers, lotions, soaps, tape, glassware, furniture, paints, inks, labels, carpets, mats, food and/or beverage containers, drink koozies (e.g. bottle or can), headware (e.g. helmets, hats, etc.), footwear (e.g. shoes, sneakers, sandals, etc.), earphones, a surface, a sports surface, artificial grass, and the like.

In some embodiments, the apparel includes athletic apparel, sporting accessories, and sports equipment including, but not limited to, orthotic inserts, athletic shoes, uniforms, footwear, insoles, performance sleeves, diving suits, life preservers, shirts, shorts, wrist bands, arm bands, headwear (e.g. skull caps), head bands, gloves, jackets, pants, hats, and backpacks, skis, ski poles, snowboards, skateboards, in-line skates, bicycles, surf boards, water skis, jet skis, diving equipment, ropes, chains, goggles, and blankets. In some embodiments, the apparel is sporting accessories, including but not limited to blankets. In some embodiments, the apparel is configured for use in orthotic applications, including but not limited to orthotic inserts, shoes, and the like.

In another embodiment, the article is apparel selected from shirts, pants, shorts, dresses, skirts, jackets, hats, undergarments, socks, caps, gloves, scarves, diapers, and the like. In yet another embodiment, the article is jewelry selected from bracelets, necklaces, earrings, medallions, pendants, rings, and the like. In still another embodiment, the article is bedding selected from blankets, sheets, pillows, pillow cases, comforters, duvet covers, mattress covers, mattress pads, and the like. In another embodiment, the article is a body support selected from knee wraps, elbow supports, compression arm sleeves, compression leg sleeves, wrist wraps, and the like. In some embodiments, the apparel includes casual/leisure wear.

In further or additional embodiments, provided is an article that incorporates a bioceramic composition, or an article with a bioceramic applied to it, provided that the article is selected from the group consisting of apparel, jewelry, patches, pads, insoles, bedding, body supports, foam rollers, lotions, soaps, tape, glassware, furniture, paints, inks, labels, carpets, mats, food and/or beverage containers, drink koozies, headwear, footwear, earphones, and combinations thereof. In further or additional embodiments, the article comprises apparel such as clothing. In some embodiments, the apparel is a casual/leisure wear apparel. In some embodiments, the apparel is an athletic apparel. In some embodiments, the apparel comprises a shirt, a jacket, shorts, or trousers. In still further embodiments, the apparel comprises a wrist band, a pad, a knee bracelet, an ankle bracelet, a sleeve, a performance sleeve, headwear (e.g. skull cap), a patch, footwear, or insoles.

In some embodiments, the article is a surface, a sports surface, or artificial grass.

Biomodulation Effect

Another aspect of the articles, compositions of matter, methods, devices, and systems described herein is a bioceramic composition that provides a biomodulatory or physiological effect when heated or exposed to heat, such as human radiation. In some embodiments, the biomodulatory or physiological effect comprises: a modulation of pain, an increase in muscle endurance, an increase in stamina, an increase in muscle strength, a modulation of the cardiorespiratory system, such as an increase in respiratory capacity, an increase in flexibility, a modulation of cellular metabolism, an improvement of analgesia, an anti-oxidative effect, an anti-fibromyalgia effect, a decrease in inflammation, a decrease in oxidative stress, a modulation of cytokine levels, a modulation of blood circulation, a reduction in intolerance to a cold environment, a reduction in a symptom of arthritis or vascular disease, an increase in cutaneous perfusion, a decrease in heart rate, a decrease in blood pressure, quicker recovery from injury or exercise, an esthetic effect such as a reduction in cellulite of the subject, an improvement in the quality of life.

A bioceramic composition of the disclosure has a biomodulatory or physiological effect in various subjects. In some embodiments, subjects are humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. A subject can be of any age. In some embodiments, subjects are, for example, elderly adults, adults, adolescents, pre-adolescents, children, toddlers, infants.

In some embodiments, the biomodulatory or physiological effect is a change in body composition. A body composition can be described in terms of body mass index, fat mass index, skeletal muscle mass index, percentage of body fat, or any combinations thereof. Various methods can be used to measure a body composition, such as the bioimpedance analysis. A bioimpedance analyzer can be used in a bioimpedance analysis to calculate an estimate of total body water (TBW). TBW can be used to estimate fat-free body mass and, by difference with body weight, body fat.

In some embodiments, the biomodulatory or physiological effect is an increase or a reduction in the expression level of a biomarker. Biomarkers broadly refer to any characteristics that are objectively measured and evaluated as indicators of normal biological processes, normal muscle function, pathogenic processes, or pharmacologic responses to bioceramics. Unless otherwise noted, the term biomarker as used herein specifically refers to biomarkers that have biophysical properties, which allow their measurements in biological samples (e.g., saliva, plasma, serum, cerebrospinal fluid, bronchoalveolar lavage, biopsy). Examples of biomarkers include nucleic acid biomarkers (e.g., oligonucleotides or polynucleotides), peptides or protein biomarkers, cytokines, hormones, or lipids. In some embodiments, an article comprising a bioceramic composition of the disclosure has a biomodulatory or physiological effect on a biomarker.

In some embodiments, a biomarker is a cytokine. Non-limiting examples of cytokines include: a) cytokines in the IL-2 subfamily, for example erythropoietin (EPO) and thrombopoietin (TPO); b) the interferon (IFN) subfamily, for example IFN-γ; c) the IL-6 subfamily; d) the IL-10 subfamily; e) the IL-1 subfamily, for example, IL-1 and IL-18, f) IL-17; or g) tumor necrosis factor family, for example tumor necrosis factor alpha (TNF-alpha or TNF-α). In some embodiments, an article comprising a bioceramic composition of the disclosure has a biomodulatory or physiological effect on a cytokine. In some embodiments, the cytokine is associated with inflammation, pain, muscle endurance, a modulation of the cardiorespiratory system, a modulation of cellular metabolism, analgesia, cellular oxidation, fibromyalgia effect, or another condition described herein.

In some embodiments, a biomarker is a wild-type protein or a protein that has been modified from a native state. For example, protein carbonylation is a type of protein oxidation that can be promoted by reactive oxygen species. It usually refers to a process that forms reactive ketones or aldehydes that are amenable to reacting with 2,4-dinitrophenylhydrazine (DNPH) to form hydrazones. Direct oxidation of side chains of lysine, arginine, proline, and threonine residues, among other amino acids, in the "primary protein carbonylation" reaction produces DNPH detectable protein products. In some embodiments, an article comprising a bioceramic composition of the disclosure has a biomodulatory or physiological effect on a protein. In some embodiments, the protein is associated with inflammation, pain, muscle endurance, a modulation of the cardiorespiratory system, a modulation of cellular metabolism, analgesia, cellular oxidation, fibromyalgia effect, or another condition described herein.

In some embodiments, a biomarker is a wild-type lipid or a lipid that has been modified from a native state. For example, lipid peroxidation refers to the oxidative degradation of lipids. It is the process in which free radicals remove electrons from the lipids in cell membranes, resulting in cell damage. In some embodiments, an article comprising a bioceramic composition of the disclosure has a biomodulatory or physiological effect on a lipid. In some embodiments, the lipid is associated with inflammation, pain, muscle endurance, a modulation of the cardiorespiratory system, a modulation of cellular metabolism, analgesia, cellular oxidation, fibromyalgia effect, or another condition described herein.

In some embodiments, the bioceramic composition provides a biomodulatory or physiological effect that comprises a change that is statistically significant. In further or additional embodiments, the biomodulatory or physiological effect comprises a change that is at least 5% in the effect. In some embodiments, the biomodulatory or physiological effect comprises a change that is at least 10% in the effect.

In still further or additional embodiments, the biomodulatory or physiological effect is pain relief, and the pain is caused by a physical activity. In still further or additional embodiments, the biomodulatory or physiological effect is inflammation.

The time needed for a bioceramic of the disclosure to modulate the effect of a biomarker often depends on the prevalent quantity, distribution and concentration of the bioceramic in contact with the subject. In some embodiments, a biomodulatory or physiological effect of a bioceramic of the disclosure is achieved within less than 10 minutes, less than 1 hour, less than 6 hours, less than 12 hours, less than 24 hours, less than 48 hours, less than 72 hours, less than 1 week, less than 2 weeks, less than 3 weeks, less than 4 weeks, less than 2 months, less than 6 months, or less than 12 months of a use of an apparel comprising a bioceramic.

Adjuvant Therapies

A bioceramic of the disclosure can provide numerous therapeutic benefits to a subject wearing an apparel that comprises the bioceramic. The far infrared energy provided by a bioceramic can be helpful for enhancing blood circulation, reducing pain, strengthening the cardiovascular system, easing joint stiffness and inflammation, and revitalizing skin cells. The far infra-red energy can provide an analgesic effect to the subject. Examples described in this instant disclosure provide qualitative and quantitative metrics of a bioceramic on numerous physiological parameters. Yet, in some cases, a bioceramic apparel can comprise another active compound. In other cases, a treatment regimen that utilizes a bioceramic can be administered alongside an adjuvant therapy.

A bioceramic can be formulated with another active compound/substance. In some instances, a bioceramic is formulated with a pharmaceutically active or inactive compound that provides a desired smell, sensation, texture. For example an apparel, e.g.: patch, can be formulated with one or more additional active or inactive substances. The one or more other substances can be, e.g., menthol, cinnamon, peppermint, cayenne pepper (capsaicin), camphor, mustards, medicinal herbs, compounds derived from such herbs, or substitutes thereof. The ratio of agent (e.g., bioceramic) to another substance can be at least 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 2:1, 1:1, 1:2, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, or 1:100.

In some cases, a bioceramic composition can have an analgesic effect on a subject that wears an apparel, e.g.: patch, shirt, shorts, etc, comprising the bioceramic. In some cases the analgesic effect is exclusively provided by the bioceramic and the additional substance. A plurality of dosages of active substances such as menthol, cinnamon, peppermint, cayenne pepper (capsaicin), mustards, medicinal herbs, compounds derived from such herbs, or substitutes thereof can be incorporated in an apparel of the disclosure. Non-limiting examples of medicinal herbs and exemplary species include Açai (*Euterpe oleracea*), Alfalfa (*Medicago sativa*), Aloe vera (e.g.: *Aloe barbadensis*), Arnica (*Arnica montana*), aroeira (*Schinus terebinthifolius*), Ashoka tree (*Saraca indica*), Asthma-plant (*Euphorbia hirta*), Astragalus (*Astragalus propinquus*), Barberry (*Berberis vulgaris*), Belladonna (*Atropa belladonna*), Bilberry (*Vaccinium myrtillus*), Bitter gourd (*Momordica charantia*), Bitter leaf (*Vernonia amygdalina*), Bitter orange (*Citrus× aurantium*), Boswellia (*Boswellia serrata*), Black cohosh (*Actaea racemosa*), Blessed thistle (*Cnicus benedictus*), Blueberries (genus *Vaccinium*), Burdock (*Arctium lappa*), bugweed (*Solanum mauritianum*), Cat's claw (*Uncaria tomentosa*), Cayenne (*Capsicum annuum*), Celery (*Apium graveolens*), Chamomille (e.g.: *Matricaria recutita* and *Anthemis nobilis*), Chaparral (*Larrea tridentata*), Chasteberry (*Vitex agnus-castus*), Chili (*Capsicum frutescens*), Cinchona (genus of about 38 species of trees whose bark is a source of alkaloids, including quinine), Clove (*Syzygium aromaticum*), Coffee senna (*Cassia occidentalis*), Comfrey (*Symphytum officinale*), Cranberry (*Vaccinium macrocarpon*), Dandelion (*Taraxacum officinale*), Digitalis (*Digitalis lanata*), Dong quai (*Angelica sinensis*), Elderberry (*Sambucus nigra*), Ephedra (*Ephedra sinica*), Eucalyptus (*Eucalyptus globulus*), European Mistletoe (*Viscum album*), Evening primrose (*Oenothera* spp.), Fenugreek (*Trigonella foenum-graecum*), Feverfew (*Tanacetum parthenium*), Flaxseed (*Linum usitatissimum*), Garlic (*Allium sativum*), Ginger (*Zingiber officinale*), Ginkgo (*Ginkgo biloba*), *Ginseng* (*Panax ginseng* and *Panax quinquefolius*), Goldenseal (*Hydrastis canadensis*), Green Tea (*Camellia sinensis*), Grape (*Vitis vinifera*), Guava (*Psidium guajava*), Hawthorn (specifically *Crataegus monogyna* and *Crataegus laevigata*), Henna (*Lawsonia Inermis*), Hoodia (*Hoodia gordonii*), Horse chestnut (*Aesculus hippocastanum*), Horsetail (*Equisetum arvense*), Jamaica dogwood (*Piscidia erythrina*/*Piscidia piscipula*), Lavender (*Lavandula angustifolia*), Lemon (*Citrus limon*), Licorice root (*Glycyrrhiza glabra*), Lotus (*Nelumbo nucifera*), Marigold (*Calendula officinalis*), Marsh-mallow (*Althaea officinalis*), Noni (*Morinda citrifolia*), Opium Poppy (*Papaver somniferum*), Oregano (*Origanum vulgare*), Peppermint (*Menthaxpiperita*), Polygala (*Paniculata* L), Podofilox (*podofilox*), Sucupira (*Pterodon emarginatus*), Summer savory (*Satureja hortensis*), Thunder God Vine (*Tripterygium wilfordii*), Turmeric (*Curcuma longa*), Willow Bark (*Salix alba*), and White willow (*Salix alba*).

In some cases, a bioceramic composition can have an anti-inflammatory effect on a subject that wears an apparel, e.g.: patch, shirt, shorts, etc, comprising the bioceramic. In some cases the anti-inflammatory effect is provided by a combination of the bioceramic and an additional substance. A plurality of dosages of anti-inflammatory substances can be incorporated in an apparel of the disclosure. Non-limiting examples of substances, medicinal herbs of origin, and exemplary species that can provide an anti-inflammatory effect include Alfalfa Alfalfa (*Medicago sativa* L.), Aloe Vera Gel (Aloe Vera Gel, Aloe vera), Andiroba Oil (*Carapa guianensis*), Ashwagandha root, (*Withania somnifera*), Balm of Gilead (*Populus* spp), Balsam of Peru (*Myroxylon pereirae*), Barberry (*Berberis vulgaris* L.), Barley Grass (*Hordeum vulgare*), Bilberry (*Vaccinium myrtillus*), Birch bark & leaf (*Betula alba*), Black Seed oil (*Nigella sativa*), Boneset (*Eupatorium perfoliatum*), Borage Seed Oil (*Borago officinalis*), *Boswellia* (Frankincense), *Boswellia* (Frankincense), *Boswellia thurifera*, Bupleurum (*Bupleurum chinense*), Calendula (*Calendula officinalis*), Cat's Claw (*Uncaria tomentosa*), Chamomile (*Matricaria recutita*), Chickweed (*Stellaria media*), Chicory root (*Cichorium intybus*), Chrysanthemum (*Chrysanthemum morifolium, C. sinense*), Cilantro (*Coriandrum sativum*), Copaiba Balsam (*Copaifera Officinalis*), Coptis (*Coptis* spp), Corn Silk (*Zea mays*), Cornflowers (*Centaurea cyanus*), Cumin (*Cuminum cyminum*), Devil's Claw (*Harpagophytum procumbens*), Echinacea (*Echinacea angustifolia*), Feverfew (*Tanacetum parthenium*), Figwort (*Scrophularia nodosa*), Ginkgo biloba (*Ginkgo biloba* L.), Grindelia (*Grindelia* spp), Immortelle Oil (*Helichrysum angustifolium*), Jamaican Dogwood (*Piscidia piscipula*), Joe-pye weed (*Eupatorium purpureum*), Marsh Mallow Root (*Althaea officinalis* L.), Mullein (*Verbascum* spp.), Oats (*Avena sativa* L.), Oregon Grape root (*Mahonia aquifolium*), Pineapple (*Ananas comosus*), Sarsaparilla Root (*Smilax sarsaparilla*), Sea Buckthorn Oil (*Hippophae* rhamnoides), Shea Nut Butter (*Butyrospermum* parkii), Soapwort (*Saponaria officinalis*), Spikenard (*Aralia racemosa*), Spilanthes (*Spilanthes acmella*), Tamanu Oil (*Calophyllum inophyllum*), Turmeric (*Curcuma longa* L.), White Peony root (*Paeonia albiflora*), White Willow Bark (*Salix Alba*), Wild Cherry Bark (*Prunus serotina*), Witch Hazel (*Hamamelis virginiana*), Yarrow (*Achillea millefolium*), and Yucca Root (*Yucca* spp).

In some cases, the active substance is an analgesic. In some cases the plurality of dosages is from about 1 mg to about 2000 mg; from about 5 mg to about 1000 mg, from about 10 mg to about 25 mg to 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg. In some cases, the plurality of times occurs is administered to a subject with a treatment regimen that occurs over a period of time. The period of time can be about, at least or at most 30 seconds, 1, 2, 3, 4, 5, 6, 7, 8, 9, 10, 11, 12, 13, 14, 15, 16, 17, 18, 19, or 20 minutes.

In addition to the benefits of using apparel comprising bioceramics on their own, subjects can combine additional treatment regimens with the use of a bioceramic apparel as co-adjuvant therapies. For example, physical therapy can be used as an adjuvant therapy treatment for a bioceramic treatment regimen. Further examples of adjuvant therapies include physical therapy, physical rehabilitation, hydrotherapy, pilates, or another suitable complementary therapy.

An adjuvant therapy regimen can be prescribed to a subject concomitantly of concurrently with a therapy regimen involving a use of a bioceramic apparel. An adjuvant therapy regimen can be carried out in many settings, such as in the home of a subject, in fitness centers and sports training facilities, in outpatient clinics or offices, health and wellness clinics, rehabilitation hospitals facilities, nursing facilities, extended care facilities, private homes, education and research centers, schools, hospices, workplaces or other environments.

Non-Invasive Methods of Providing Biomodulation to a Subject

Another aspect of the subject matter described herein is a non-invasive method of providing a biomodulatory or physiological effect in or to a subject comprising contacting an article comprising a bioceramic to the skin of the subject, provided that when heated or exposed to heat, the bioceramic composition provides far infrared thermal radiation and a biomodulatory or physiological effect to the subject in a non-invasive manner.

For example, in some embodiments, provided is a bioceramic composition that when heated or exposed to heat provides a biomodulatory or physiological effect when the article is applied to a subject, comprising:
  a. about 20 wt % to about 80 wt % kaolinite ($Al_2Si_2O_5(OH)_4$);
  b. about 1 wt % to about 30 wt % tourmaline;
  c. about 1 wt % to about 40 wt % aluminum oxide ($Al_2O_3$);
  d. about 1 wt % to about 40 wt % silicon dioxide ($SiO_2$); and
  e. about 1 wt % to about 20 wt % zirconium oxide ($ZrO_2$); provided that the amounts are by total weight of the bioceramic composition.

In further or additional embodiments, provided is a bioceramic composition of matter that when heated or exposed to heat provides a biomodulatory or physiological effect when the article is applied to a subject, comprising:
  a. about 40 wt % to about 60 wt % kaolinite ($Al_2Si_2O_5(OH)_4$);
  b. about 5 wt % to about 15 wt % tourmaline;
  c. about 15 wt % to about 25 wt % aluminum oxide ($Al_2O_3$);
  d. about 10 wt % to about 20 wt % silicon dioxide ($SiO_2$); and
  e. about 1 wt % to about 20 wt % zirconium oxide ($ZrO_2$); provided that the amounts are by total weight of the bioceramic composition. In some embodiments, the bioceramic composition comprises kaolinite in a range from about 45 wt % to about 55 wt %. In further or additional embodiments, provided is a bioceramic composition that comprises kaolinite in the range from about 47 wt % to about 53 wt %. In further or additional embodiments, provided is a bioceramic composition that contains kaolinite in a range from about 48 wt % to about 52 wt %.

In some embodiments, provided is a bioceramic composition that comprises
  a. about 50 wt % kaolinite ($Al_2Si_2O_5(OH)_4$);
  b. about 10 wt % tourmaline;
  c. about 18 wt % aluminum oxide ($Al_2O_3$);
  d. about 14 wt % silicon dioxide ($SiO_2$); and
  e. about 8 wt % zirconium oxide ($ZrO_2$).

In some embodiments, the biomodulatory or physiological effect comprises: a modulation of pain, an increase in muscle endurance, a modulation of the cardiorespiratory system, a modulation of cellular metabolism, analgesia, an anti-oxidative effect, an anti-fibromyalgia effect, a decrease in inflammation, a decrease in oxidative stress, a decrease in endoplasmic reticulum stress, a modulation of cytokine levels, a modulation of blood circulation, a reduction in intolerance to a cold environment, a reduction in a symptom of arthritis or vascular disease, an increase in cutaneous perfusion, a decrease in heart rate, a decrease in blood pressure, an esthetic effect, such as reduction of body measurements, reduction of weight, or a reduction in cellulite of the subject.

In some embodiments, the bioceramic composition provides a biomodulatory or physiological effect that comprises a change that is statistically significant. In further or additional embodiments, the biomodulatory or physiological effect comprises a change that is at least 5% in the effect.

In some embodiments, provided is an article that incorporates a bioceramic composition, or an article with a bioceramic applied to it, provided that the article is selected from the group consisting of apparel, jewelry, patches, pads, insoles, bedding, body supports, foam rollers, lotions, soaps, tape, glassware, furniture, paints, inks, labels, carpets, mats, food and/or beverage containers, drink koozies, headwear, footwear, earphones, and combinations thereof. In further or additional embodiments, the article comprises apparel such as clothing. In some embodiments, the apparel comprises a shirt, a jacket, shorts or trousers. In still further embodiments, the apparel comprises a wrist band, a pad, a knee bracelet, an ankle bracelet, a sleeve, or a patch. In some embodiments, the article comprises a surface, a sports surface, or artificial grass.

A bioceramic composition of the invention can be a combination of any compounds described herein with other chemical components, such as carriers, stabilizers, diluents, dispersing agents, suspending agents, thickening agents, and/or excipients. The bioceramic can be administered directly or indirectly to the skin of a subject. In some cases, the active compounds can be applied to an article and exposed to a subject indirectly. In other cases, the active compounds can be applied directly to the skin of a subject.

Methods of Manufacture

Another aspect of the subject matter described herein is a method of preparing an article comprising the steps of:
  a. preparing a bioceramic solution; and
  b. applying the solution to the article;
provided that the solution, when applied to the article, comprises about 20 wt % to about 80 wt % kaolinite ($Al_2Si_2O_5(OH)_4$); about 1 wt % to about 30 wt % tourmaline; about 1 wt % to about 40 wt % aluminum oxide ($Al_2O_3$); about 1 wt % to about 40 wt % silicon dioxide ($SiO_2$); and from about 1 wt % to about 20 wt % zirconium oxide ($ZrO_2$) further provided that the amounts are by total weight of the bioceramic composition. In further or additional embodiments, provided is a method for preparing an article comprising the steps of:
  a. preparing a bioceramic solution; and
  b. applying the solution on the article;
provided that when heated or exposed to heat, the bioceramic provides a biomodulatory or physiological effect when the article is applied to a subject. In further or additional embodiments, provided is a method of preparing an article whereby a solution is applied to the article by a spraying technique to an inside or an outside of the article. In some embodiments, a solution is applied to the article by a silk screening technique, a dot application technique, a binder solution application method, a visible repeating pattern approach or any other suitable method to the inside or the outside of the article optionally with use of a dye. In further or additional embodiments, an ink is not used in the method. In some embodiments, a solution is applied to the article by dipping or immersing the article in a slurry or solution. In particular embodiments, bioceramic solution comprises a polymer. In some embodiments, the polymer comprises a silicone polymer. In further or additional embodiments, a solution is applied to an inside of the article, an outside of an article, or a specific area of the article. In one embodiment, a solution is applied as small dots on the article.

For example, in some embodiments, the bioceramic comprises:
  a. about 20 wt % to about 80 wt % kaolinite ($Al_2Si_2O_5(OH)_4$);
  b. about 1 wt % to about 30 wt % tourmaline;
  c. about 1 wt % to about 40 wt % aluminum oxide ($Al_2O_3$);
  d. about 1 wt % to about 40 wt % silicon dioxide ($SiO_2$); and
  e. about 1 wt % to about 20 wt % zirconium oxide ($ZrO_2$); provided that the amounts are by total weight of the bioceramic composition.

In further or additional embodiments, provided the bioceramic composition comprising:
a. about 40 wt % to about 60 wt % kaolinite ($Al_2Si_2O_5(OH)_4$);
b. about 5 wt % to about 15 wt % tourmaline;
c. about 15 wt % to about 25 wt % aluminum oxide ($Al_2O_3$);
d. about 10 wt % to about 20 wt % silicon dioxide ($SiO_2$); and
e. about 1 wt % to about 20 wt % zirconium oxide ($ZrO_2$); provided that the amounts are by total weight of the bioceramic composition. In some embodiments, the bioceramic composition comprises kaolinite in a range from about 45 wt % to about 55 wt %. In further or additional embodiments, provided is a bioceramic composition that comprises kaolinite in the range from about 47 wt % to about 53 wt %. In further or additional embodiments, provided is a bioceramic composition that contains kaolinite in a range from about 48 wt % to about 52 wt %.

In some embodiments, provided is a bioceramic composition that comprises
a. about 50 wt % kaolinite ($Al_2Si_2O_5(OH)_4$);
b. about 10 wt % tourmaline;
c. about 18 wt % aluminum oxide ($Al_2O_3$);
d. about 14 wt % silicon dioxide ($SiO_2$); and
e. about 8 wt % zirconium oxide ($ZrO_2$).

In some embodiments, the bioceramic composition comprises tourmaline which comprises $NaFe^{2+}_3Al_6Si_6O_{18}(BO_3)_3(OH)_3$ OH.

In one embodiment, the article is apparel selected from shirts, pants, shorts, dresses, skirts, jackets, hats, undergarments, socks, caps, gloves, scarves, diapers, and the like. In yet another embodiment, the article is jewelry selected from bracelets, necklaces, earrings, medallions, pendants, rings, and the like. In still another embodiment, the article is bedding selected from blankets, sheets, pillows, pillow cases, comforters, duvet covers, mattress covers, mattress pads, and the like. In another embodiment, the article is a body support selected from knee wraps, elbow supports, compression arm sleeves, compression leg sleeves, wrist wraps, and the like.

In further or additional embodiments, provided is an article that incorporates a bioceramic composition, or an article with a bioceramic applied to it, provided that the article is selected from the group consisting of apparel, jewelry, patches, pads, insoles, bedding, body supports, foam rollers, lotions, soaps, tape, glassware, furniture, paints, inks, labels, carpets, mats, food and/or beverage containers, drink koozies, headwear, footwear, earphones, and combinations thereof. In further or additional embodiments, the article comprises apparel such as clothing. In some embodiments, the apparel comprises a shirt, a jacket, shorts or trousers. In still further embodiments, the apparel comprises a wrist band, a pad, a knee bracelet, an ankle bracelet, a sleeve, or a patch.

Optionally, articles further include one or more additional frequencies imprinted on the article using a frequency generator, i.e., a signal generating machine that emits an electromagnetic signal (audio or radio waves) at a selected frequency or frequencies. Examples of commercially available frequency generators include, but are not limited to Rife Machines (e.g. ProWave 101; F-Scan2; TrueRife F-117; Wellness Pro 2010; Global Wellness; GB4000; GB4000 BCX Ultra; and the like. In general, frequency generators produce selected frequencies that are then transmitted through a connecting cable to a commercially available frequency imprinting plate (e.g. SP9 or SP12 vortex frequency imprinting plates). In one embodiment, the frequency or frequencies range from about 0.05 Hz to about 20 MHz. In another embodiment, the frequency or frequencies range from about 5 Hz to about 5 MHz. In a further embodiment, the frequency or frequencies range from about 100 Hz to about 0.1 MHz. In yet another embodiment, the frequency or frequencies range from about 1 KHz to about 10 KHz. The article to be imprinted with the selected frequency or frequencies is exposed to the frequency emitted by the generator. To accomplish this, the article may be placed on the imprinting plate and exposed to the signal of the selected frequency or frequencies for imprinting. In one embodiment, the imprinting process takes about 5-10 minutes per cycle depending upon the amount of frequencies to be imprinted and the selected imprinting program. In another embodiment, the imprinting process takes about 5 minutes, 6 minutes, 7 minutes, 8 minutes, 9 minutes, or 10 minutes per cycle depending upon the amount of frequencies to be imprinted and the selected imprinting program. Imprinted articles may transmit the frequency imprints to a user upon contact in conjunction with the waves emitted from the bioceramic composition that is incorporated into the article.

In some embodiments, the method of manufacturing an article comprising a bioceramic of the disclosure comprises a silicon based approach. Silicones are typically inert synthetic compounds. A silicone coating is, for example, and ink, paint, oil, film, coat, grease, or resin that is silkscreened, sprayed, or otherwise directly applied to an article of the disclosure. In some embodiments, a silicone coating is pre-mixed with a bioceramic prior to being applied to an apparel. In some embodiments, a silicone coating is applied over a bioceramic as a film. In some embodiments, a silicone is mixed with a concentration of a bioceramic composition, wherein the mix provides a biomodulatory or physiological effect to a subject. In some embodiments, a higher concentration of a bioceramic is mixed with a silicone as compared to a concentration of a bioceramic that can be effectively mixed with an ink or a gel. In some embodiments, up to 50% more bioceramic is mixed with a silicone as compared to an ink or a gel.

In some embodiments, a bioceramic composition of the disclosure is mixed at a ratio of about 1 part bioceramic to about 1 part silicone, about 1 part bioceramic to about 2 parts silicone, about 1 parts bioceramic to about 3 parts silicone, about 1 part bioceramic to about 4 parts silicone, about 1 part bioceramic to about 5 parts silicone, about 1 part bioceramic to about 6 parts silicone, about 1 part bioceramic to about 7 parts silicone, about 1 part bioceramic to about 8 parts silicone, about 1 part bioceramic to about 9 parts silicone, about 1 part bioceramic to about 10 parts silicone, about 1 part bioceramic to about 11 parts silicone, about 1 part bioceramic to about 12 parts silicone, about 1 part bioceramic to about 13 parts silicone, about 1 part bioceramic to about 14 parts silicone, about 1 part bioceramic to about 15 parts silicone, about 1 part bioceramic to about 16 parts silicone, about 1 part bioceramic to about 17 parts silicone, about 1 part bioceramic to about 18 parts silicone, about 1 part bioceramic to about 19 parts silicone, about 1 part bioceramic to about 20 parts silicone, about 1 part bioceramic to about 21 parts silicone, about 1 part bioceramic to about 22 parts silicone, about 1 part bioceramic to about 23 parts silicone, about 1 part bioceramic to about 24 parts silicone, about 1 part bioceramic to about 25 parts silicone, about 1 part bioceramic to about 26 parts silicone, about 1 part bioceramic to about 27 parts silicone, about 1 part bioceramic to about 28 parts silicone, about 1 part bioceramic to about 29 parts silicone, about 1 part bioceramic to about 30 parts silicone, about 1 part bioceramic to about 31 parts silicone, about 1 part bioceramic to about 32 parts silicone, about 1 part bioceramic to about 33 parts silicone, about 1 part bioceramic to about 34 parts silicone, about 1 part bioceramic to about 35 parts silicone, or another suitable ratio.

In some embodiments, a bioceramic composition of the disclosure is mixed at a ratio of about 1 part bioceramic to about 1 part silicone, about 2 parts bioceramic to about 1 part silicone, about 3 parts bioceramic to about 1 part silicone, about 4 parts bioceramic to about 1 part silicone, about 5 parts bioceramic to about 1 part silicone, about 6 parts bioceramic to about 1 part silicone, about 7 parts bioceramic to about 1 part silicone, about 8 parts bioceramic to about 1 part silicone, about 9 parts bioceramic to about 1 part silicone, about 10 parts bioceramic to about 1 part silicone, about 11 parts bioceramic to about 1 part silicone, about 12 parts bioceramic to about 1 part silicone, about 13 parts bioceramic to about 1 part silicone, about 14 parts bioceramic to about 1 part silicone, about 15 parts bioceramic to about 1 part silicone, about 16 parts bioceramic to about 1 part silicone, about 17 parts bioceramic to about 1 part silicone, about 18 parts bioceramic to about 1 part silicone, about 19 parts bioceramic to about 1 part silicone, about 20 parts bioceramic to about 1 part silicone, about 25 parts bioceramic to about 1 part silicone, about 26 parts bioceramic to about 1 part silicone, about 27 parts bioceramic to about 1 part silicone, about 28 parts bioceramic to about 1 part silicone, about 29 parts bioceramic to about 1 part silicone, about 30 parts bioceramic to about 1 part silicone, about 31 parts bioceramic to about 1 part silicone, about 32 parts bioceramic to about 1 part silicone, about 33 parts bioceramic to about 1 part silicone, about 34 parts bioceramic to about 1 part silicone, about 35 parts bioceramic to about 1 part silicone, or another suitable ratio.

In some embodiments, the method of manufacturing an article comprising a bioceramic of the disclosure comprises a dot application approach. In a dot application method of manufacturing, a dot comprising a bioceramic, either alone or in combination with a matrix is applied to an article. In some embodiments, a matrix is, for example, a silicon matrix, a polymer matrix, or a gel matrix. In some embodiments, a polymer matrix is an innocuous holder of the bioceramic. In some embodiments, a polymer matrix has an active function in determining the amount of infrared energy that is reflected by a bioceramic. In some embodiments, the polymer is adhesive. In some embodiments, a polymer is used to glue a bioceramic composition to a fabric.

Various polymers can be mixed with a bioceramic of the disclosured and applied to an article, including, for example, silicone, hydrogels such as crosslinked poly(vinyl alcohol) and poly(hydroxy ethylmethacrylate), acyl substituted cellulose acetates and alkyl derivatives thereof, partially and completely hydrolyzed alkylene-vinyl acetate copolymers, unplasticized polyvinyl chloride, crosslinked homo- and copolymers of polyvinyl acetate, crosslinked polyesters of acrylic acid and/or methacrylic acid, polyvinyl alkyl ethers, polyvinyl fluoride, polycarbonate, polyurethane, polyamide, polysulphones, styrene acrylonitrile copolymers, crosslinked poly(ethylene oxide), poly(alkylenes), poly(vinyl imidazole), poly(esters), poly(ethylene terephthalate), polyphosphazenes, and chlorosulphonated polyolefines, and combinations thereof. In some embodiments the polymer comprises ethylene vinyl acetate.

In some embodiments, the method of manufacturing an article comprising a bioceramic of the disclosure comprises a binder or solution application approach. In some embodiments, the bioceramic composition is sprayed or dipped on an article, for example a shirt, a pad, or a bandage. In some embodiments, a binder is the film-forming component of a bioceramic paint. In some cases, a binder comprises materials that impart adhesion of the bioceramic to the apparel and strongly influence properties such as glossiness, durability, flexibility, and resilience of the applied bioceramic. In some embodiments, binders include synthetic or natural resins such as alkyls, acrylics, vinyl-acrylics, vinyl acetate/ ethylene (VAE), polyurethanes, polyesters, melamine resins, epoxy, or oils.

Further non-erodible materials suitable for inclusion in a apparel with a bioceramic include, for example, proteins such as zein, resilin, collagen, gelatin, casein, silk, wool, polyesters, polyorthoesters, polyphosphoesters, polycarbonates, polyanhydrides, polyphosphazenes, polyoxalates, polyaminoacids, polyhydroxyalkanoates, polyethyleneglycol, polyvinylacetate, polyhydroxyacids, polyanhydrides, hydrogels including poly(hydroxyethyl methylacrylate), polyethylene glycol, poly(N-isopropylacrylamide), poly(N-vinyl-2-pyrrolidone), cellulose polyvinyl alcohol, silicone hydrogels, polyacrylamides, and polyacrylic acid.

In some embodiments, the method of manufacturing an article comprising a bioceramic of the disclosure comprises a visible repeating pattern process. A method of visible repeating patterns often comprises a first step of printing, silk screening, spraying, or using another method to apply a pattern with regular ink (without a bioceramic) on an apparel. A method of visible repeating patterns often comprises a second step of applying a second material, such as a spray, a silicone, or a binder base comprising a bioceramic over the first pattern. A method of visible repeating patterns can optionally use any of the aforementioned materials, including silicones, binders, and polymers.

The methods of manufacture described herein are used to apply a bioceramic at a specific location within an apparel or throughout the apparel. For instance, a method of manufacture disclosed herein can be used to apply a bioceramic to an inner side, to an outer side, or any inner/outer combination of an apparel. In most embodiments, application of a bioceramic to an inner side, an outer, or any inner/outer combination of an apparel does not affect a biomodulatory or physiological effect of a bioceramic.

In some embodiments, an apparel comprises about 5% bioceramics by total weight, about 10% bioceramics by total weight, about 15% bioceramics by total weight, about 20% bioceramics by total weight, about 25% bioceramics by total weight, about 30% bioceramics by total weight, about 35% bioceramics by total weight, about 40% bioceramics by total weight, about 45% bioceramics by total weight, about 50% bioceramics by total weight, about 55% bioceramics by total weight, about 60% bioceramics by total weight, about 65% bioceramics by total weight, about 70% bioceramics by total weight, about 75% bioceramics by total weight, about 80% bioceramics by total weight, about 85% bioceramics by total weight, about 90% bioceramics by total weight, or about 95% bioceramics by total weight.

In some embodiments, a bioceramic is applied to a portion or to the entire surface of apparel. In some cases, a bioceramic composition is applied to greater than 1% of the surface area, greater than 5% of the surface area, greater than 10% of the surface area, greater than 15% of the surface area, greater than 20% of the surface area, greater than 25% of the surface area, greater than 30% of the surface area, greater than 35% of the surface area, greater than 40% of the surface area, greater than 45% of the surface area, greater than 50% of the surface area, greater than 55% of the surface area, greater than 60% of the surface area, greater than 65% of the surface area, greater than 70% of the surface area, greater than 75% of the surface area, greater than 80% of the surface area, greater than 85% of the surface area, greater than 90% of the surface area, greater than 95% of the surface area, or greater than 99% of the surface area of an apparel.

In some cases, a bioceramic composition is applied to no more than 1% of the surface area, no more than 5% of the surface area, no more than 10% of the surface area, no more than 15% of the surface area, no more than 20% of the surface area, no more than 25% of the surface area, no more than 30% of the surface area, no more than 35% of the surface area, no more than 40% of the surface area, no more than 45% of the surface area, no more than 50% of the surface area, no more than 55% of the surface area, no more than 60% of the surface area, no more than 65% of the surface area, no more than 70% of the surface area, no more than 75% of the surface area, no more than 80% of the surface area, no more than 85% of the surface area, no more than 90% of the surface area, no more than 95% of the surface area, or no more than 99% of the surface area of an apparel.

In some cases, a bioceramic composition is applied to about 1% of the surface area, about 2% of the surface area, about 3% of the surface area, about 4% of the surface area, about 5% of the surface area, about 6% of the surface area, about 7% of the surface area, about 8% of the surface area, about 9% of the surface area, about 10% of the surface area, about 11% of the surface area, about 12% of the surface area, about 13% of the surface area, about 14% of the surface area, about 15% of the surface area, about 16% of the surface area, about 17% of the surface area, about 18% of the surface area, about 19% of the surface area, about 20% of the surface area, about 21% of the surface area, about 22% of the surface area, about 23% of the surface area, about 24% of the surface area, about 25% of the surface area, about 26% of the surface area, about 27% of the surface area, about 28% of the surface area, about 29% of the surface area, about 30% of the surface area, about 31% of the surface area, about 32% of the surface area, about 33% of the surface area, about 34% of the surface area, about 35% of the surface area, about 36% of the surface area, about 37% of the surface area, about 38% of the surface area, about 39% of the surface area, about 40% of the surface area, about 41% of the surface area, about 42% of the surface area, about 43% of the surface area, about 44% of the surface area, about 45% of the surface area, about 46% of the surface area, about 47% of the surface area, about 48% of the surface area, about 49% of the surface area, about 50% of the surface area, about 51% of the surface area, about 52% of the surface area, about 53% of the surface area, about 54% of the surface area, about 55% of the surface area, about 56% of the surface area, about 57% of the surface area, about 58% of the surface area, about 59% of the surface area, about 60% of the surface area, about 61% of the surface area, about 62% of the surface area, about 63% of the surface area, about 64% of the surface area, about 65% of the surface area, about 66% of the surface area, about 67% of the surface area, about 68% of the surface area, about 69% of the surface area, about 70% of the surface area, about 71% of the surface area, about 72% of the surface area, about 73% of the surface area, about 74% of the surface area, about 75% of the surface area, about 76% of the surface area, about 77% of the surface area, about 78% of the surface area, about 79% of the surface area, about 80% of the surface area, about 81% of the surface area, about 82% of the surface area, about 83% of the surface area, about 84% of the surface area, about 85% of the surface area, about 86% of the surface area, about 87% of the surface area, about 88% of the surface area, about 89% of the surface area, about 90% of the surface area, about 91% of the surface area, about 92% of the surface area, about 93% of the surface area, about 94% of the surface area, about 95% of the surface area, about 96% of the surface area, about 97% of the surface area, about 98% of the surface area, about 99% of the surface area, or about 100% of the surface area of an apparel.

Cosmetic Applications

In some aspects, the present invention relates to a cosmetic composition comprising a composite powder, foam, liquid, oil, wax, base, or emulsifying agent that comprises a far-infrared emitting bioceramic. The cosmetic compositions of the invention can comprise an effective amount of a bioceramic in various cosmetic vehicles, such as a cosmetic lotion, cream, mascara, mask, gel patch, and general make-up. A cosmetic composition of the disclosure can comprise various ratios of bioceramics to cosmetic vehicle. For instance, a composition of the disclosure can be 1 part bioceramic 1 part cosmetic vehicle, 1 part bioceramic 2 parts cosmetic vehicle, 1 part bioceramic 3 parts cosmetic vehicle, 1 part bioceramic 3 parts cosmetic vehicle, 1 part bioceramic 4 parts cosmetic vehicle, 1 part bioceramic 5 parts cosmetic vehicle, 1 part bioceramic 6 parts cosmetic vehicle, 1 part bioceramic 7 parts cosmetic vehicle, 1 part bioceramic 8 parts cosmetic vehicle, 1 part bioceramic 9 parts cosmetic vehicle, 1 part bioceramic 10 parts cosmetic vehicle, 1 part bioceramic 11 parts cosmetic vehicle, 1 part bioceramic 12 parts cosmetic vehicle, 1 part bioceramic 13 parts cosmetic vehicle, 1 part bioceramic 14 parts cosmetic vehicle, 1 part bioceramic 15 parts cosmetic vehicle, 1 part bioceramic 16 parts cosmetic vehicle, 1 part bioceramic 17 parts cosmetic vehicle, 1 part bioceramic 18 parts cosmetic vehicle, 1 part bioceramic 19 parts cosmetic vehicle, 1 part bioceramic 20 parts cosmetic vehicle, 1 part bioceramic 21 parts cosmetic vehicle, 1 part bioceramic 22 parts cosmetic vehicle, 1 part bioceramic 23 parts cosmetic vehicle, 1 part bioceramic 24 parts cosmetic vehicle, 1 part bioceramic 25 parts cosmetic vehicle, 1 part bioceramic 26 parts cosmetic vehicle, 1 part bioceramic 27 parts cosmetic vehicle, 1 part bioceramic 28 parts cosmetic vehicle, 1 part bioceramic 29 parts cosmetic vehicle, 1 part bioceramic 30 parts cosmetic vehicle, or another suitable ratio. In some cases, a bioceramic composition of the disclosure can be applied directly to the skin.

Another aspect of the subject matter described herein are cosmetic compositions, and more particularly cosmetic compositions for reducing facial expression marks, scars, blemishes on the skin, as well as for eye puffiness reduction/control. A cosmetic composition effective for reducing facial expression marks, scars, redness of blemishes on the skin, as well as for eye puffiness reduction/control may be prepared by addition of a bioceramic to a cosmetic composition such as a lotion, cream, mascara, mask, gel patch, oil, base, wax, emulsifying agents, or general make-up powders with various colors. The cosmetic compositions provide a beneficial biomodulatory effect by providing far-infrared energy that reduces facial expression marks on the skin, reduces eye puffiness, and reduces blemishes thereby making skin marks less obvious.

A composition of the disclosure can be applied to various skin types. Skin types include normal, oily, dry, sensitive, and combination skin types. Some people also have a combination of skin types in different areas of their skin. A composition of the disclosure can be applied to skin types that vary in a) water content, which affects skin's comfort and elasticity; b) oil (lipid) content, which can affect skin's softness; and c) sensitivity level. A cosmetic composition of the disclosure can provide beneficial far-infrared radiation to various types of skins. For instance, when exposed to drying factors, skin can crack, peel, or become itchy, irritated, or inflamed. A cosmetic composition of the disclosure can help alleviate the itchiness, irritation, soreness, or inflammation.

A composition of the disclosure can be applied directly or indirectly to the skin. For instance, a far-infrared emitting bioceramic can be formulated inside an eye mask, and the eye mask can be worn by a subject to reduce a puffiness of the eye. A far-infrared emitting bioceramic can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

A far-infrared emitting bioceramic can be formulated as an oil or emulsion. Suitable lipophilic solvents or vehicles that can be formulated with a bioceramic described herein include fatty oils such as sesame oil, or synthetic fatty acid esters, such as ethyl oleate or triglycerides, or liposomes. Aqueous suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active bioceramic ingredient can be in powder form for constitution with a suitable vehicle, e.g., sterile pyrogen-free water, before use.

In some cases, transdermal patches can provide controlled delivery of far-infrared energy to a subject. For instance, the rate of far-infrared absorption can be slowed by using rate-controlling membranes or by trapping the compound within a polymer matrix or gel. Conversely, absorption enhancers can be used to increase absorption or far-infrared energy. An absorption enhancer or carrier can include absorbable pharmaceutically acceptable solvents to assist passage through the skin. For example, transdermal devices can be in the form of a bandage comprising a backing member, a reservoir containing compounds and carriers, a rate controlling barrier to deliver the compounds to the skin of the subject at a controlled and predetermined rate over a prolonged period of time, and adhesives to secure the device to the skin.

Generally, a coloring agent and/or a resin can be used along with a bioceramic composition in a cosmetic application. A variety of coloring agents and resins can be used to form and color cosmetics, including inorganic and organic dyes or pigments. Polymeric materials approved by the Food and Drug Administration as "Indirect Food Additives" can be used as resins for use in the make-up compositions comprising bioceramics. Non-limiting examples of polymeric materials that can be used as resins for the make-up compositions include, acrylic and modified acrylic plastics; acrylonitrile/butadiene/styrene copolymers; acrylonitrile/butadiene/styrene/methyl methacrylate copolymers; acrylonitrile/styrene copolymers; acrylonitrile/styrene copolymers modified with butadiene/styrene elastomer; cellophane; cyclohexylene dimethylene terephthalate and 1,4-cyclohexylene dimethylene isophthalate copolymers; ethylene-acrylic acid copolymers; ethylene-1,4-cyclohexylene dimethylene terephthalate copolymers; ethylene-ethyl acrylate copolymers; ionomeric resins; ethylene-methyl acrylate copolymer resins; ethylene-vinyl acetate copolymers; ethylene-vinyl acetate-vinyl alcohol copolymers; fluorocarbon resins; hydroxyethyl cellulose film, water-insoluble; isobutylene polymers; isobutylenebutene copolymers; 4,4'-isopropylidenediphenolepichlorohydrin resins; melamine-formaldehyde resins; nitrile rubber modified acrylonitrile-methyl acrylate copolymers; nylon resins; olefin polymers; perfluorocarbon resins; polyarylate resins; polyarylsulfone resins; poly-1-butene resins and butene/ethylene copolymers; polycarbonate resins; polyester elastomers; polyetherimide resins; polyethylene resins, carboxyl modified; polyethylene, chlorinated; polyethylene, fluorinated; polyethylene, oxidized; polyethylene phthalate polymers; poly(p-methylstyrene) and rubber-modified poly(p-methylstyrene); polystyrene and rubber-modified polystyrene; polysulfide polymer-polyepoxy resins; polysulfone resins; poly (tetramethylene terephthalate); polyvinyl alcohol films; polyurethane resins; styrene block polymers; styrene-maleic anhydride copolymers; styrene-methyl methacrylate copolymers; textryls; urea-formaldehyde resins; vinyl chloride-ethylene copolymers; vinyl chloride-hexene-1 copolymers; vinyl chloride-lauryl vinyl ether copolymers; vinyl chloride-propylene copolymers; vinylidene chloride/methyl acrylate copolymers; vinylidene chloride/methyl acrylate/methyl methacrylate polymers; ethylene polymers, chlorosulfonated; 4,4'-isopropylidenediphenol-epichlorohydrin thermosetting epoxy resins; mineral reinforced nylon resins; perflourocarbon cured elastomers; phenolic resins; polyester resins, cross-linked; polyether resins, chlorinated; polyethersulfone resins; polyamide-imide resins; poly(2,6-dimethyl-1,4-phenylene) oxide resins; polyoxymethylene copolymers; polyoxymethylene homopolymers; polyphenylene sulfide resins; polyvinylidene fluoride resins; and styrene-divinylbenzene resins, cross-linked.

Methods for the preparation of cosmetic compositions comprising the far infra-red emitting bioceramics described herein include formulating the compounds with one or more inert, pharmaceutically-acceptable excipients or carriers to form a solid, semi-solid, foam, wax, cream, lotion, or liquid composition. These compositions can also contain minor amounts of nontoxic, auxiliary substances, such as wetting or emulsifying agents, pH buffering agents, and other pharmaceutically-acceptable additives.

Patterns

A bioceramic may be added to an article of apparel in a variety of regular or irregular patterns. A bioceramic pattern may cover the entirety of the surface of an apparel or a pattern may cover a portion of an apparel. A bioceramic pattern covering an apparel may have regions of discontinuity having a variety of shapes and sizes. For example, a pattern may be a honeycomb pattern (e.g., with hexagonal regions of discontinuity), a grid pattern (e.g., with square-shaped or rectangular regions of discontinuity), a random pattern (e.g., with regions of discontinuity distributed randomly), and so forth. In general, the regions of discontinuity may be distributed across the surface at intervals that are regularly spaced or not regularly spaced. The regions of discontinuity may be formed with a variety of regular or irregular shapes such as, for example, circular, half-circular, diamond-shaped, hexagonal, multi-lobal, octagonal, oval, pentagonal, rectangular, square-shaped, star-shaped, trapezoidal, triangular, wedge-shaped, and so forth. If desired, one or more regions of discontinuity may be shaped as logos, letters, or numbers. In some embodiments, the regions of discontinuity may have sizes of about 0.1 mm, about 1 mm, about 2 mm, about 3 mm, about 4 mm, about 5 mm, about 6 mm, about 7 mm, about 8 mm, about 9 mm, about 10 mm, or other desired distance. In some embodiments, the regions of discontinuity may range from 0.1 mm to about 1 mm, from 1 mm to about 5 mm, from 1 mm to about 10 mm, from 1 mm to about 15 mm, from 1 mm to about 20 mm, from 1 mm to about 25 mm, from 1 mm to about 30 mm, or other desired distance. In general, the regions of discontinuity may have the same or different shapes or sizes.

A bioceramic pattern may be applied as a coat covering an interior and/or an exterior surface of an article of apparel. A bioceramic pattern may permeate a material, such as a fabric. A bioceramic pattern may cover various portions of a fabric in a continuous, discontinuous, regular, or irregular pattern, or any combination thereof. A bioceramic pattern may permeate less than 1%, less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, less than 95%, or less than 99%, of an interior surface of an article of apparel, an exterior surface of an article of apparel, or any combination thereof.

The following non-limiting examples serves to further illustrate the present invention.

EXAMPLES

Example 1: Preparation of a Bioceramic Powder Composition

The kaolinite is extracted in the outskirts of the city of Parintins, in the Amazon State, Brazil. The city is located in the Lower Amazon Region (coordinates: latitude: 2° 37' 42" south/longitude: 56° 44' 11" west of Greenwich, 50 m above sea level). Alternatively, the kaolinite is obtained by purchasing it from a mining company/supplier.

The extracted kaolinite is washed with hydrogen peroxide ($H_2O_2$) and allowed to dry. The dried kaolinite is then finely ground and mixed with tourmaline; aluminum oxide ($Al_2O_3$); silicon dioxide ($SiO_2$); and zirconium oxide ($ZrO_2$) until a homogeneous mixture is achieved. The resulting bioceramic composition contains 50 wt % kaolinite, 10 wt % tourmaline, 18 wt % aluminum oxide, 14 wt % silicon dioxide, and 8 wt % zirconium oxide.

A bioceramic composition was also synthesized. The resulting bioceramic contains any composition described herein, including about 50% kaolinite, about 10% tourmaline, about 18% aluminum oxide, about 14% silicon dioxide, and about 8% zirconium oxide.

Example 2: Application to Clothing

A bioceramic of the disclosure is a refractory, inorganic, polycrystalline composition that can be reduced to powdered format by grinding, crushing, or another suitable. In powder form, a bioceramic is incorporated into a range of materials; including various types of polymers and inks. A powered bioceramic is incorporated into a cloth substrate to applying an ink comprising the bioceramic to the cloth.

A cloth substrate that includes 88 wt % polyamide and 12 wt % elastane was obtained. A bioceramic composition prepared according to the method of Example 1 was incorporated onto a plastisol ink in an amount of 10-50 wt % and mixed. The mixture was applied to the cloth substrate using a traditional silkscreen process. The specific type of ink was selected based on the chosen fabric.

Example 3: Silkscreen Application of Bioceramics to Clothing (e.g., a Shirt)

Concentration: ceramic materials are mixed with the ink at a 30% concentration of the total weight/volume.

Mixing process: ceramics were added to the ink gradually. Regular mixing process was applied using a mixer that is customarily used for pigment and ink mixing. The materials are mixed until a consistent and uniform mix/slurry was achieved. The process was fast as the ceramics mix well with all different types of inks.

Durability of the slurry/mix: a well sealed mixture is stored and used up to one week after production.

Application: the bioceramic material was applied in the same manner as regular ink through a silk-screening process. It was observed that due to their particle size, the ceramic materials may scratch the screens. It is recommended that after every 1000 shirts the screens are checked/inspected and if needed they should be replaced, especially to avoid defects on the application and the look of the logo.

Fabric selection: the ceramics did not cause any observable damage to the fabric. It was observed that fabrics that are too porous or cannot go through the regular drying process commonly used in silk-screening should be avoided.

Ink selection: the ceramics may increase ink density and the type of ink should be selected by a person of ordinary skill in the art based on the type of fabric used.

Drying process after silk-screening: due to the fact that the ceramics may contain a small amount of moisture, it was observed that the drying may take longer than usual. The duration and intensity of the process depend upon the type of fabric and ink selected. After the first experimental run with the fabric and ink selected, the product should be subjected to a wash test to make sure the ink does not come off or crack.

A silk screening process is used to provide a ceramic to an apparel with a desired pattern. A silk screen approach is used to intercalate an imprint with a pattern into a shirt. FIG. 1 illustrates a shirt comprising a ceramic composition of the disclosure that was fabricated with a silkscreen application.

Example 4: Dot Application Approach of Applying Bioceramics to Clothing (e.g., a Shirt)

Concentration: ceramic materials are mixed with either silicone or a polymer, such as m-gel at a ratio of 1 part ceramic to 9 parts silicone. Alternatively, ceramic materials are mixed with a polymer, such as m-gel at a ratio of 1 part ceramic to 9 parts m-gel.

Application: a device has been used to apply the ceramic dots to the fabric with a desired pattern. A dot application approach is used to, for instance, intercalate a pattern into a shirt. FIG. 1 illustrates a shirt comprising a ceramic composition of the disclosure.

Fabric selection: the ceramics do not cause any observable damage to the fabric. A dot application approach is used to apply a bioceramic to specific areas of fabrics or apparel. In some instances, a dot application approach is used to apply the ceramics to specific areas of the piece even on top of the silkcreen in order to achieve a higher concentration of ceramics per surface area. A dot application approach is used around the shoulders, elbows, or any area where it is desirable to apply a higher concentration of ceramics.

Example 5: Binder/Solution Approach of Applying Bioceramics to Clothing (e.g., a Shirt)

Concentration: as an alternative to mixing a ceramic to an ink and using a silkscreen or dot approach to apply the ceramic to a fabric, a binder solution approach is used. A binder solution comprises up to 50% ceramic and up to 50% binder solution or slurry.

Application: a fabric is placed in a slurry solution comprising a ceramic and a binder at a desired concentration. The fabric is removed from the slurry solution and allowed to dry. The fabric is now impregnated or infused with a ceramic of the disclosure. The fabric that is impregnated or infused with the ceramic is directly placed in contact with a skin of a subject.

Example 6: Visible Repeating Pattern Approach of Applying Bioceramics to Clothing (e.g., a Shirt)

Concentration: a first solution comprising an ink is prepared. A second solution, slur, or binder comprising from about 10% ceramic to about 50% ceramic is prepared by mixing a ceramic of the disclosure with the ink, slur, or binder.

Application: a first pattern is sprayed, printed, silk screened, or otherwise applied to a fabric. The first pattern consists of ink and does not contain a bioceramic material. A second pattern comprising from about 10% ceramic to about 50% ceramic is subsequently sprayed, printed silk screened, or otherwise applied to the surface of the first pattern. Optionally, a silicone coating is applied over the second pattern to provide a glossy appearance of the pattern applied to the fabric. Optionally, a silicone coating is mixed with a concentration of the ceramics prior to being applied as a coat.

Example 7: Fabrication of a Pad

A thermoplastic elastomer (TPE) is liquefied with a bioceramic of the disclosure. The TPE and the ceramic are mixed at a concentration of about 1 part ceramic to 1 part TPE, 1 part ceramic to 2 parts TPE, 1 part ceramic to 3 parts TPE, 1 part ceramic to 4 parts TPE, 1 part ceramic to 5 parts TPE, 1 part ceramic to 6 parts TPE, 1 part ceramic to 7 parts TPE, 1 part ceramic to 8 parts TPE, or 1 part ceramic to 9 parts TPE. The liquefied mix is placed on a mold. The mix of TPE and bioceramic is allowed to solidify to provide an apparel with the shape of the mold. The apparel is removed from the mold. The apparel is a thermoplastic pad comprising a bioceramic, such as the pad illustrated in FIG. 3.

Example 8: Bioceramics as Anti-Inflammatory Agents and Cytokine Modulation

Laboratory mice are administered injections of the bioceramic composition of Example 1. On the 5th day post CFA injection (after 5 consecutive Bioceramic treatments) the right hindpaw of the mice is collected and used to estimate the cytokine levels by enzyme-linked immunosorbent assay (ELISA), with sample values corrected by protein levels. Optionally, the following cytokines are evaluated, individually or as a group: TNF-α, IL-1β, IL-10 and IL-6. The absorbance for the aforementioned cytokines could be measured using a microplate reader at 450 and 550 nm. Cytokine levels of mice could be determined to confirm the anti-inflammatory effect of the bioceramic compositions.

Example 9: Determination of Oxidative Stress and Anti-Oxidative Enzyme Levels Laboratory mice are administered injections of the bioceramic composition of Example 1.

On the 5th day post CFA injection right hindpaw tissues (skin and muscles) of the mice can be collected and used to assess oxidative damage. For this test the formation of thiobarbituric acid reactive species (TBARS) is measured during an acid-heating reaction. The samples are mixed with 1 mL of trichloroacetic acid (TCA) 10% and 1 mL of thiobarbituric acid 0.67% and then heated in a boiling water bath for 15 min. TBARS levels are determined by the absorbance at 535 nm. Results are expressed as malondialdehyde (MDA) equivalents (nmol/mg protein).

Oxidative damage to proteins are measured by the quantification of carbonyl groups based on the reaction with dinitrophenylhydrazine (DNPH), as previously described. Proteins are precipitated by the addition of 20% trichloroacetic acid and are optionally redissolved in DNPH; the absorbance is read at 370 nm. Results can be reported as nmol of carbonyl content per mg of protein (nmol/mg protein) or results can be reported using another suitable unit.

To determine catalase (CAT) activity, the paw tissues are sonicated in 50 mmoL/L phosphate buffer (pH 7.0), and the resulting suspension is centrifuged at 3000×g for 10 min. The supernatant is used for enzyme assay. CAT activity is measured by the rate of decrease in hydrogen peroxide absorbance at 240 nm. Results can be reported as (U/mg protein) or any other suitable unit.

Superoxide dimuthase (SOD) activity is assayed by measuring the inhibition of adrenaline auto-oxidation, as previously described. All biochemical measures are normalized to the protein content, with bovine albumin as standard. All the results are normalized by protein concentration measured by the Lowry assay. Results are reported as (U/mg protein) or any other suitable unit.

Example 10: Effect of Far Infrared Emitted by Bioceramics on Parameters of Physical Performance in Mice Objective: To evaluate the effect of Far Infrared therapy emitted by bioceramics on parameters of physical performance in mice subjected to a swimming protocol.

Methods: Experiments were conducted with male Swiss mice (30-35 g) after approval of the University of South of Santa Catarina Ethics Committee. The mice were randomly divided into 2 groups and subjected to a 30 min 21 day swimming protocol. For treatment, a bioceramics pad containing the composition described in Example 1 (80% Bio-Corn PVC—20% Bioceramic materials) was placed inside the animals box for three weeks. Control animals were placed on a sham pad (100% BioCorn PVC without bioceramics) and underwent the same experimental protocol. At the end of each week body weight and food and water intake were measured and an exhaustion test was conducted in which the mice were put to swim until exhaustion with a charge of 5% of body weight tied to their tail. Point of Exhaustion was determined when the animal could not maintain its head out of the water surface for more than 5 seconds. At the end of third week right hind limb grasping strength was conducted using a strain gauge force feedback system and the gastrocnemius muscle weight was assessed with an analytical scale.

Results: Far infrared emitted by a bioceramic pad containing the composition of Example 1 increased time to reach exhaustion in forced swimming test (133.1%, 60.4% and 90.83% in weeks 1 to 3) but did not affect body weight, water or food consumption. Although gastrocnemius muscle weight was not affected, the bioceramic of Example 1 increased hindlimb grasping strength in 6.6%.

Conclusion: Far Infrared therapy emitted by a bioceramic of Example 1 increased hindlimb grasping strength and time to reach exhaustion of mice subjected to a three week swimming protocol. These results indicate increased resistance, muscle endurance, and overall stamina (energy levels).

Example 11: Far Infrared Therapy Emitted by Bioceramics Improves Postural Sway in Human Athletes Objective: The objective of the present study was to evaluate the effect of far infrared therapy emitted by bioceramics on the orthostatic balance of judo practitioners (Judokas) of a Brazilian university team in a double blind controlled trial.

Methods: A total of 17 athletes (7 women and 10 men; 23±4.75 of age) of the University of South of Santa Catarina (UNISUL) wore either a bioceramics shirt containing the composition of Example 1 shirt (bioceramics silkscreened shirt) or a sham shirt (without bioceramics) during practice (for two hours, five times a week for a period of five months). The Judokas were of seven different weight categories and were evenly divided in the two experimental groups (bioceramic or sham shirt) in such a way that each group had approximately the same amount of athletes of each weight category. Center of pressure (CoP) parameters (length, sway area, velocity in anteroposterior and mediolateral direction) were measured in three 30 sec duration static bipedal standing tasks—the athletes were asked to maintain their eyes opened and stand in a narrow stance on a Balance Platform (T-Plate Balance Platform, Medicapteurs, France). Evaluations were conducted before and after 5 months of use of the bioceramic shirts.

Results: The results obtained demonstrated statistically significant decreases (p<0.05) in all CoP parameters evaluated (length, sway area, velocity in anteroposterior and mediolateral direction) in bioceramics shirt group athletes when compared with sham shirt group.

Conclusion: Far Infrared therapy emitted by a bioceramics shirt containing the composition of Example 1 positively affected the orthostatic balance of Judo practitioners of a Brazilian university team.

Example 12: Far Infrared Emitted by Bioceramics Reduces Mechanical and Thermal Hyperalgesia in an Animal Model of Chronic Inflammatory Pain Objective: This study evaluated the effect of far infrared emitted by the bioceramic composition of Example 1 incorporated into a pad against mechanical and thermal hyperalgesia as well as paw temperature increase and edema formation in a mice model of inflammatory pain.

Methods: Experiments were conducted with male Swiss mice (30-35 g) after approval of the University of South of Santa Catarina Ethics Committee. The animals underwent intraplantar injection of Freud's complete adjuvant (CFA, 20 µl-70%) and for treatment the bioceramics pad (80% BioCorn PVC—20% Bioceramic materials) was placed inside the animals box. After 24 h of exposure to the product, mechanical and thermal hyperalgesia was assessed as response frequency to 10 presentations of a 0.4 g von frey filament or by hot stimuli applied to the animals right hind paw (Hot Plate Method). Evaluations were performed daily for 10 days. After evaluation the animals were placed in their boxes and re-exposed to the Pad until the subsequent evaluation (24 hours later). In addition, edema formation and hind paw temperature were evaluated on experimental days 1, 3 and 10 with a micrometer and a digital thermometer, respectively. Control animals were placed on a sham pad (100% BioCorn PVC without bioceramics) and underwent the same experimental protocol.

Results: Acute exposure to the bioceramics pad induced analgesia which lasted for 2 hours (P<0.001—maximum inhibition of 53±11%). Chronic treatment reduced mechanical hyperalgesia on all evaluation days and thermal hyperalgesia on days 1 and 3. In addition, the treatment decreased paw temperature on days 1 and 3 day, 8±1% (P<0.001) and 5±1% (P<0.05) but did not affect edema formation.

Conclusion: Far infrared emitted by the bioceamics pad reduced mechanical and thermal hyperalgesia of inflammatory origin as well as paw temperature increase induced by intraplantar injection of CFA in mice.

Example 13: A Randomized Double Bind Placebo-Controlled Trial with a University Division I Soccer Team to Assess Physical Fitness Parameters Objective: To evaluate the effect of bioceramic imprinted practice uniforms on: respiratory capacity, back and leg muscle strength and cardiorespiratory fitness.

Design: A randomized double bind placebo-controlled trial involving 30 healthy Soccer Players. Each participant was randomized via manual draw to wear either a practice uniform comprising a bioceramic composition of Example 1 or a sham practice uniforms during regular practice sessions as well as a bioceramic or sham band throughout the day. Evaluations were conducted with both groups once a week for 4 consecutive weeks on pre-determined days before the beginning of the days practice.

Testing Methodology and Results (a) Respiratory Capacity

Respiratory capacity was evaluated with a spirometer (Model SP-10). The parameters evaluated were Forced Vital Capacity (FVC), Forced Expired Volume in one second (FEV1) and Peak expiratory flow (PEF). Forced vital capacity (FVC) is the volume of air that can forcibly be blown out after full inspiration, measured in liters. FVC is the most basic maneuver in spirometry tests. FEV1 is the volume of air that can forcibly be blown out in one second, after full inspiration. Peak expiratory flow (PEF) is the maximal flow (or speed) achieved during the maximally forced expiration initiated at full inspiration, measured in liters per minute.

(b) Back and Leg Muscle Strength

Back/leg dynamometer (Baseline, United States) was used to measure leg and back muscle strength. Using a pronated grip the participant held the device's handle bar and slowly straightened his legs up to their maximal level.

(c) Cardiorespiratory Fitness

Cardiorespiratory fitness was evaluated through the standardized 3-minute exercise test (pre-determined in conjunction with the Team's coach). The cardiorespiratory endurance index is derived from heart rate recovery after the test with the following formula: cardiorespiratory endurance index=duration of exercise (seconds)×100/sum of heart beats during the recovery period/2. The sum of heart beats during the recovery period is the sum of the heart rates during 3 periods after the test: 1 to 1.5 minutes, 2 to 2.5 minutes, and 3 to 3.5 minutes.

Conclusion: Results indicate that in all different parameters analyzed the athletes wearing bioceramics technology presented better overall results in comparison to the athletes that were wearing placebo gear.

Example 14: Effect of Far Infrared Emitted by Bioceramics on Clinical Measures of Physical Fitness Objective: To evaluate the effect of Far Infrared therapy emitted by bioceramics on flexibility, grip strength and respiratory capacity in a randomized double blind placebo controlled trial involving 9-12 Basketball Players of the Florida Atlantic University (ages 18-22).

Methods: Each participant was randomized to wear either a bioceramics shirt (bioceramics silkscreened shirt) containing bioceramic of Example 1 or a sham shirt (without bioceramics). Baseline evaluations were conducted on week 1. The players wore the jerseys three times a week during practice hours—from 9 am to 12 pm. Evaluations were conducted with both groups once a week for 3 consecutive weeks on Wednesdays during the first hour of the day's practice. In the second round of tests the groups were swapped. The group that was wearing the Sham BioPower Practice Uniforms was selected to wear BioPower shirts 7 days a week (throughout the day) and the group that was previously wearing BioPower uniforms stopped wearing the technology and served as control. Evaluations were conducted with both groups once a week for 3 consecutive weeks on Wednesdays during the first hour of the day's practice.

Flexibility was measured with the sit-and-reach test (Novel Flex-Tester® Sit & Reach Box). For evaluation each subject was asked to sit on the floor with knees flat against the floor and the box flat against the plantar aspect of his feet. Then the subject stretched out and reached towards the box and moved to distance indicator as far as possible. The mean of three measurements was used in the analysis.

The grip strength of the dominant hand was measured with a hand dynamometer a Baseline Smedley Digital Spring Hand Dynamometer with the subjects standing with their elbows extended. The mean score of three trials was recorded for analysis.

Respiratory capacity was evaluated with a spirometer (Model SP-10). The parameters evaluated were Forced Vital Capacity (FVC), Forced Expired Volume in one second (FEV1) and Peak expiratory flow (PEF). The best of three measurements was used in the analysis. Forced vital capacity (FVC) is the volume of air that can forcibly be blown out after full inspiration, measured in liters. Forced Expired Volume in one second (FEV1) is the volume of air that can forcibly be blown out in one second, after full inspiration. Peak expiratory flow (PEF) is the maximal flow (or speed) achieved during the maximally forced expiration initiated at full inspiration, measured in liters per minute.

Results: Flexibility.

Figure 3:
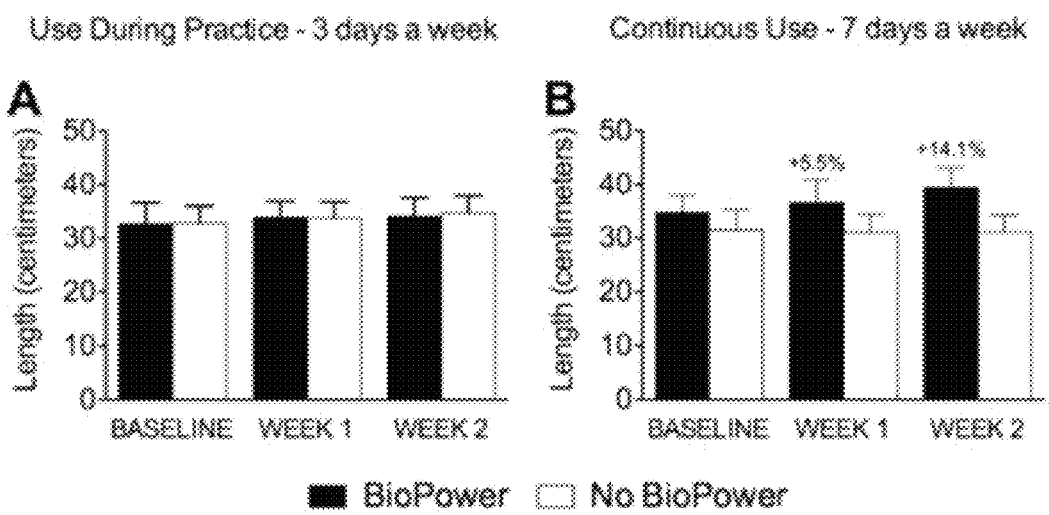
FIG. 3 is a graph illustrating a non-limiting example of effects of bioceramics of the instant disclosure on flexibility.
Figure 3:
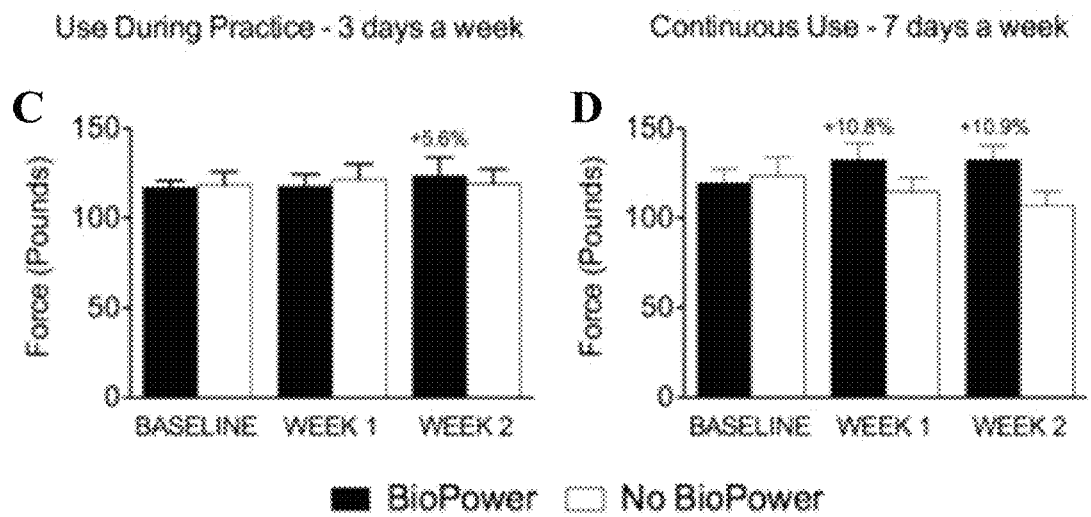

FIG. 3 is a graph illustrating a non-limiting example of effects of bioceramics of the instant disclosure on flexibility. In the first round of tests the use of a bioceramic did not affect Flexibility in comparison to baseline levels (FIG. 3, Panel A). In the second round of tests, in comparison to baseline levels, the use of the bioceramic technology increased Flexibility in 5.5% and 14.1% in the first and second week of continuous use, respectively. Flexibility was not affected in the group of athletes not wearing the technology (FIG. 3, Panel B). Grip Strength. In the first round of tests the use of the bioceramic increased Grip Strength in 5.6% on the second week of continuous use in relation to baseline levels. Control group Grip Strength was not altered from one evaluation to the other (FIG. 3, Panel C). In the second round of tests, in comparison to baseline levels, the use of the bioceramic technology increased Grip Strength in 10.8% and 10.9% in the first and second week of continuos use, respectively (FIG. 3, Panel D). On the other hand, in the group that consisted of athletes who were wearing the technology for 2 weeks (in the first round of tests) and discontinued its use, there was a decrease in Grip Strength of 7.23% and 13.51% in the first and second week of evaluations respectively (FIG. 3, Panel D).

Figure 4:
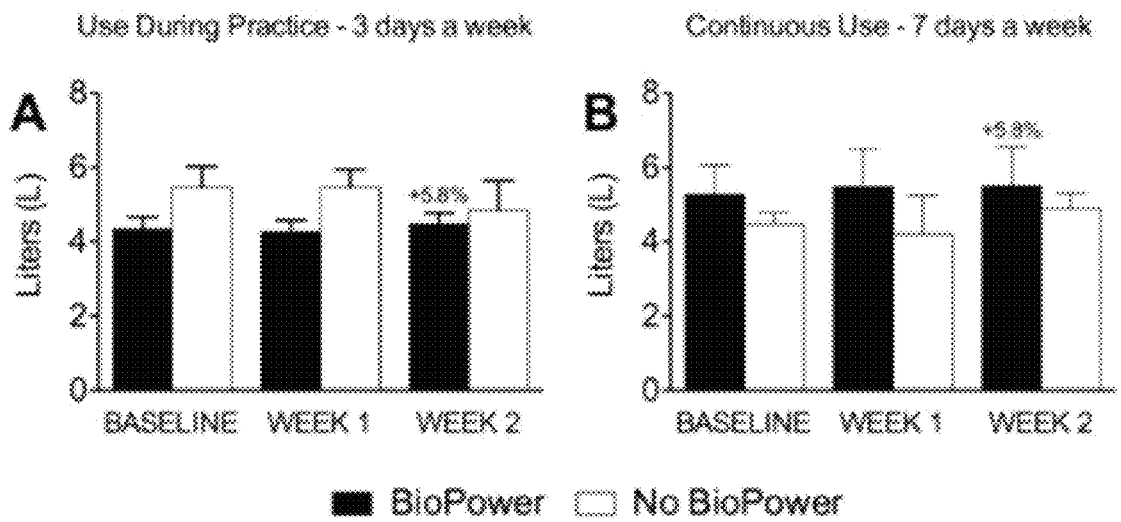
FIG. 4 is a graph illustrating a non-limiting example of effects of bioceramics of the instant disclosure on respiratory capacity.
Figure 4:
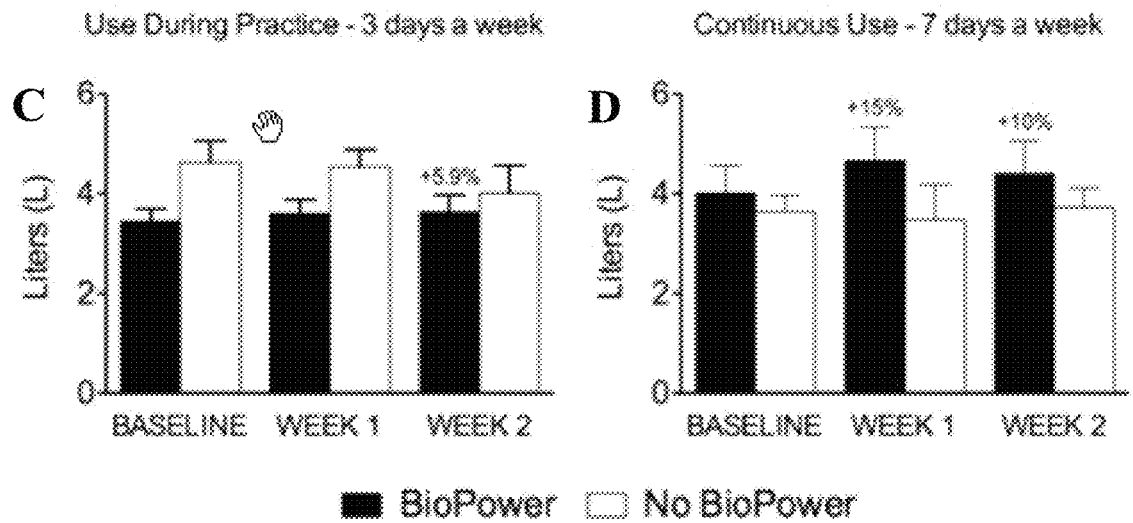
Figure 5:
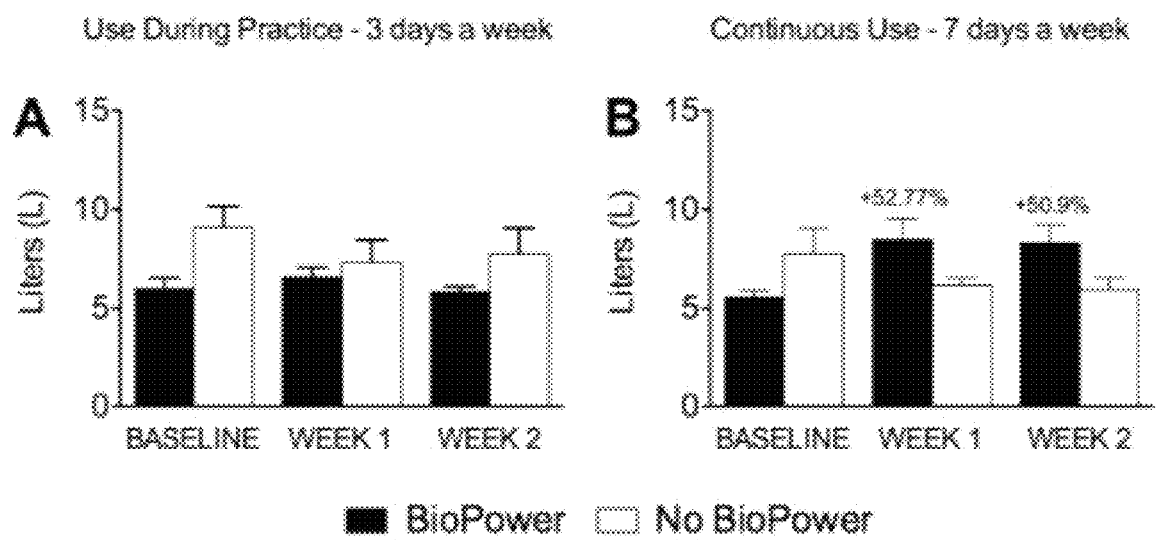
FIG. 5 is a graph illustrating a non-limiting example of effects of bioceramics of the instant disclosure on peak expiratory flow (PEF).

Respiratory Capacity. FIGS. 4 and 5 are graphs illustrating a non-limiting example of effects of bioceramics of the instant disclosure on respiratory capacity. FIG. 4 illustrates a non-limiting example of the effect of a bioceramic of the instant disclosure on forced vital capacity (FVC) and forced expired volume in 1 second (FEV1). FIG. 4 illustrates a non-limiting example of the effect of a bioceramic of the instant disclosure on peak expiratory flow (PEF). In the first round of tests the use of the bioceramic increased FVC (5.8%—FIG. 4, Panel A) and FEV1 (5.9%—FIG. 3, Panel C) but did not affect PEF (FIG. 5, Panel A) in comparison to baseline levels. Control group FVC, FEV1 and PEF decreased from one evaluation to the other (FIG. 4, Panels A and C, and FIG. 5, Panel A).

In the second round of tests, in comparison to baseline levels, the use of the bioceramic technology increased FVC (5.8% in the second week—FIG. 4, Panel B); FEV1 (15% and 10% in week one and two respectively—FIG. 4, Panel D) as well as PEF (52.77% and 50.9% in week one and two respectively—FIG. 5, Panel B). In the group that consisted of athletes who were wearing the technology for 2 weeks (in the first round of tests) and discontinued its use, FVC and FEV1 oscillated from one evaluation to the other (FIG. 4, Panels B and D, respectively), while PEF, on the other hand, decreased 19.7% in the first and 23.3% in second week of evaluations (FIG. 5, Panel B).

Conclusion: Far Infrared therapy emitted by bioceramics shirts increased flexibility, grip strength and respiratory capacity in healthy basketball players of the Florida Atlantic University. Continuous prolonged use induced the most significant results.

Example 15: Effect of Bioceramics Imprinted Apparel on Muscle Endurance and Cardiorespiratory Fitness in Athletes Objective: To evaluate the effect of bioceramics imprinted practice apparel (shirts and shorts) on muscle endurance and cardiorespiratory fitness.

Testing Methodology and Results: Each participant wore a bioceramics shirt/short during practice (3 times a week- 120 minute training session). In additional the participants wore a bioceramics shirt for 6-8 hours a day, 7 days a week. Evaluations were conducted once a week on Mondays.

(a) Muscle Endurance

Muscle endurance was measured with the push-up test. The subjects were asked to (1) lie prone on floor with hands slightly wider than shoulder width then (2) raise body up off floor by extend arms with body straight. The maximum number of sit-ups performed until exhaustion was used to represent muscle endurance.

Figure 6:
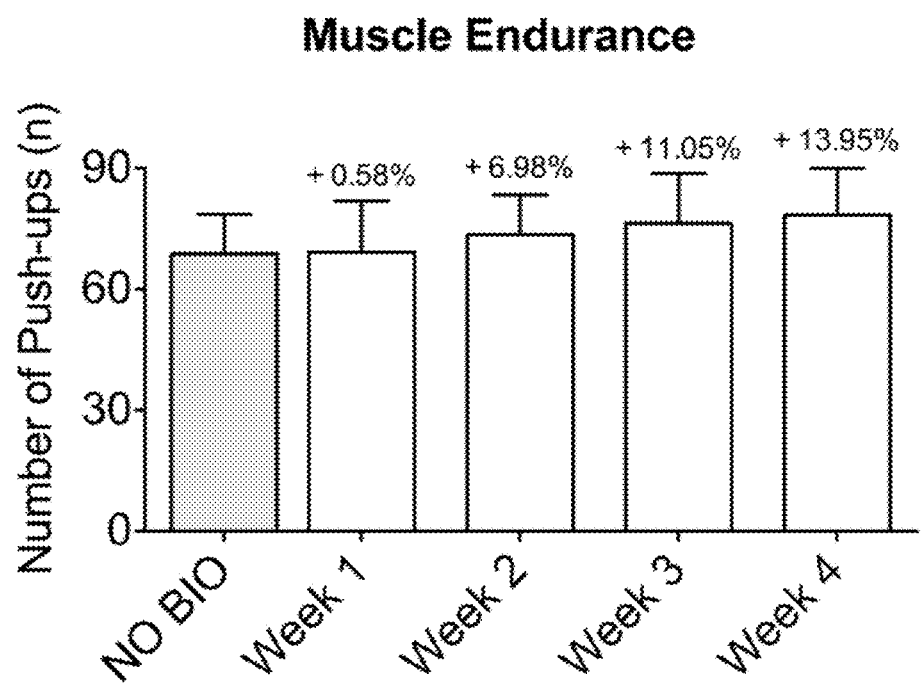
FIG. 6 illustrates a non-limiting example of effects of bioceramics of the instant disclosure on muscle endurance.

FIG. 6 illustrates the effect of bioceramics on muscle endurance of humans. Data depicted in FIG. 6 demonstrate that there has been a gradual increment in the maximum number of push-ups performed by the athletes. Best increment in comparison to evaluation conducted without the use of bioceramics was obtained in week n#4 (13.95%). FIG. 6 illustrates the results of an experiment where N=5. Numbers above bar indicate increase in comparison to "No Bio-Power" week control.

(b) Cardiorespiratory Fitness

Figure 7:
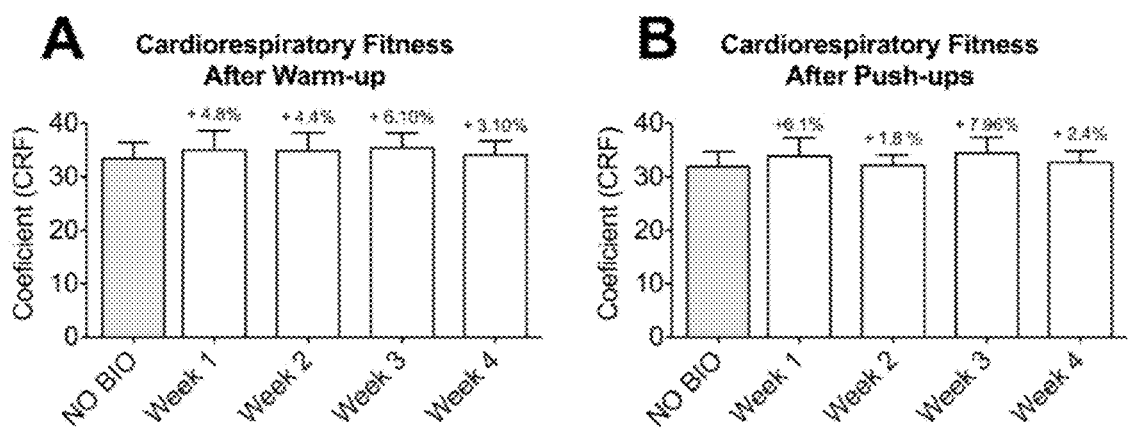
FIG. 7 illustrates a non-limiting example of effects of bioceramics of the instant disclosure on cardiorespiratory fitness.

Cardiorespiratory fitness was evaluated through a standardized test with minor variations. The cardiorespiratory endurance index is derived from heart rate recovery after the test with the following formula: cardiorespiratory endurance index=duration of exercise (seconds)×100/sum of heart beats during the recovery period/2. The sum of heart beats during the recovery period was the sum of the heart rates during 3 periods after the test: 1 to 1.5 minutes, 2 to 2.5 minutes, and 3 to 3.5 minutes.[2] Two evaluations were conducted: the first after a 10-minute warm-up session and the second after the 1-minute push-up test described in item 3.2. The standardized 3-minute time was used in the calculations in order to normalize the results of both tests to facilitate comparisons. FIG. 7 illustrates the effect of bioceramics on cardiorespiratory fitness of humans. FIG. 7 illustrates the results of an experiment where N=5. FIG. 7, panel A illustrates the results of an evaluation conducted after warm-up session. FIG. 7, panel B illustrates the results of an evaluation conducted after push-up session. Numbers above bar indicate increase in comparison to "No Bio-Power" week control.

Results presented in FIG. 7 indicate that the use of bioceramics increased cardiorespiratory index in all evaluations conducted both after warm-up (FIG. 7, panel A) and push-up sessions (FIG. 7, panel B). Maximum increment in comparison to evaluation conducted without the use of bioceramics occurred on week n#3 (6.10% and 7.69%).

Conclusion: Results indicate that the use of bioceramics imprinted apparel helped increase muscle endurance and cardiorespiratory fitness of 5 MMA fighters.

Example 16: Effect of Bioceramics Paint on CFA Induced Mechanical Hypersensitivity Objective: The use of bioceramic paint containing the composition of Example 1 on CFA induced mechanical hypersensitivity was evaluated.

Methods: Experiments were conducted using adult male Swiss mice weighing 25-35 g, housed at 22° C. under a 12-h light/12-h dark cycle (lights on at 06:00), with access to food and water ad libitum. The experiments were performed after approval of the protocol by the Ethics Committee of the Universidade do Sul de Santa Catarina (UNISUL). The animals (n=8) underwent intraplantar injection (right hind paw) of a solution containing 20 μl of Freud's complete adjuvant (CFA, 70%). For treatment a bioceramics paint (10 and 20% concentration) was applied to the bottom of the animals' box. After 24 h of exposure mechanical nociceptive threshold was assessed as response frequency to 10 presentations of a 0.4 g von frey filament applied to the animals right hind paw. Evaluations were also conducted on days 2 and 3 post CFA injection.

Figure 8:
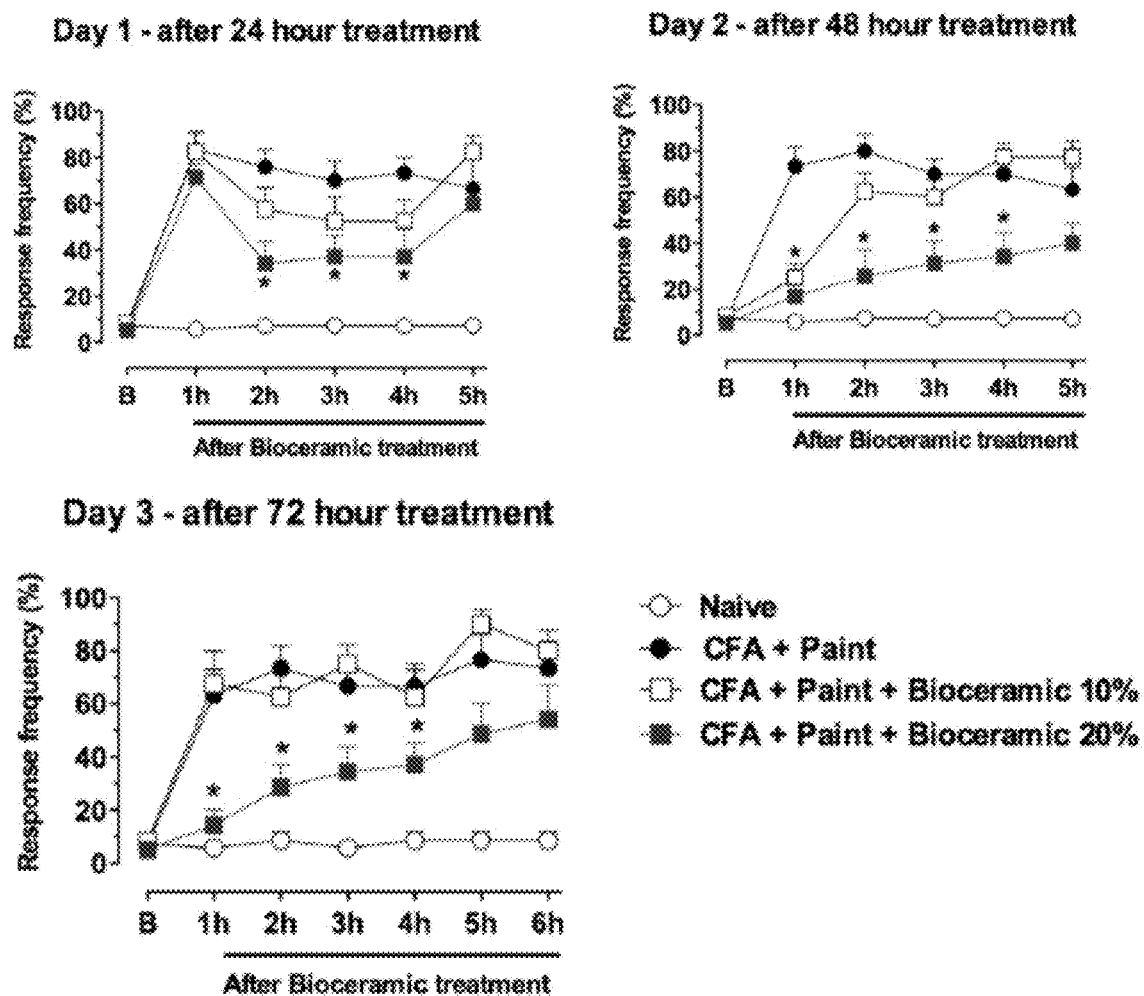
FIG. 8 illustrates a non-limiting example of effects of bioceramic paint on CFA induced mechanical hypersensitivity.
Figure 9:
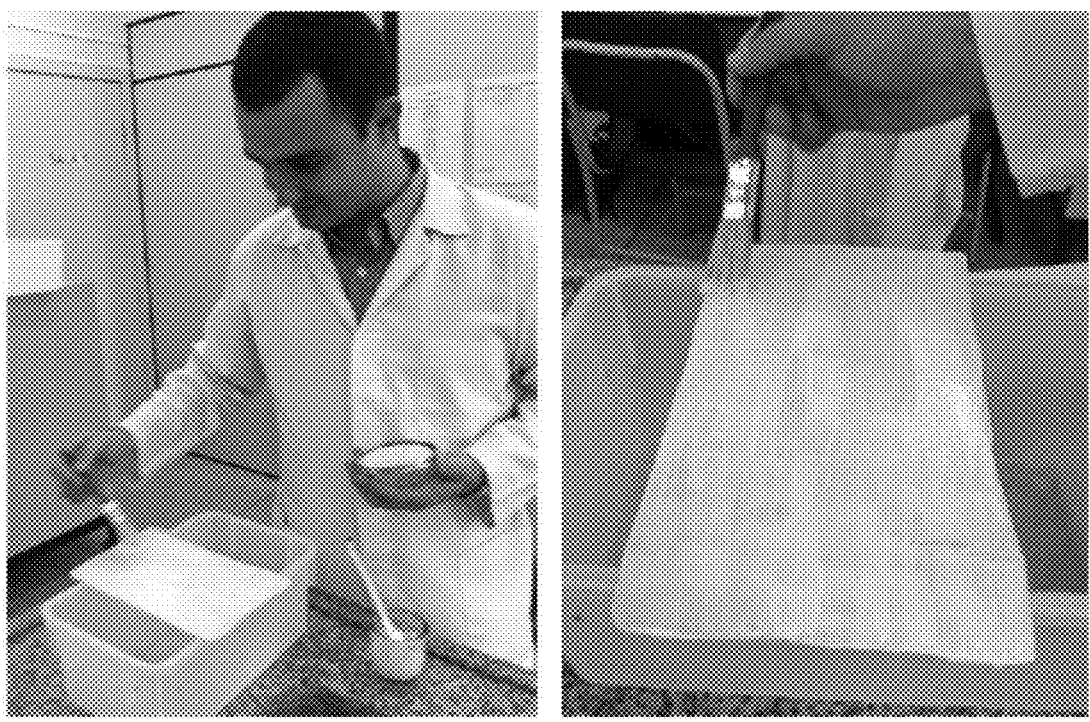
FIG. 9 illustrates a non-limiting example of a bioceramic paint of the instant disclosure.

Results: The results show that the i.pl. injection of CFA induced mechanical hypernociception (P<0.001) which was significantly reduced by exposure to the bioceramic paint (20 but not 10% bioceramic concentration) applied to the bottom of the animals' box. Effect lasted for up to 4 hours (day 2 and 3). FIG. 8 illustrates the effects of bioceramic paint on CFA induced mechanical hypersensitivity. Evaluation of 8 individuals, the vertical lines indicate the S.E.M. *p<0.05. FIG. 9 illustrates a bioceramic paint.

Conclusion: Bioceramic paint reduced mechanical hypersensitivity induced by CFA paw injection.

Example 17: Far Infrared Emitted by Ceramic Materials Increases Paw Temperature and Reduces Mechanical Hypersensitivity and Knee Edema in a Rat Model of Monoiodoacetate-Induced Osteoarthritis Objective: This study investigated the effect of far infrared emitted by ceramic materials on skin temperature, paw mechanical hypersensitivity and knee edema in a rat model of monoiodoacetate (MIA)-induced osteoarthritis.

Methods: Experiments were conducted with male Winsar rats (200-250 g) anesthetized with a mixture of ketamine and xylazine (50 and 10 mg/kg, respectively, i.p.). Joint damage was induced by a single intra-articular injection of MIA (1 mg/50 μl; Sigma UK—which disrupts glycolysis resulting in chondrocyte death) through the infrapatellar ligament of the right knee. Control animals received a single injection of saline (50 μl). Three separate measures were assessed: (1) thermal analyses of the central areas of the front paws of the animals (with a portable ThermaCAM® E320 infrared camera—Flir, Sweden—with a 320×240 pixels resolution, thermal sensitivity of <0.10° C. at 25° C. and accuracy of ±2° C.—positioned 0.5 m away from the animals paws. The infrared images were analyzed with the FLIR QuickReport 1.2 software); (2) hind paw mechanical withdrawal thresholds (using von Frey monofilaments—Semmes-Weinstein monofilaments of bending forces 1-15 g), which provide an index of central sensitisation; and (3) edema formation (measured with a digital caliper—Pantec, Brazil), which is directly associated with the localized inflammatory response. For treatment a bioceramics pad containing the bioceramic of Example 1 (80% BioCorn PVC—20% ceramic materials) was placed inside the animals box; control animals were placed on a Sham Pad (100% BioCorn PVC without ceramics) and underwent the same experimental protocol.

Results: On day 3 post-MIA injection acute exposure (2 hours) to the bioceramics pad increased paw temperature (±4° C.), although only chronic exposure to the treatment (Day 7 and 10 post-MIA) reduced mechanical hypersensitivity (p<0.001) and knee edema (p<0.001).

Conclusion: Far infrared emitted by ceramic materials increased paw temperature (after acute exposure) whereas only prolonged treatment reduced mechanical hypersensitivity and knee edema in a rat model of MIA-induced osteoarthritis.

Example 18: Far Infrared Emitted by Bioceramics Reduced Hypernociception of Inflammatory Origin in Mice Objective: The aim of this study was to evaluate the effect of far infrared radiation emitted/reflected by bioceramics in a pad containing the bioceramic of Example 1 on pain of inflammatory origin as well as on paw temperature increase and edema formation in an experimental model of inflammation in mice.

Methods: Experiments were conducted using adult male Swiss mice weighing 25-35 g, housed at 22° C. under a 12-h light/12-h dark cycle (lights on at 06:00), with access to food and water ad libitum. The experiments were performed after approval of the protocol by the Ethics Committee of the Universidade do Sul de Santa Catarina (UNISUL). The animals (n=8) underwent intraplantar injection (right hind paw) of a solution containing 20 µl of Freud's complete adjuvant (CFA, 70%). For treatment a bioceramics pad was placed inside the animals box. After 24 h of exposure to the product, mechanical nociceptive threshold was assessed as response frequency to 10 presentations of a 0.4 g von frey filament applied to the animals right hind paw. The evaluations were performed daily for 10 days—after each evaluation, the animals were put back in their boxes and re-exposed to the Pad until the subsequent evaluation (24 hours). In addition, the volume (edema formation) and the temperature of the right hind paws were evaluated on experimental days 1, 3 and 10 with a Pleithsmometer and a digital thermometer respectively. Control animals were placed on a sham pad—consisting of 100% BioCorn PVC (without bioceramics) and underwent the same experimental protocol.

Results: The results show that the i.pl. injection of CFA induced mechanical hypernociception (P<0.001) which was significantly reduced by acute exposure to the bioceramics pad containing bioceramic of Example 1. The analgesia lasted for up to 2 hours with peak effect 30 min after treatment (P<0.001—maximum inhibition of 53±11%). Chronic treatment with the bioceramic pad reduced mechanical hypernociception on all evaluation days. In addition, the treatment significantly decreased paw temperature on days 1 and 3 day, 8±1% (P<0.001) and 5±1% (P<0.05) respectively, when compared with the control group.

Conclusion: The bioceramics pad reduced mechanical hypernociception of inflammatory origin as well as the increase of paw temperature induced by intraplantar injection of CFA in mice.

Example 19: Uses of Bioceramics Emitting Far Infrared Energy in the Treatment of Human Conditions A bioceramic emitting far infrared energy is used to modulate or treat one or more of the following: pain, muscle endurance, stamina, muscle strength, cardiorespiratory fitness, respiratory capacity, flexibility, cellular metabolism, analgesia, cellular oxidation, fibromyalgia, inflammation, oxidative stress, blood circulation, intolerance to cold environments, arthritis or vascular disease, cutaneous perfusion, arrhythmia, high blood pressure, tissue injury, an esthetic effect such as a reduction in cellulite of the subject, an improvement in the quality of life.

Methods: a subject wears an apparel of the disclosure comprising a bioceramic for at least 6 weeks. The following parameters or endpoints, alone or in combination, are used to measure the effects of articles of clothing impregnated with an infrared emitting ceramic material(s) in the treatment of human subjects with a condition disclosed herein:
a) quality of life, sleep patterns, depression and anxiety;
b) pain, muscle strength, and flexibility;
c) balance and distribution of the standing pressure;
d) stress (measured by activity of the autonomous, sympathetic, and parasympathetic nervous systems;
e) body surface temperature;
f) inflamatory mediators (anti- and pro-inflamatory cytokines); or
g) oxidative stress and antioxidant systems.

Figure 10:
FIG. 10 illustrates a non-limiting example of a pad comprising a bioceramic of the instant disclosure.
Figure 11:
FIG. 11 illustrates a non-limiting example of a bracelet comprising a bioceramic of the instant disclosure.

Bioceramic Treatments: t-shirts or pads impregnated with an infrared emitting bioceramic material of the BioPower® brand or control T-shirts are distributed between groups. Patients are instructed to wear the apparel comprising the ceramic materials during the day, at night, or during their sleep. Treatment is conducted for about three consecutive months. FIG. 10 illustrates a human subject wearing exemplary t-shirts or pads comprising a ceramic of the disclosure.

Endpoints: some of the following endpoints, alone or in combination, are used to quantify an efficacy of a bioceramic material in a subject: a) evaluation of grip strength; b) flexibility evaluation; c) thermography; d) evaluation of pro-inflammatory and anti-inflammatory cytokines; e) evaluation of antioxidants, evaluation of markers of oxidative stress, or f) questionnaires.

Evaluation of Grip Strength: a dynamometer is used as an instrument for the assessment of grip strength. The principle of operation of the dynamometer relies in the deformation undergone by a spring due to the action of a force. The intensity of the force is graded, so the dynamometer is a useful method for the measurement of force of some subjects. The dynamometer is particularly useful to measure the intensity of force in, for instance, human subjects afflicted with fibromyalgia, since the dynamometer measurements take into account the common and predominant muscle fatigue in the upper limbs (UL) and in the appendicular skeleton as compared to the axial upper limb studies.

Flexibility Evaluation: flexibility evaluation is measured with the Third Finger-Soil test. The instrument measures the overall flexibility of a subject with regards to subject standing flexibility, the ability of a subject to hold their feet together, and the maximum flexibility of the trunk of a subject without flexing their knees. This measurement is conducted on subjects with relaxed heads and the distance between the ground and the third toe is measured with a tape measure, on either the right or left side. A subject that is capable of touching the ground is considered a subject with good flexibility.

Thermography Evaluation: thermography is a useful technique in the analysis of hyper-radiating points in the infrared image, as it allows for the detection of thermography images in the surface skin of a subject, such as the skin of the human body. The technique is optionally performed on a human subject that is standing up and undressed, with the arms extended alongside the body but not touching the body. The temperature is maintained at about 20° C. throughout the procedure. Prior to capturing the image, the subjects are asked to rest for 15 minutes to allow for the body temperature to become acclimated to the controlled room temperature.

Evaluation of Proinflammatory and Anti-Inflammatory Cytokines: Blood samples are collected and prepared for analysis by centrifugation (IL-10, IL-6, IL-1βe TNF-α). The serum is processed for cytokine analysis. The serum may optionally be kept frozen at 80° C. for up to one year. The serum is analyzed by immunoassay (pg/dL) (Sandwich ELISA) using commercial kits and the concentration of cytokines is determined. One of skill in the art will appreciate that other methods known in the art can optionally be used to evaluate levels of proinflammatory and anti-inflammatory cytokines.

Evaluation of Antioxidants and Determination of Oxidative Stress:
a) substances reactive to thiobarbituric acid-TBARS: to determine the effects of bioceramics on the modulation of oxidative stress a sample comprising serum lipids is collected from a subject. The sample is analyzed by heating it in an acid reaction by TBARS. (Esterbauer, H., Cheeseman, K. H. Determination of aldehydic lipid peroxidation products: malonaldehyde and 4-hydroxynonenal. Methods Enzymol, v. 186, p. 407-421, 1990). Briefly, serum is mixed with 1 mL of 10% trichloroacetic acid and 1 mL of 0.67% thiobarbituric acid and is subsequently placed in a boiling water bath for 15 min. Absorbance at 535 nm is measured using 1,1,3,3-tetramethoxypropane as external standard. The results are calculated and presented as malondialdehyde equivalents per milligram of protein. One of skill in the art will appreciate that other methods known in the art can optionally be used to evaluate levels of oxidative stress in a sample.

b) protein carbonylation: the effect of oxidative stress on proteins is evaluated based on the reaction of carbonyl groups with dinitrophenylhydrazine (Levine et al., 1990) (Levine, R. L.; Garland, D.; Oliver, C. N.; Amici, A.; Climent, I.; Lenz, A. G.; Ahn, B. W.; Shaltiel, S.; Stadman, E. R. Determination of carbonyl content in oxidatively modified proteins. Methods Enzymol, v. 186, p. 464-478, 1990; incorporated by reference herein). Briefly, the proteins are first precipitated with the addition of 20% trichloroacetic acid and dissolved in dinitrophenylhydrazine, and then the absorbance is measured at 370 nm. The results are expressed as levels of protein carbonyls by milligram of protein. One of skill in the art will appreciate that other methods known in the art can optionally be used to evaluate levels of protein carbonylation.

c) extent of oxidative damage in the sulfyhydryl group of proteins: oxidative damage of proteins is analyzed by characterizing damage to the sulfhydryl groups (previously described by: Aksenov et al. (Aksenov, M. Y., Markesbery, W. R. Changes in thiol content and expression of glutathione redox system genes in the hippocampus and cerebellum in Alzheimer disease. NeurosciLett, v. 302, p. 141-145, 2001). Briefly, the proteins in the sample are precipitated and dissolved in dithionitrobenzoic acid. Absorbance is measured at 412 nm. The results are expressed as levels of TNB per milligram protein. One of skill in the art will appreciate that other methods known in the art can be used to evaluate levels of oxidative damage in the sulfyhydryl group of proteins.

d) antioxidant activity of enzymes: the activity of catalase (CAT) is determined by measuring the decrease in the absorbance of hydrogen peroxide at 240 nm. The data is plotted as units per milligram of protein. The activity of superoxide dismutase (SOD) is determined by the inhibition of auto-oxidation of adrenaline measured spectrophotometrically at 480 nm (described by Bannister, J. V.; Calabrese, L. Assays for superoxide dismutase. Methods Biochem Anal, v. 32, p. 279-312, 1987) and expressed as activity units per milligram of protein. One of skill in the art will appreciate that other methods known in the art can be used to evaluate enzyme activity levels.

e) determination of total protein: all biochemical measurements can be normalized by protein content with bovine serum albumin as standard with for example, the methods describe by Lowry, Rosebrough, and Farr (Lowry, O. H.; Rosebrough, N. J.; Farr, A. Protein measurement with the Folin phenol reagent. J Biol Chem, v. 193, p. 265-275, 1951).

The subject benefits from at least one of the following by using an apparel of the disclosure: a reduction in pain, an increase in muscle endurance, an increase in stamina, an increase in muscle strength, a modulation of the cardiorespiratory system, such as an increase in respiratory capacity, an increase in flexibility, a modulation of cellular metabolism, an improvement of analgesia, an anti-oxidative effect, an anti-fibromyalgia effect, a decrease in inflammation, a decrease in oxidative stress, a modulation of cytokine levels, a modulation of blood circulation, a reduction in intolerance to a cold environment, a reduction in a symptom of arthritis or vascular disease, an increase in cutaneous perfusion, a decrease in heart rate, a decrease in blood pressure, quicker recovery from injury or exercise, an esthetic effect such as a reduction in cellulite of the subject, an improvement in the quality of life.

Example 20: Uses of Bioceramics Emitting Far Infrared Energy in the Treatment of Human Fibromyalgia Fibromyalgia is a painful chronic condition, usually accompanied by diverse symptoms and preponderantly affecting the musculoskeletal system. 2.5% of the Brazilian population is afflicted with Fibromyalgia. According to recent epidemiological data, approximately 2% of the world population is affected by Fibromyalgia. The principal symptoms of fibromyalgia are associated with persistent pain lasting longer than three months, disruptions in sleep, fatigue, anxiety, paresthesia, headaches, and tender points. There is an ongoing debate regarding the underlying causes of fibromyalgia, however studies have raised the possibility that fibromyalgia is related to genetic causes, trauma, infections, stress.

Objective: this study evaluates the effects articles of clothing impregnated with an infrared emitting ceramic material(s) (bioceramic) as compared to aquatic exercises in the symptoms and prognosis of patients diagnosed with fibromyalgia.

Study Design: the present research is based in a blind randomized clinical study. It is designed to adequately compare the efficiency of distinct treatments; patients are randomly distributed within groups to avoid systematic errors. Individuals are randomized as follows (n=25 per group): Group 1: control group, is not treated with hydrokinesiotherapy or bioceramic; Group 2: is treated with bioceramic materials only; Group 3: is treated with hydrokinesiotherapy only; Group 4: is treated with both hydrokinesiotherapy and bioceramic.

Hydrokinesiotherapy Treatment: exercises previously described by Berti et al (2008) (BERTI, Gabriela et al. Hidroterapia Aplicada ao tratamento de Fibromialgia: avaliação clínica e laboratoriais de pacientes atendidos no Centro Universitário Feevale em Nova Humburgo—RS. Revista digital de Educación Física y Desportes. n. 122, 2008; incorporated herein by reference) are conducted, for instance, in the temperature controlled swimming pool of the UNISUL Aquatic Complex. Alternatively, exercises can be conducted in any suitable pool.

Exercises are conducted in four phases encompassing 36 sessions of 1 hour each, three times a week per group. During the first phase there can be a global warm-up following a straight line along the extension of the pool, moving forwards and laterally. The second phase can last approximately 15 minutes and can include active stretching of superior and inferior muscles, sustained for consecutive 20 second intervals. The duration of the exercises in the third phase is about 20 minutes, and the exercises are designed to be relatively free of activity in superior and inferior body members. Finally, the fourth phase can consist of relaxing exercises characterized by oscillatory movements, conducted under the supervision the physiotherapist.

Conclusion: one or more of the endpoints/parameters described in Example 19 are used to determine an efficacy of a bioceramics emitting far infrared energy in the treatment of human fibromyalgia. The hypothesis is that a ceramic of the disclosure is effective in the treatment of humans with fibromyalgia.

Example 21: Randomized, Placebo-Controlled Trial to Test the Efficacy of a Bioceramic as an Adjuvant to Physical Therapy in the Treatment of Chronic Low Back Pain in Humans Low back pain (LBP) is a common complaint in today's society and is a significant cause of discomfort in adults younger than 45 years old. Debilitating back pain that continues for more than 3 months is considered chronic. Chronic low back pain (CLBP) has many causes, which are treated with diverse methods, such as bed rest, lumbar support devices, traction, thermotherapy, electrical stimulation, and manipulation in most cases. Invasive treatment methods, such as surgery, selective nerve root block and epidural injection, can be used to treat chronic back pain.

Objective: the aim of this study is to evaluate the effect of an apparel of the disclosure comprising a bioceramic that emits far infrared energy reflecting bioceramics to treat chronic back pain.

Methods: the study is designed as a controlled clinic trial to test the efficacy of a far-infrared emitting ceramic sleeve or patch as an adjuvant to physical therapy treatment of chronic low back pain.

Intervention: subjects will follow a regular physical therapy (PT) regimen treatment at the Wilfred R. Cameron Wellness Center clinic in Washington, Pa. Subjects will be randomly divided into 3 (three) experimental groups:
  a) control: receives PT treatment only.
  b) bioceramic patch: receives PT treatment and uses a bioceramic patch for "n" hours after the treatment.
  c) placebo: receives PT treatment and uses a placebo patch (without bioceramics) for "n" hours after the treatment hours after the treatment.

Evaluation of Pain and Disability Level: The Oswestry Back Pain Disability Index (ODI); the Roland-Morris Low Back Pain and Disability Questionnaire and the "Backache Index" (BAI) will be used to evaluate pain levels. The hypothesis is that a patch of the disclosure will be effective in the treatment of humans with chronic back pain.

Figure 2:
FIG. 2 illustrates a non-limiting example of a shirt and a pad comprising a bioceramic of the instant disclosure

Example 22: Uses of Bioceramics Emitting Far Infrared Energy in the Treatment of Human Pain A subject with chronic back pain wears a pad of the disclosure. The efficacy of the pad has been evaluated in a study described in Example 21 or another suitable study. An exemplary pad for the treatment of chronic back pain is the pad shown in FIG. 2 worn as shown in FIG. 10, either vertically or horizontally.

Intervention: the subject with chronic back pain wears the pad daily for about 6 consecutive weeks for 7 consecutive days. The pad provides an amount of infrared energy to the subject. The amount of infrared energy received by the subject is as follows (far infrared wavelength between 9 and 10 micrometers):
Fabric silkscreened with ink at a 50% bioceramic concentration: irradiance of 4.05 milliW/cm$^2$ at a body temperature of 36.5° C. provides about 2.43 J/cm$^2$ per hour of use.
Fabric silkscreened with ink at a 30% bioceramic concentration: irradiance of 3.65 milliW/cm$^2$ at a body temperature of 36.5° C. provides about 2.19 J/cm$^2$ per hour of use.

The treatment provides relief to the subject with chronic back pain.

The subject wants to prolong the relief from chronic back pain. The subject optionally consults his physician or physical therapist to discuss treatment regimens and options. The subject adjusts the treatment regimen to prolong the feeling of relief by wearing the patch for longer periods of time. The subject experiences prolonged relief to chronic back pain.

Example 23: Uses of Bioceramics Emitting Far Infrared Energy in the Treatment of Human Carpal Tunnel Syndrome Carpal tunnel syndrome (CTS) is an entrapment neuropathy, which is caused mainly by median nerve compression and irritation at the level of carpal tunnel. Its symptoms include pain and paraesthesia in the wrist and hand that can radiate to the forearm. CTS affects 1% to 3% of population, with higher incidence in certain occupational groups who perform repetitive motions of the hand and wrist.

Objective: the aim of this study is to evaluate the effect of an apparel of the disclosure comprising a bioceramic that emits far infrared energy reflecting bioceramics to treat carpal tunnel syndrome.

Methods: Randomized, placebo-controlled pilot clinic trial to test the efficacy of a far-infrared emitting ceramic sleeve as an adjuvant to physical therapy treatment of carpal tunnel syndrome.

Intervention: subjects will follow a regular physical therapy (PT) regimen treatment at the Wilfred R. Cameron Wellness Center clinic in Washington, Pa. Subjects will be randomly divided into 3 (three) experimental groups:
  a) control: receives PT treatment only.
  b) bioceramic sleeve: receives PT treatment and uses a bioceramic patch for "n" hours after the treatment.
  c) placebo: receives PT treatment and uses a placebo sleeve (without bioceramics) for "n" hours after the treatment hours after the treatment.

Endpoints Measured: 1) Evaluation of pain and disability level: The Boston Carpal Tunnel Syndrome Questionnaire will be used to determine the efficacy of a sleeve of the disclosure in the treatment of carpal tunnel syndrome; and 2) Evaluation of grip strength (muscle strength): The grip strength of the affected dominant hand will be measured with a Digital Spring Hand Dynamometer (Baseline Smedley, USA) with the subjects standing with their elbows extended. The hypothesis is that a sleeve of the disclosure will be effective in the treatment of humans with carpal tunnel syndrome.

Example 24: Uses of Bioceramics Emitting Far Infrared Energy in the Treatment of Human Inflammation Objective: the aim of this study will be to evaluate the effect of apparel of the disclosure, such as a shirt, a sleeve, or a pad, comprising a bioceramic that emits far infrared energy reflecting bioceramics for the treatment of inflammation.

Methods: the study will be designed as a controlled clinic trial to test the efficacy of a far-infrared emitting ceramic sleeve or patch as an adjuvant to treat inflammation in humans, such as joint inflammation of humans with arthritis.

Study type: interventional. Subjects will be randomly divided into 3 (three) experimental groups:
a) group 1: receives no treatment.
b) group 2: wears an apparel of the disclosure: a shirt, a pad, or both, for "n" hours after the treatment.
b) group 3: wears a control apparel that does not comprise any bioceramic, for "n" hours after the treatment.

Endpoint Classification: the efficacy of the bioceramics in treating inflammation will be determined based on the expression of the following cytokines: either individually or as a group: TNF-α, IL-1β, IL-10 and IL-6. The absorbance for the aforementioned cytokines will be measured using a microplate reader at 450 and 550 nm. Cytokine levels of humans will be used to confirm the anti-inflammatory effect of the bioceramic compositions.

Figure 12:
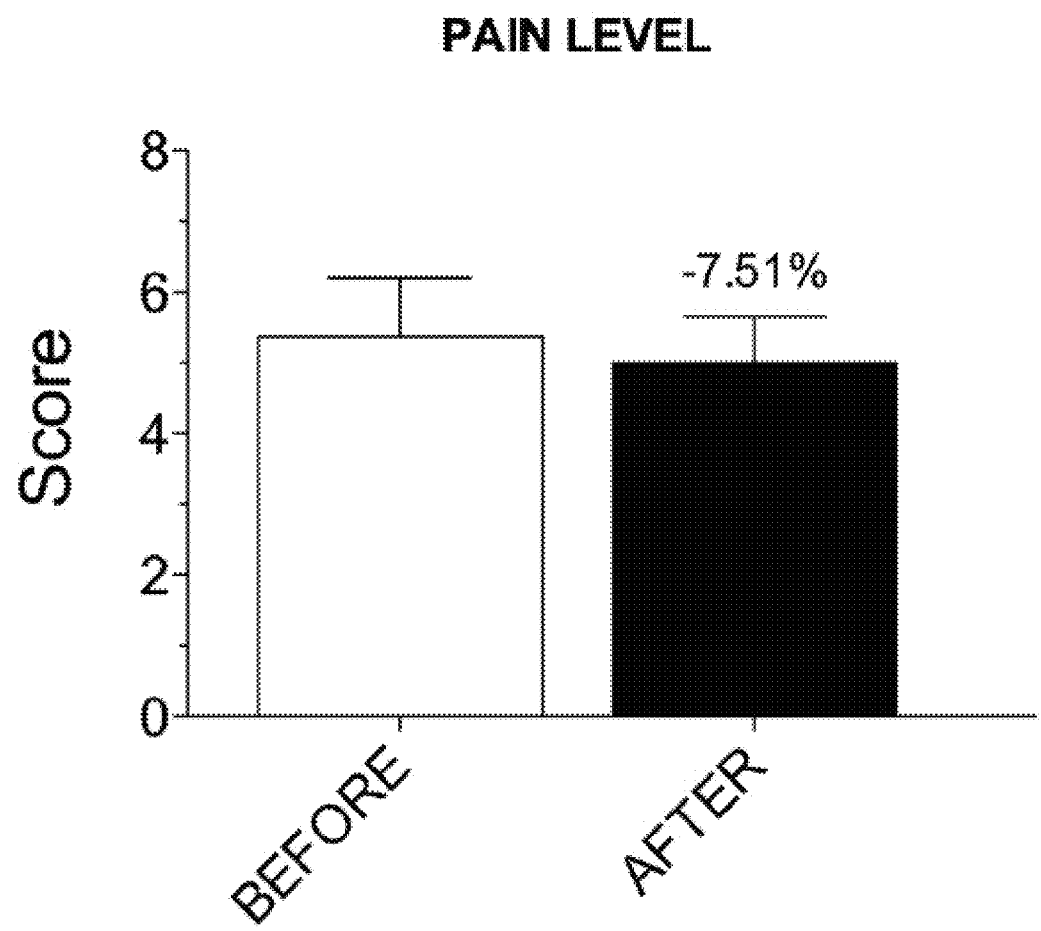
FIG. 12 is a graph illustrating a non-limiting example of a self-reported reduction of greater than 7.5% overall pain levels in human subjects treated with an apparel of the instant disclosure.

Example 25: Self-Reported Levels of Overall Pain, Overall Health Levels, Overall Fatigue, Overall Quality of Sleep, and Overall Performance Levels of Humans Participating in a Zumba Fitness Program An online questionnaire was used to assess the impact of bioceramic materials in subjects participating in a Zumba fitness program (ZUMBA®). Subjects were asked to identify how many times a week they practiced Zumba. Subjects taking zumba classes were selected for further analysis. 10 subjects were asked to answers the following questions:

1) "How would you rate your overall pain level the past 2 weeks? Check the number that best describes your pain. 1=no pain 10=worst." FIG. 12 is a graph illustrating a self-reported reduction of greater than 7.5% overall pain levels in human subjects treated with an apparel of the disclosure.

Figure 13:
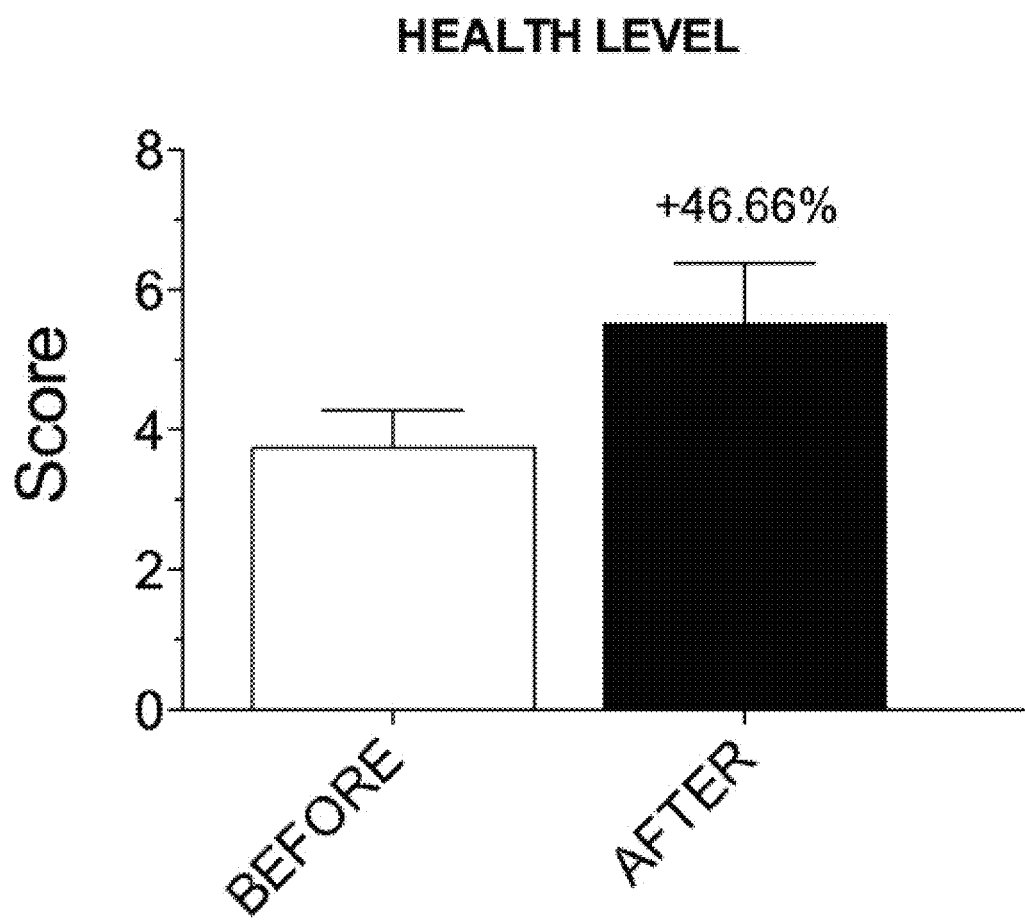
FIG. 13 is a graph illustrating a non-limiting example of a self-reported improvement of greater than 46% overall health levels of human subjects treated with an apparel of the instant disclosure.

2) "How you rate your overall health level the past 2 weeks? Check the number that best describes your overall health level 1=really good 10=really bad." FIG. 13 is a graph illustrating a self-reported improvement of greater than 46% overall health levels of human subjects wearing a shirt of the disclosure while exercising in a Zumba fitness program.

Figure 14:
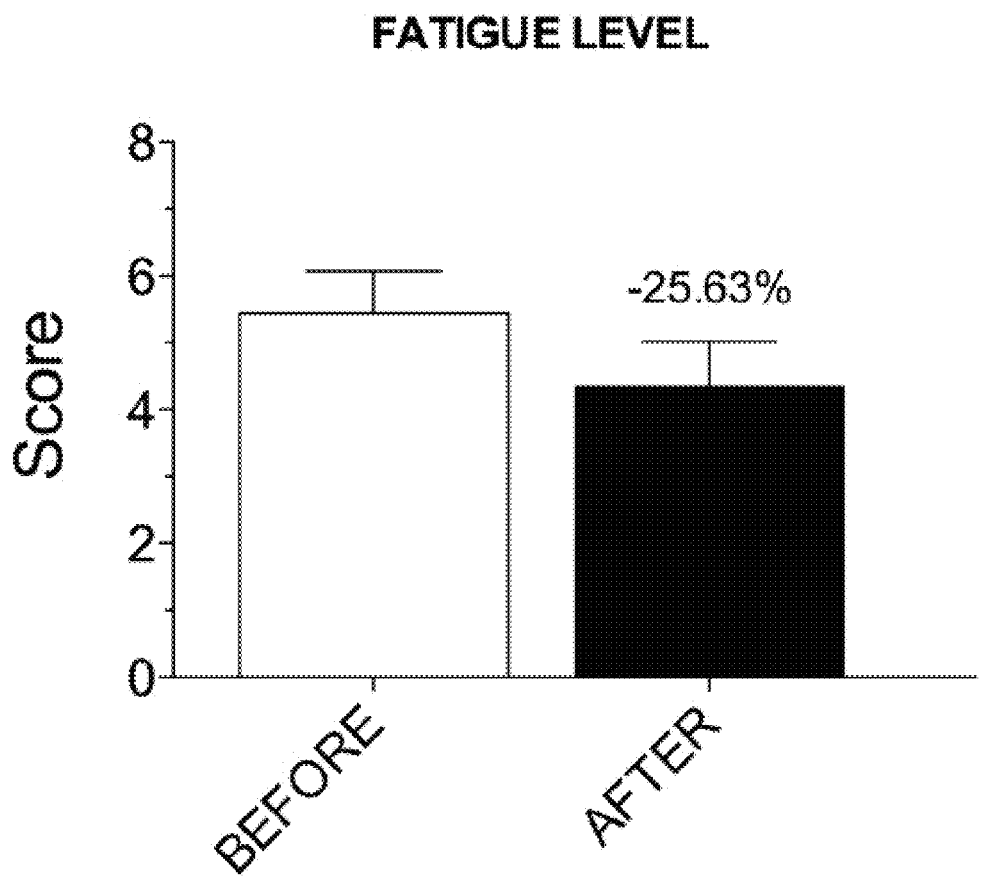
FIG. 14 is a graph illustrating a non-limiting example of a self-reported reduction of greater than 25% overall fatigue levels in human subjects treated with an apparel of the instant disclosure.

3) "How would you rate your overall fatigue level the past 2 weeks? Check the number that best describes your overall fatigue 1=really good 10=really bad." FIG. 14 is a graph illustrating a self-reported reduction of greater than 25% overall fatigue levels in human subjects wearing a shirt of the disclosure while exercising in a Zumba fitness program.

Figure 15:
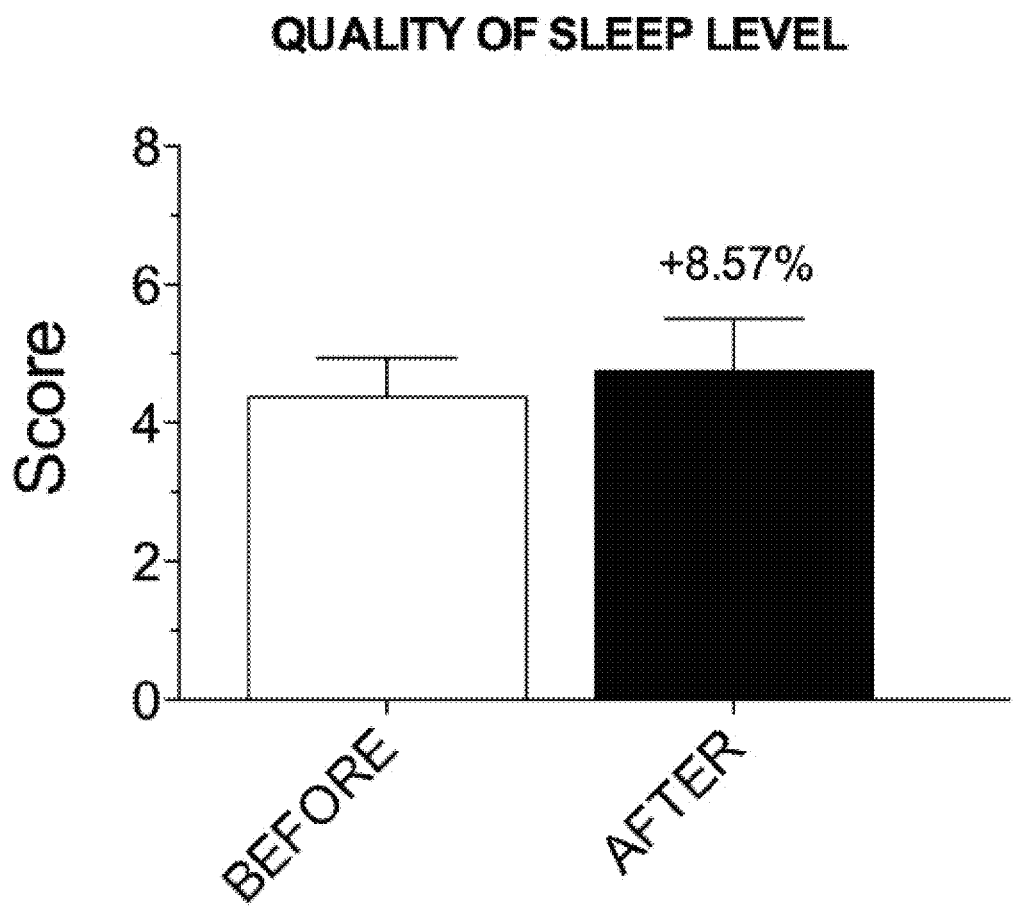
FIG. 15 is a graph illustrating a non-limiting example of a self-reported improvement of greater than 8.5% overall quality of sleep in human subjects with an apparel of the instant disclosure.

4) "How do you rate your overall quality of sleep for the past 2 weeks? Check the number that best describes your overall sleep 1=really good 10=really bad." FIG. 15 is a graph illustrating a self-reported improvement of greater than 8.5% overall quality of sleep in human subjects wearing a shirt of the disclosure while exercising in a Zumba fitness program.

Figure 16:
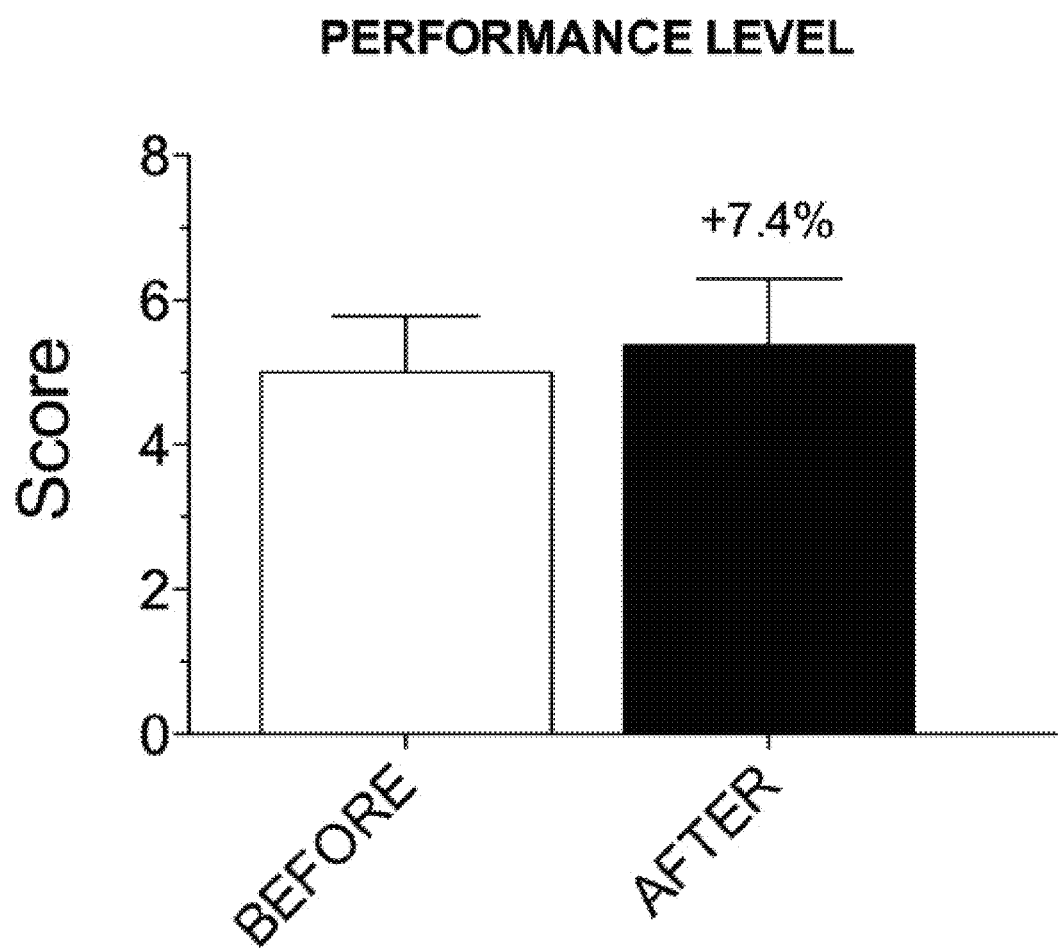
FIG. 16 is a graph illustrating a non-limiting example of a self-reported improvement of greater than 7% overall performance level in human subjects with an apparel of the instant disclosure.

5) How would you rate your overall performance level for the past 2 weeks. Check the number that best describes your overall performance 1=really good 10=really bad." FIG. 16 is a graph illustrating a self-reported improvement of greater than 7% overall performance level in human subjects wearing a shirt of the disclosure while exercising in a Zumba fitness program.

Conclusion: wearing a bioceramic shirt of the disclosure reduces overall pain, improves overall health levels, reduces overall fatigue, improves overall quality of sleep, and improves overall performance levels of humans participating in a Zumba Fitness program.

Example 26: Report on the Far Infrared Emission of Bioceramic Materials

Report of Absolute Emission: according to analysis of emission of radiant power in the infrared region in the range between 9 and 11 micrometers performed at Laboratory of Spectroscopy and Laser Institute of Exact Sciences, Federal University Fluminense, using urn calorimeter Scientech (Boulder, Colo., USA), Model 118, serial number 380802, attached to a unit measures power and energy Scientech, model 473, serial number 364002, in the following materials:

1) plain fabric (not comprising a bioceramic);
2) bioceramic fabric (30% bioceramics), the formulation of the bioceramic was as described in Example 1;
3) bioceramic fabric (50% bioceramics), the formulation of the bioceramic was as described in Example 1;

The analysis of the emissivity was taken based on the Stefan-Boltzmann equation given by: $P=\epsilon\sigma T^4$ where P is the radiant power per unit area (Watts/m$^2$), c is the emissivity of the wafer (no units), a is the Stefan-Boltzmann constant ($5.7\times10^{-8}$ W/m$^2$K$^4$) and T is the temperature of the materials in Kelvins. The emissivity of the material and a dimensionless quantity, is a material property, concerns the ability of emission of energy by radiation from its surface. And the ratio of energy radiated by urn particular material to energy radiated by black body urn (e=1). Any object that is not a true black body has emissivity that is less than 1 and greater than zero.

For analysis the materials were cut into discs of 15 mm in diameter and placed in a thermally insulated oven and maintained electronically in those temperatures (with a variation of ±1° C.). Once in thermal equilibrium, the oven set/disc was positioned in front of the calorimeter and radiation measurement performed.

The potential measurements per square meter for each material are adjusted as a function of temperature in Kelvin high fourth power. The emissivity value is calculated from the slope of the fitted straight through the method of least squares performed making use of QtiPlot program, free domain.

Figure 17:
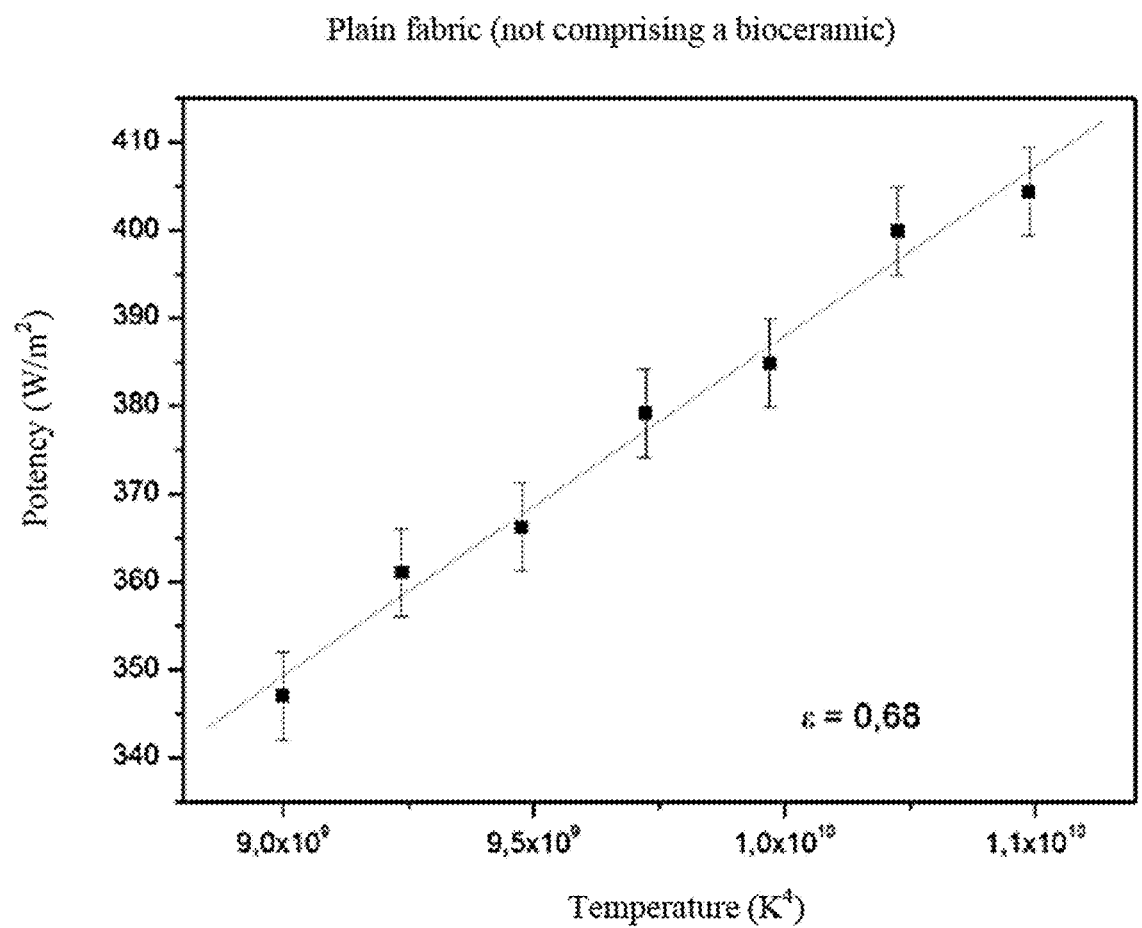
FIG. 17 shows a non-limiting example of the absolute infrared emission of plain fabric (not comprising a bioceramic).
Figure 18:
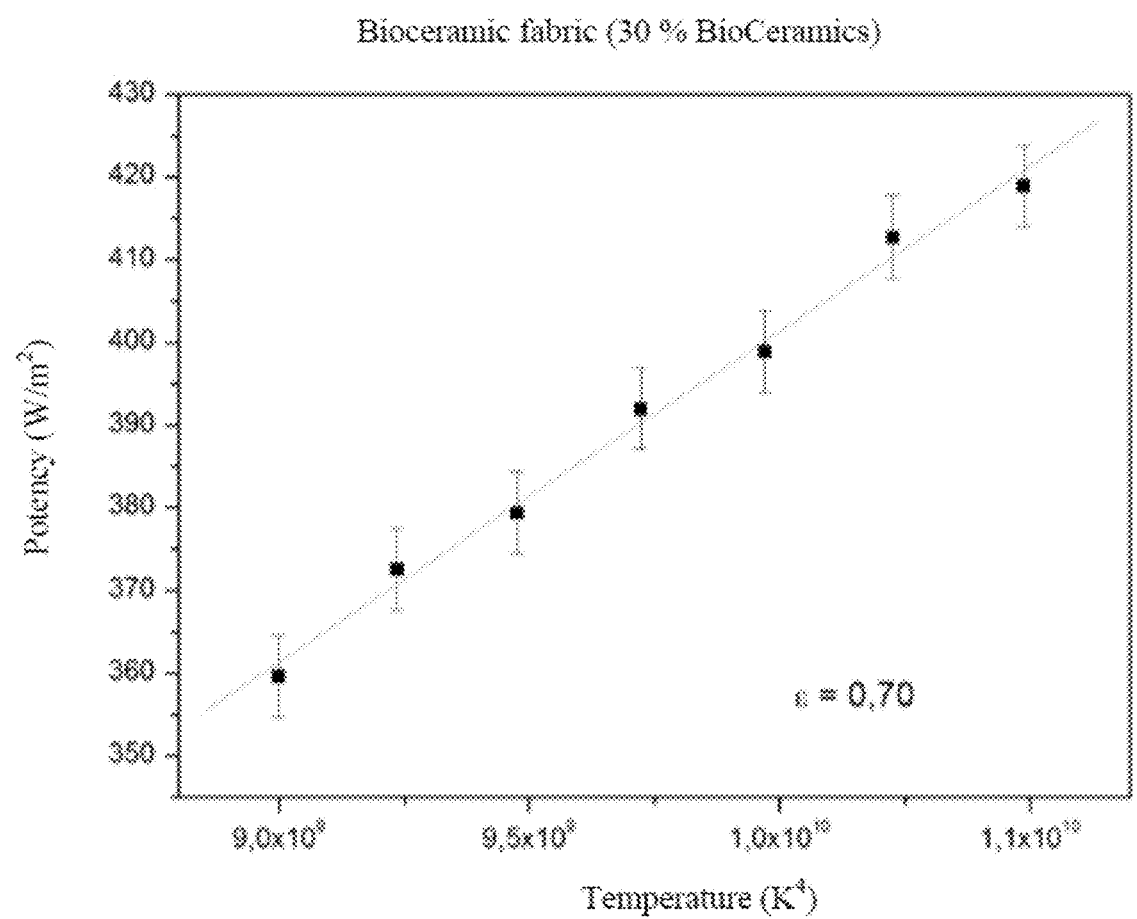
FIG. 18 shows a non-limiting example of the absolute infrared emission of a fabric comprising 30% bioceramics of the instant disclosure.
Figure 19:
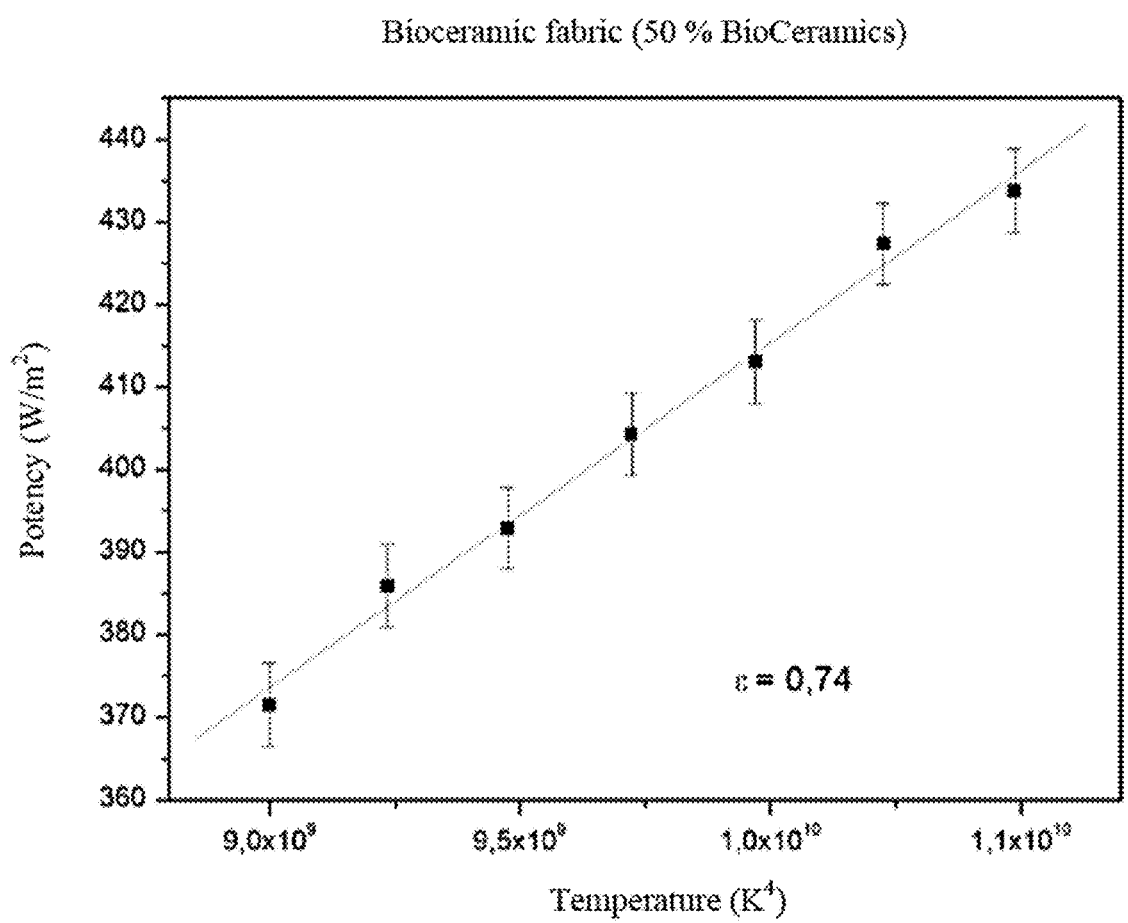
FIG. 19 shows a non-limiting example of the absolute infrared emission of a fabric comprising 50% bioceramics of the instant disclosure.

The results obtained are as follows:
1) plain fabric (not comprising a bioceramic): emission 0.68 (FIG. 17)
2) bioceramic fabric (30% bioceramics): emission 0.70 (FIG. 18)
3) bioceramic fabric (50% bioceramics): emission 0.74 (FIG. 19)

The results correspond to a mean value of measurements; an average of five measurements for each material, with an estimated error of ±0.02 was performed. In the samples tested the addition of bioceramic materials increased the absolute emissivity of materials which confirms the greater issuance of long-infrared spectral range 9 and 11 micrometers.

Example 27: Uses of Bioceramics Emitting Far Infrared Energy Improve Flexibility, Increase Back, Leg, and Grip Strength, Improve Respiratory Capacity, and Enhance Cardiorespiratory Fitness Objective: the aim of this study will be to evaluate the effect of apparel of the disclosure in improving flexibility, increasing back, leg, and grip strength, improving respiratory capacity, and enhancing cardiorespiratory fitness in a human.

Methods: the study will be designed as a controlled double blind clinic trial to test the statistical impact of a far-infrared emitting bioceramic shirt, sleeve, or patch in improving flexibility, increasing back, leg, and grip strength, improving respiratory capacity, and enhancing cardiorespiratory fitness in humans.

Study type: interventional. Subjects will be randomly divided into 3 (three) experimental groups and will receive treatment for at least 6 weeks:
a) group 1: receives no treatment.
b) group 2: wears an apparel of the disclosure: a shirt, a pad, or both, for "n" hours after the treatment.
b) group 3: wears a control apparel that does not comprise any bioceramic, for "n" hours after the treatment.

"n" hours can be about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours during the course of a day.

Endpoint classification: flexibility, back, leg, and grip strength, respiratory capacity, and cardiorespiratory fitness will be measured as previously described in Examples 11, 13, 14, 19, and 20.

Example 28: Uses of Bioceramics Emitting Far Infrared Energy as an Analgesic in Mice Objective: the aim of this study was to evaluate the analgesic effects of distinct bioceramic concentrations and treatment times in an experimental model of CFA induced inflammation in mice.

Methods: experiments were conducted using adult male Swiss mice weighing 25-35 grams, housed at 22° C. under a 12 hours light/12 hours dark cycle (lights on at 06:00 am), with access to food and water ad libitum. The experiments were performed after approval of the protocol by the Ethics Committee of the Universidade do Sul de Santa Catarina (UNISUL). The animals (n=8) underwent intraplantar injection (right hind paw) of a solution containing 20 µl of Freud's complete adjuvant (CFA, 70%). Naive animals were injected with saline solution. Mechanical nociceptive threshold was assessed as response frequency to 10 presentations of a 0.4 g von frey filament applied to the animals right hind paw.

In experiment number 1 the animals were placed in their housing boxes for 2 hours on top of a either: (1) a pad composed of 70% BioCorn PVC and 30% bioceramics; (2) a pad composed of 90% BioCorn PVC and 10% bioceramics; or (3) a pad composed of 100% BioCorn PVC and 0% bioceramics. After 2 h of exposure mechanical nociceptive threshold was assessed. Naive animals were not treated.

In experiment number 2 the animals were placed in their housing boxes on top of a pad composed of 70% BioCorn PVC and 30% bioceramics for either 0.5, 1 or 2 hours. Afterwards mechanical nociceptive threshold was assessed. Naive animals were not treated.

Figure 20:
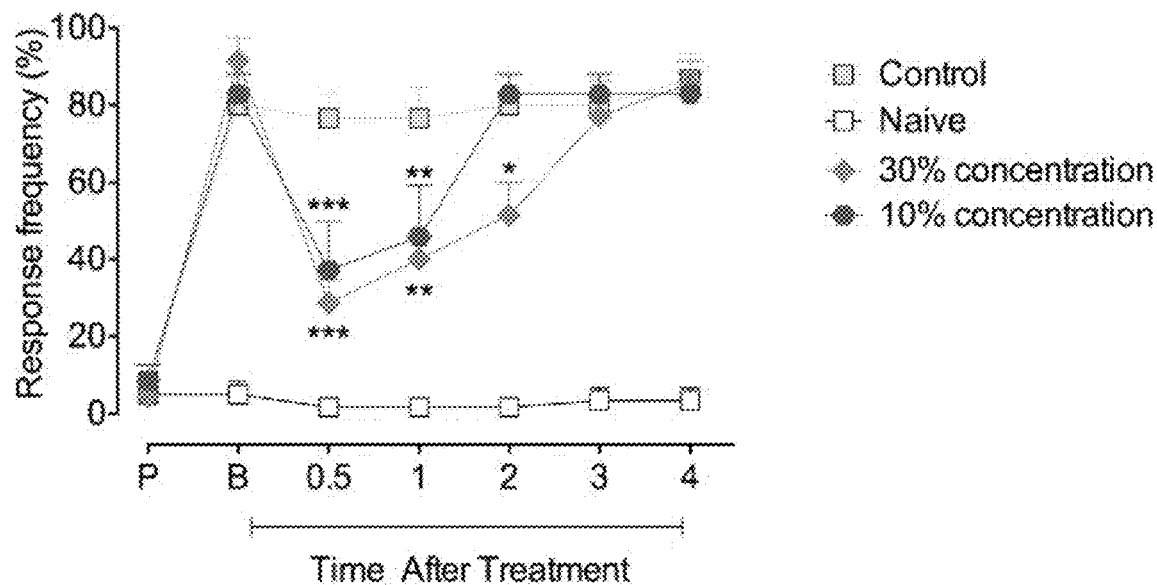
FIG. 20 are non-limiting examples of graphs illustrating that exposure to a pad with a higher bioceramic concentrations and longer periods of exposure (both embodiments of the instant disclosure) induced longer lasting results.
Figure 20:
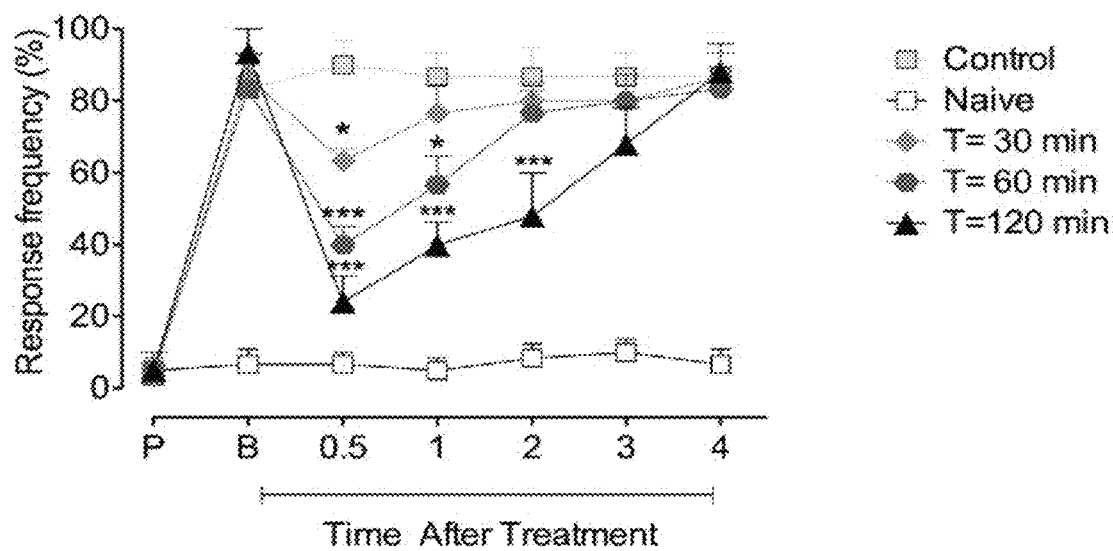

Results: the results show that the i.pl. injection of CFA induced mechanical hypernociception ($P<0.001$) which was significantly reduced by acute exposure to the pads containing bioceramics. Exposure to the pad with a higher bioceramic concentration induced longer lasting results (FIG. 20, panel A). Longer exposure to the bioceramic pad induced longer lasting results (FIG. 20, panel B).

Conclusion: exposure to Bioceramic Pad reduced mechanical hypernociception of inflammatory origin induced by intraplantar injection of CFA in mice in a dose-dependant manner.

Example 29: Effect of Bioceramics in the Growth of Organic Produce

Objective: to evaluate the effect of BioPower® on the growth of hydroponic lettuce (*Lactuca sativa*).

Methods: experiments were conducted with lettuce (*Lactuca sativa*) cultivated in a hydroponic system. Control group was cultivated following standard hydroponics methodology. Experimental group (bioceramics) was treated with bioceramic pellets (30% bioceramic, 70% polystyrene-polypropylene—1 pound) placed inside the water pump. The lettuce was cultivated for 3 weeks and collected for analyses.

Figure 21:
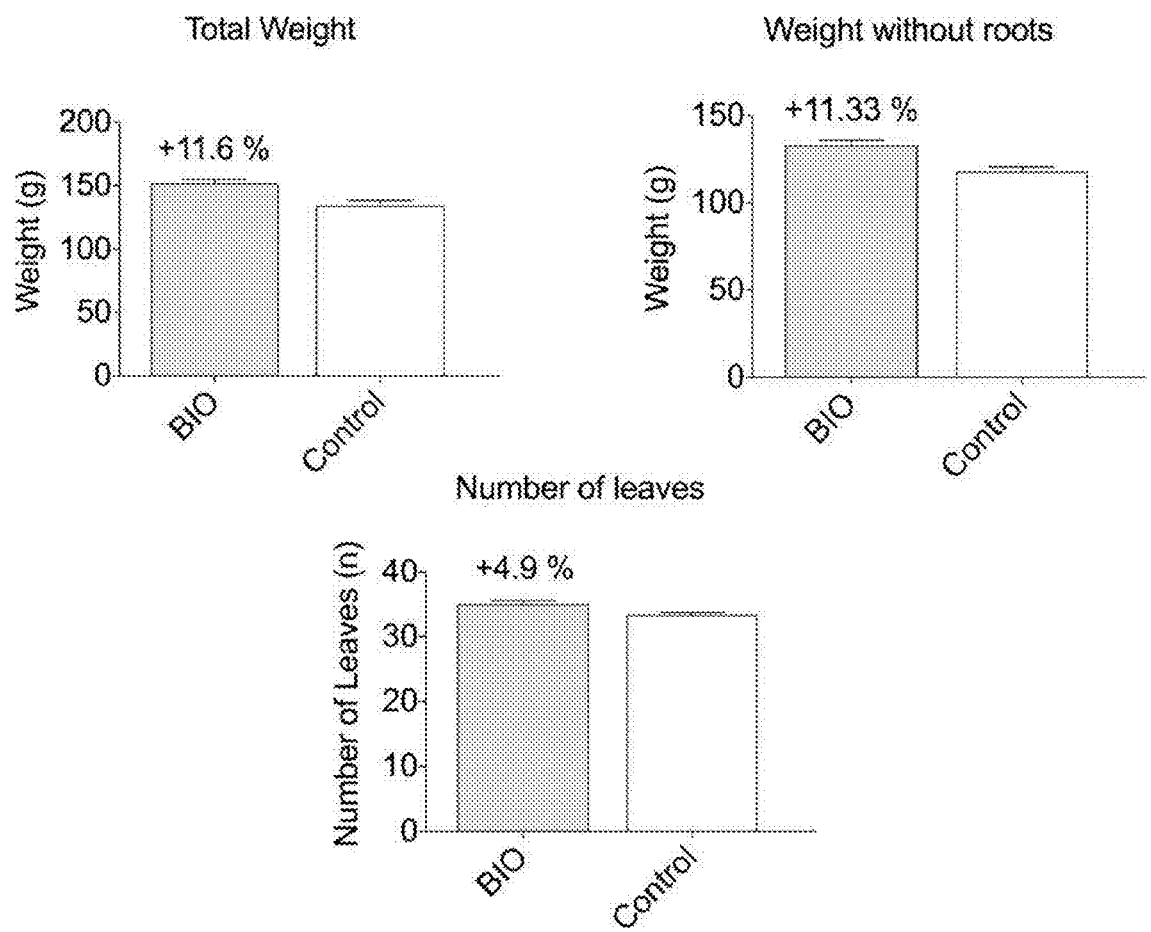
FIG. 21 are non-limiting graphs illustrating the effect of adding bioceramic of the instant disclosure to a water treatment in a hydroponic system.

Results: the results indicate that lettuce that received water treated with bioceramics weighted more and presented more leaves in comparison to control group. FIG. 21 are graphs illustrating the effect of adding bioceramic to a water treatment in a hydroponic system. n=12, the vertical lines indicate the S.E.M. *$p<0.05$.

Figure 22:
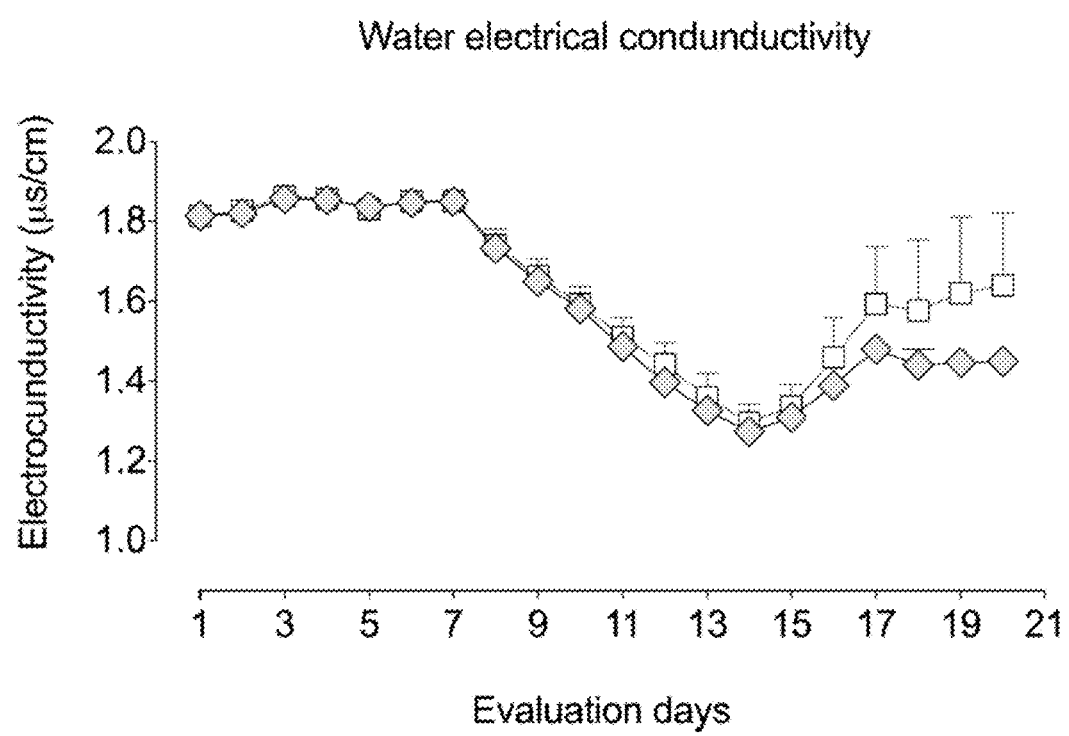
FIG. 22 is a non-limiting example of a graph illustrating the lower electrical conductivity of water treated with bioceramics of the instant disclosure presented from day 16 to 20 in comparison to control group (water only).
Figure 23:
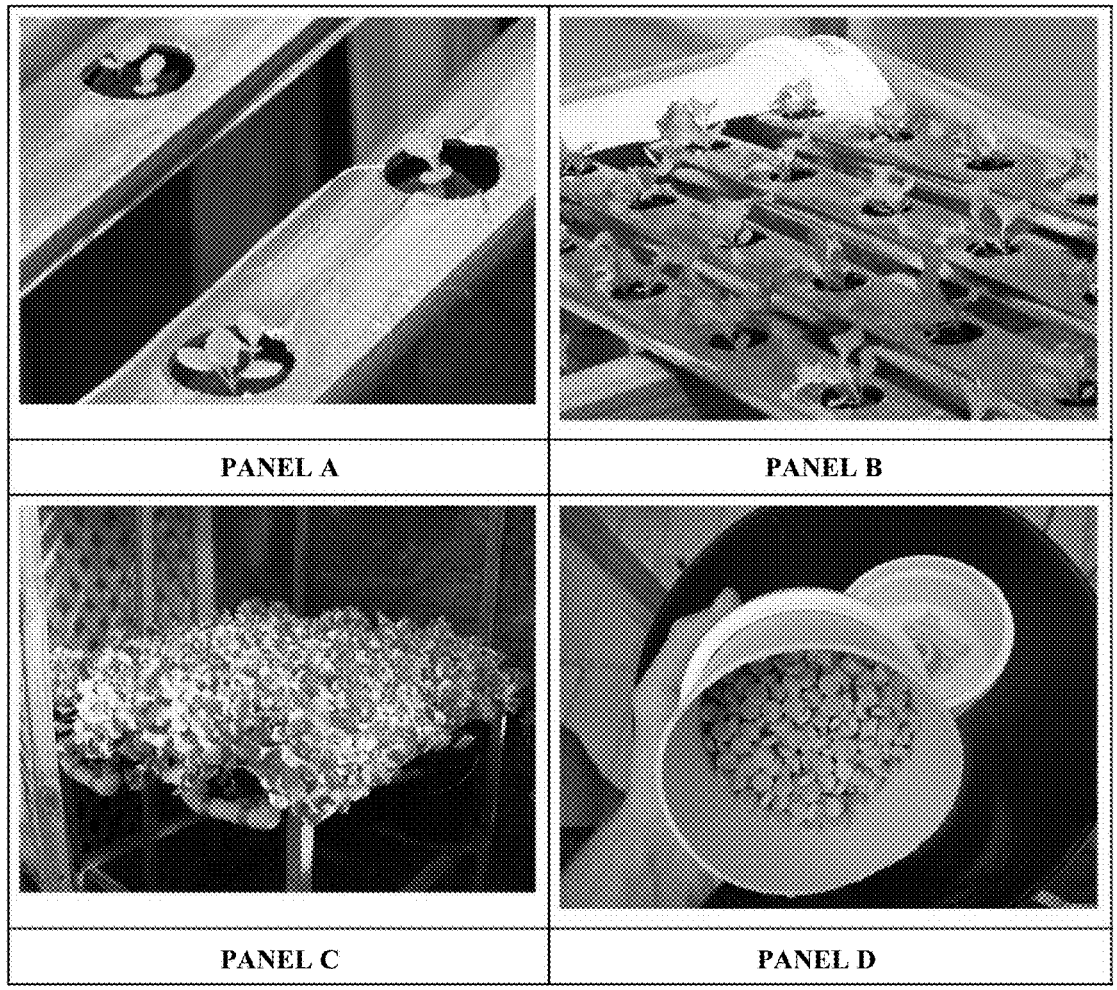
FIG. 23 are non-limiting examples of photographs showing the effect of bioceramics of the instant disclosure in the growth of organic produce.
Figure 24:
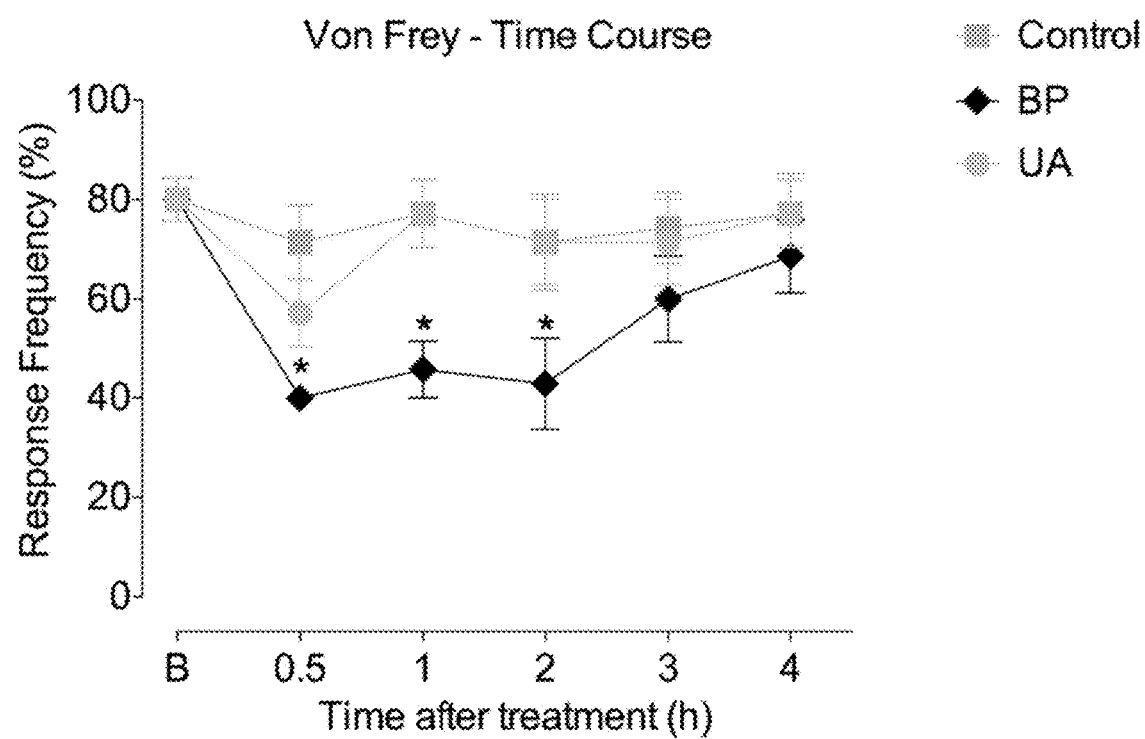
FIG. 24 is a graph illustrating a non-limiting example of the analgesic effect of a far-infrared emitting bioceramic (cFIR) of the instant disclosure versus a different formulation in the CFA mouse model of induced mechanical hypersensitivity.

Electrical conductivity (EC) (displayed in microsiemens (µS)) is a measurement of the nutrient solutions ability to conduct an electrical current. Pure water (deionized water) is an insulator. It is the conductive substances (or ionized salts) dissolved in the water that determine how conductive the solution is. With few exceptions, when there is a greater concentration of nutrients, the electrical current will flow faster, and when there is a lower concentration, the current will flow slower. This is because the quantity of dissolved solids in the nutrient solution is directly proportional to the conductivity. Thus, by measuring the EC, one can determine how strong or weak the concentration of the nutrient solution is. In this case, a lower electrical conductivity in the experimental group (BioPower group) denotes a lower concentration of nutrients in the solution, which may suggest that BioPower treated plants absorbed more nutrients than control groups plants. FIG. 22 is a graph illustrating the lower electrical conductivity of water treated with bioceramics presented from day 16 to 20 in comparison to control group (water only). FIG. 23 are photographs showing the lettuce at the start of treatment—$1^{st}$ day in the system (FIG. 23 panel A); the lettuce after the first week of treatment (FIG. 23 panel B); the lettuce after the third week of treatment (FIG. 23 panel C); and a photograph of the bioceramic pellets used in the experiment (FIG. 24).

Example 30: Randomized, Double-Blind, Placebo Controlled Clinical Test of Effect of Bioceramics Emitting Far Infrared Energy in Humans Participating in Exercise or Fitness Programs Objective: to investigate the effect of far-infrared emitting ceramic (cFIR) apparel on humans engaging in Zumba (ZUMBA®) exercise or fitness programs.

Background: bioceramics are refractory, inorganic, non-metallic polycrystalline compounds that due to their inertness in aqueous conditions are highly biocompatible and have been extensively used in implants. The bioceramic fabrics and apparel disclosed herein have been optimized for their ability to reflect/emit far-infrared (FIR). The purpose of this study is to evaluate the effect of fabrics comprising bioceramics in conjunction with exercising or fitness programs in humans.

Design: randomized, double-bind, placebo-controlled trial. Demographics: study will include male and female subjects of various ages.

Intervention: human subjects will participate in Zumba (ZUMBA®) exercising or fitness programs. All human subjects will participate in Zumba exercising or fitness programs at least once a week. Subjects will be randomly divided into three experimental groups:

Group 1 (Non-treatment control—plain apparel): subjects in this group will wear plain control shirts and/or leggings (pants) during Zumba exercise or fitness programs.

Group 2 (Placebo control—shirt and/or leggings (pants) comprising a ceramic that does not reflect infrared energy or rays): subjects in this group will wear control shirts and/or leggings (pants) comprising a ceramic that does not reflect infrared energy or rays during Zumba exercise or fitness programs.

Group 3 (Experiment—shirt and/or leggings (pants) comprising about 50% by weight of the following bioceramic composition: about 18% aluminium oxide $Al_2O_3$, about 14% silicon dioxide $SiO_2$, about 50% kaolinite $(Al_2Si_2O_5(OH)_4)$, about 8% zirconium oxide $(ZrO_2)$, and about 10% Tourmaline $(NaFe^{2+}{}_3Al_6Si_6O_{18}(BO_3)_3(OH)_3OH))$. Subjects in this group will wear shirts and/or leggings (pants) comprising the said bioceramic during Zumba exercise or fitness programs. Experiments measuring the amount of infrared energy emitted by the aforementioned apparel have been described in EXAMPLE 26. Additional experiments measuring the amount of infrared energy emitted by shirts before, during, and after subjects participate in Zumba exercising or fitness programs will be performed.

Evaluations: The following evaluation methods will be used to measure the effect of fabrics comprising bioceramics in humans in conjunction with exercising or fitness programs:

Body composition: Body Mass Index (BMI) and waist circumference: body fat percentage will be measured either by the skin fold method or using Bioelectrical Impedance Analyses (BIA). Body composition will be evaluated at least twice: 1) a baseline evaluation will be conducted prior to the beginning of the interventional and control tests; and 2) at least one follow-up evaluation will be conducted at the end of a period of 6 weeks after the start of the intervention.

Cardiovascular fitness: The Harvard Step test will be used to measure "aerobic" or "cardiovascular" fitness. The Harvard step test is an art acknowledged method to measure how oxygen consumption increases with exercise intensity. $VO_2max$ is defined as the highest rate of oxygen consumption attainable during maximal or exhaustive exercise.

Harvard Step test protocol: The participant steps up onto, and back down from the step at a rate of 30 completed steps per minute (one second up, one second down) for 5 minutes or until exhaustion. Exhaustion is defined as when the participant cannot maintain the stepping rate for 15 continuous seconds. The subject immediately sits down on completion of the test, and the subject's total number of heart beats are counted, based on their pulse at their wrist, within the following time-frames: a) from a minute to a minute-and-a-half after finishing; b) from two minutes to two-and-a-half minutes after finishing; and c) from three minutes to three-and-a-half minutes after finishing.

Cardiovascular fitness will be evaluated at the end of Zumba (ZUMBA®) exercise or fitness classes: 1) a baseline evaluation will be conducted prior to the beginning of the interventional and control tests; and 2) follow-up evaluations will be conducted at the end of Zumba (ZUMBA®) exercise or fitness classes. The subjects fitness index score will then be determined by the following equations: Fitness Index=(100×test duration in seconds) divided by (2×sum of heart beats in the recovery periods).

Flexibility: the Flexibility of each human subject is be measured with the sit-and-reach test (Novel Flex-Tester® Sit & Reach Box). For evaluation each subject will be asked to sit on the floor with knees flat against the floor and the box flat against the plantar aspect of his/her feet. Then the subject stretches out and reaches towards the box moving the distance indicator as far as possible. The mean of 3 measurements will be used in the analysis. Flexibility will be evaluated at the end of Zumba (ZUMBA®) exercise or fitness classes: 1) a baseline evaluation will be conducted prior to the beginning of the interventional and control tests; and 2) follow-up evaluations will be conducted at least once a week for a total of six weeks at the end of Zumba (ZUMBA®) exercise or fitness classes.

Back and Leg strength: Back/leg dynamometer (Baseline, United States) will be used to measure leg and back muscle strength. Leg muscle strength will be recorded at a standing position while both knees are flexed at an angle of 135°. For evaluation of back muscle strength the participant is asked to stand on the device's platform with both knees flexed at an angle of 135°. Using a pronated grip the participant holds the device's handle bar and slowly straightens his legs up to their maximal level without using back or shoulder muscles. For evaluations of back muscle strength, subjects are asked to repeat the described procedure while using their back muscles only (knees are kept in extension). Flexibility will be evaluated at the end of Zumba (ZUMBA®) exercise or fitness classes: 1) a baseline evaluation will be conducted prior to the beginning of the interventional and control tests; and 2) follow-up evaluations will be conducted at least once a week for a total of six weeks at the end of Zumba (ZUMBA®) exercise or fitness classes.

Questionnaires: subjects will optionally be asked to answer questionnaires that aim to assess the effects of the intervention on parameters associated with: general health, sleep, pain, perceived wellness, or quality of life. Exemplary questionnaires include: Short-Form health survey (SF-36); the Pittsburgh sleep quality index (PSQI); the McGill Pain Questionnaire; a Wellness Questionnaire; the WHO Quality of Life Questionnaire (WHOQOL-BREF); the questionnaire described in EXAMPLE 25, and/or a number of variations of these.

Example 31: Randomized, Double-Blind, Placebo Controlled Clinical Test of Effect of Bioceramics Emitting Far Infrared Energy in Humans Participating in Exercise or Fitness Programs Objective: To evaluate the effect of far-infrared emitting ceramic (cFIR) shirts on physical fitness parameters.

Methods: Each participant is randomly divided into 2 (two) experimental groups:

Experimental group I (cFIR shirts): each participant wears a cFIR shirt for a minimum of four hours after engaging in physical exercise and a minimum of 4 hours daily in between exercising days.

Experimental group II (placebo shirts): Participants wear a placebo shirt (no cFIR) for a minimum of 4 hours after the exercising protocol and a minimum of 4 hours daily in between exercising days.

Study type: Randomized, double-blind, placebo controlled clinical test.

Fitness program: subjects will participate in a 1-hor Pilates exercise session 3 times a week. The standardized, progressive treatment protocol will address muscle activation strategies through a variety of movement patterns involving muscle activation strategies through a variety of movement patterns involving muscles extension/contraction. In the protocols the participants will be required to consciously recruit specific muscle groups in a variety of movement patterns to exercise all main muscle groups and increase physical fitness as a whole.

Sample size and population: results from Experimental group I (cFIR shirts) and Experimental group II (placebo shirts) will be compared. A reasonable number of subjects required to provide α=0.05 with a power of 0.95 is estimated to be a total of 62 subjects divided between both experimental groups (31 subjects in each group). The required number of subjects was calculated with G*power Statistical Power Analyses version 3.1 (Heinrich-Heine-Universität Düsseldorf, Germany) and is as follows:

Analysis: a priori
Input: effect size f=0.35/α err propb=0.05/Power (1-β err prob)=0.95/number of groups=2/Number of measurments=9/Correlation among rep measures=0.5
Output: noncentrality parameter λ=13.6710000/Critical F=4.0011914/numerator df=1.0000000/Denominator df=60.0000000/Total sample size=62/Actual power=0.9532935

Randomization: the participants will be randomly assigned to each group. A research assistant will generate random numbers using a Research Randomizer software. These numbers will be stored on a computer and will be accessible only by the assistant. No stratification or blocking strategies will be used.

Suggested number and frequency of evaluations: a baseline evaluation is conducted before the beginning of the study, followed by a weekly evaluation for a total of 6 (six) weeks (minimum).

Endpoints Measured:

A) Functional capacity:
Balance: the static balance of each human subject is measured with (stabilometric exam) using a pressure plate (Medicapteurs®, S-Plate® model). The platform records deviations from the center of pressure (COP) in the anterior-posterior and mediolateral directions. Data acquisition is performed for 30 seconds under the following conditions: 1) condition 1: human subjects maintain their eyes open during the measurements; condition 2: human subjects maintain their eyes closed during the measurements.

Cardiorespiratory capacity: the oxygen consumption (V02) of each human subject is calculated with a regression equation as taught by King et al (J Rheumatol 1999; 26: 2233-7).

B) Body composition:
Body mass index, fat mass index, skeletal muscle mass index, percentage of body fat: are calculated with bioelectrical impedance analysis.

C) Far-infrared emissivity of human subjects wearing the bioceramic apparel: human subjects are photographed before, during and after the exercise protocol with an infrared thermographic camera (Flir E6 IR camera, FLIR Systems, Inc). Far-infrared images are used to determine changes in body temperature triggered by the cFIR emissions and/or physical activity.

D) Far-infrared emissivity of bioceramic shirts and other apparel: FIR Emissivity of the shirts is measured with the Astral Series S calorimeter AC2500S attached to a handheld meter (Astral AI310 (Scientech, Boulder, Colo., USA). Far infrared emissivity of bioceramic shirts with a calorimeter are used to determine FIR emissivity of the shirts in real time. Evaluations are conducted before and after the human subject participates in the exercise protocol (pilates class). Evaluations are optionally conducted during the exercise class.

E) Blood/saliva samples will be collected for biochemical analyses (muscle stress markers/inflammation markers/oxidative stress markers):

Muscle stress markers: creatine kinase (CK) and lactate dehydrogenase (LDH).

Inflammation markers: interleukin (IL)-10, IL-6, IL-1β, and Tumor Necrosis factor (TNF)-α.

Oxidative stress: thiobarbituric acid reactive substances (TBARS), carbonylated proteins, catalase (CAT) and superoxide dismutase (SOD)

F) Questionnaires:
The following questionnaires will be used to obtain a personal evaluation from each subject:
a) the modified Borg Scale of Perceived Exertion (RPE);
b) the Pittsburgh sleep quality index (PSQI);
c) the WHO Quality of Life-BREF (WHOQOL-BREF)

Example 32: Comparison of a Bioceramic of the Disclosure with a Different Bioceramic Composition Incorporated into the UnderArmour Cold Gear T-Shirt Objective: to compare the analgesic effect of a bioceramic of the claims versus a bioceramic far-infrared emitting bioceramic (cFIR) formulation provided by UnderArmour™ (UA) in a mice model of CFA induced mechanical hypersensitivity. The mouse model of CFA is further described in EXAMPLES 15, 16, and 18.

Evaluation of Mechanical Hypersensitivity: experiments were conducted using adult male Swiss mice weighing 25-35 g, housed at 22° C. under a 12 hour light/12 hour dark cycle (lights on at 06:00), with access to food and water ad libitum. The animals (n=8) underwent intraplantar injection (right hind paw) of a solution containing 20 μl of Freud's complete adjuvant (CFA, 70%) to induce mechanical hypersensitivity.

For treatment, either silk-screened fabric comprising either a far-infrared emitting bioceramic of the disclosure or a formulation described by UnderArmour™ was placed at the bottom of the animals' boxes. After 2 hours of exposure to the bioceramics, the mechanical nociceptive threshold of each animal was assessed as a response frequency to 10 presentations of a 0.4 g von frey filament applied to the animals right hind paw.

Results: CFA induced mechanical hypernociception in mice was significantly reduced by exposure to a fabric comprising a bioceramic of the disclosure, the bioceramic comprising about 40 wt % to about 60 wt % kaolinite ($Al_2Si_2O_5(OH)_4$), about 5 wt % to about 15 wt % tourmaline, about 15 wt % to about 25 wt % aluminum oxide ($Al_2O_3$), about 10 wt % to about 20 wt % silicon dioxide ($SiO_2$), and about 1 wt % to about 20 wt % zirconium oxide ($ZrO_2$). CFA induced mechanical hypernociception in mice was not reduced by exposure to a fabric comprising a bioceramic formulation described by UnderArmour. The analgesic effect lasted for up to 2 hours.

FIG. 24 is a graph illustrating the analgesic effect of a far-infrared emitting bioceramic (cFIR) of the disclosure versus the UnderArmour™ formulation in the CFA mouse model of induced mechanical hypersensitivity. N=8 mice per group, the vertical lines indicate the S.E.M. *p<0.05.

Conclusion: a bioceramic of the disclosure reduced mechanical hypersensitivity induced by CFA paw injection whereas a different formulation did not provide the analgesic effect.

Example 33: Infrared Transmittance of Bioceramics

Objective: to compare the infrared transmittance of a bioceramic of the instant disclosure (comprising 18% aluminium oxide, 14% silicon dioxide, 50% kaolinite, 8% zirconium oxide, and 10% tourmaline) to a distinct bioceramic composition (comprising 20% aluminum, 3% titanium, 11% magnesium oxide, 6% diiron trioxide, and 60% silica).

Methods: the infrared transmittance of powdered samples (particle size=about 25 micrometers) of the bioceramic powders was taken using a Bruker spectrometer (Model Spectrum VERTEX 70, OPUS 6.5 software). Transmittance (%) ratings were determined with a resolution of 4 $cm^{-1}$ and 72 scans at a scan range from 350 $cm^{-1}$ to 4000 $cm^{-1}$.

Figure 25A:
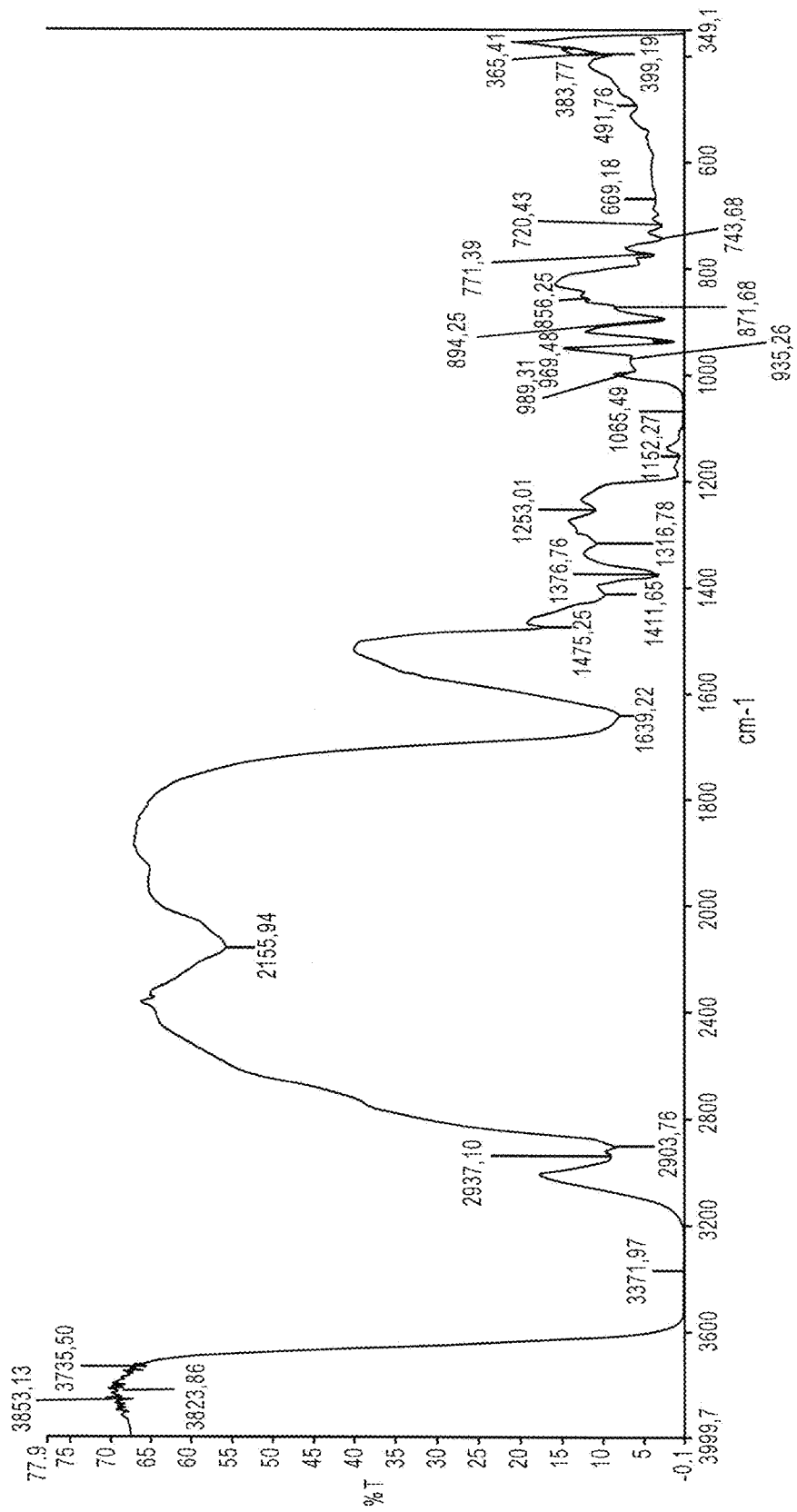
Figure 25B:
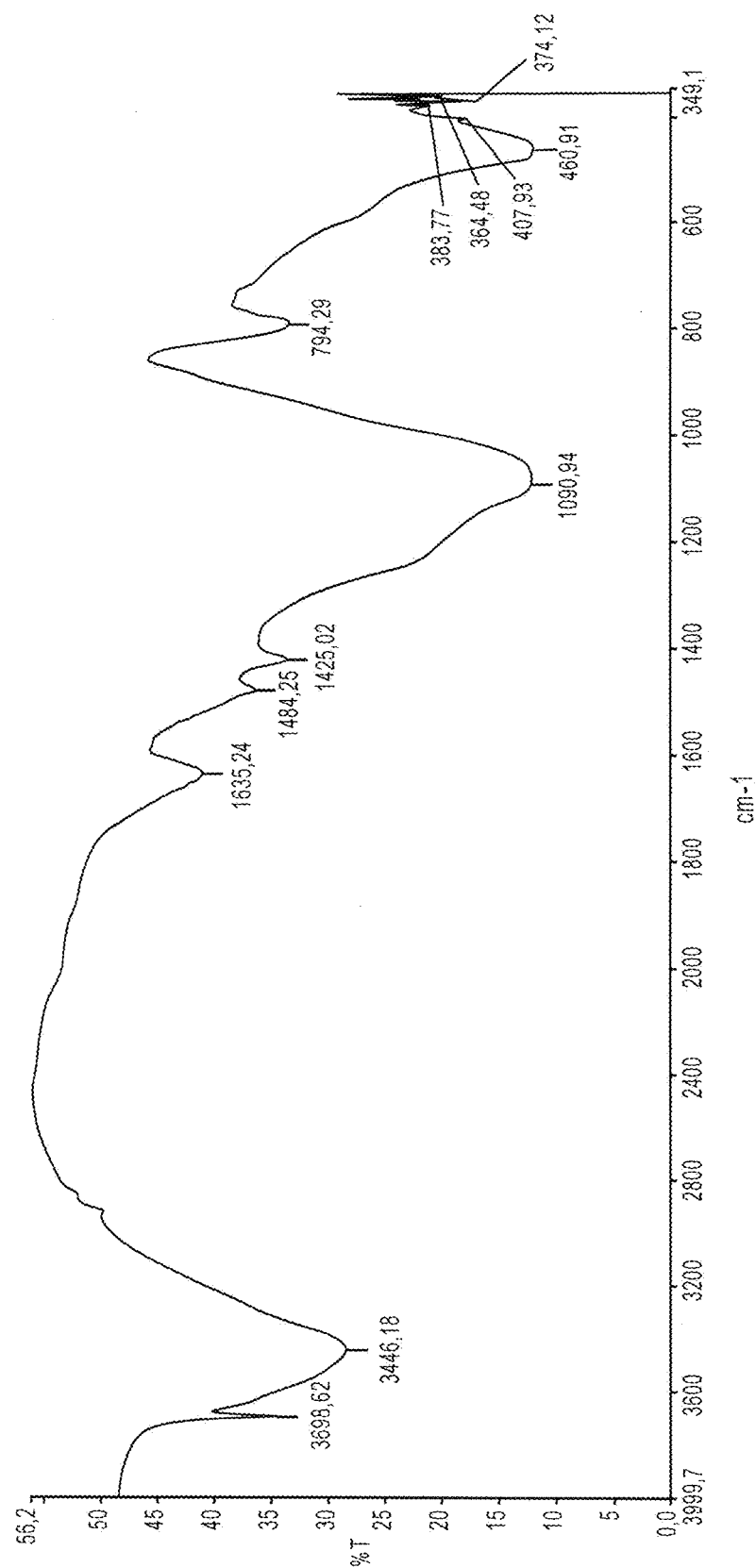
FIG. 25B illustrates the infrared transmittance of a bioceramic compositions described herein comprising 20% aluminum, 3% titanium, 11% magnesium oxide, 6% diiron trioxide, and 60% silica

FIG. 25A illustrates the infrared transmittance of a bioceramic composition of the instant disclosure comprising 18% Aluminium oxide, 14% silicon dioxide, 50% kaolinite, 8% zirconium oxide, and 10% tourmaline. FIG. 25B illustrates the infrared transmittance of a bioceramic composition comprising 20% aluminum, 3% titanium, 11% magnesium oxide, 6% diiron trioxide, and 60% silica.

Example 34: Effect of Far-Infrared Emitting Bioceramic Apparel on Fibromyalgia Human Subjects Undertaking Hydrotherapy Objectives: to investigate the effect of far-infrared emitting bioceramic apparel on the following parameters of human subjects afflicted with fibromyalgia: a) heart rate; b) performance-based functional exercise capacity, c) balance, d) overall perceived pain level, e) Fibromyalgia impact, Pain, Quality of Life and Health related Questionnaires; f) blood levels of inflammatory and anti-inflammatory cytokines, and g) blood levels of markers of oxidative stress and activity of anti-oxidative enzymes.

Study Design: Double-blind, placebo controlled trial.

Intervention: Participants followed a Hydrotherapy exercise regimen 3 times a week for a period of 6 weeks and were randomly divided in 2 different groups (Placebo and Bioceramic). Subjects in the placebo group wore "sham apparel", i.e., human subjects wore shirts that did not have far-infrared emitting properties (shirts lacked bioceramics). Subjects in the bioceramic group wore a shirt comprising bioceramics every night during sleep (6 to 8 hours), for 6 consecutive weeks, and also during the Hydrotherapy Sessions. Each hydrotherapy session consisted of four phases, i.e., (1) warming up: participants were asked to walk the length of the pool back and forth; (2) active stretching of upper and lower limbs; (3) active exercising of the upper and lower limbs; and (4) relaxation exercises through oscillatory movements. All Phases were guided by the therapist.

Sample size and population: 16 participants: 8 human females in each group with an even age distribution. All participants were women.

Evaluations: evaluations were conducted to assess the following parameters and endpoints: flexibility, grip strength, heart rate, pain, performance, and functional exercise capacity. The results listed below described the data obtained in the first 6 consecutive weeks of evaluations:

A) Heart rate: a heart monitor was used to evaluate flexibility of the human subjects. Number of evaluations: a baseline evaluation was conducted before the beginning of the tests. Follow-up evaluations were conducted before and after every hydrotherapy session (3 times a week for 6 weeks). The results of this test are illustrated in FIG. 26 and discussed below.

B) Performance-based functional exercise capacity: the six-minute walk test (6MWT) which measures the distance an individual is able to walk over a total of six minutes on a hard, flat surface was used to evaluate the functional exercise capacity of human subjects. Number of evaluations: a baseline evaluation was conducted before the beginning of the tests and 6 weeks after the start of tests. The results of this test are illustrated in FIG. 26 and discussed below.

Figure 26:
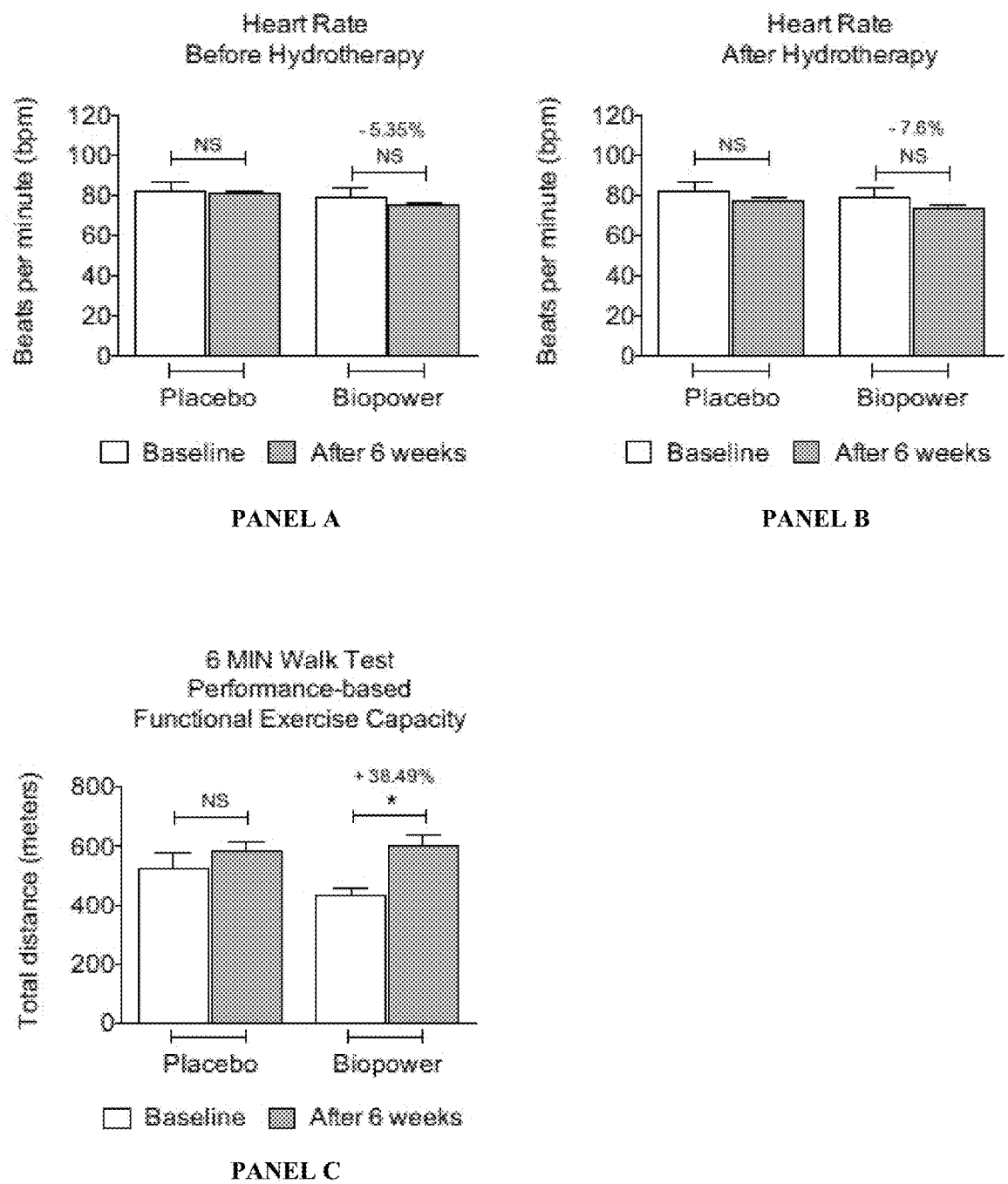
FIG. 26 is a graph illustrating the effect of far-infrared emitting bioceramic apparel on the heart rate and performance based functional exercise capacity of human subjects afflicted with fibromyalgia that followed a hydrotherapy treatment regimen.

FIG. 26 is a graph illustrating the effect of far-infrared emitting bioceramic apparel on the heart rate and performance based functional exercise capacity of human subjects afflicted with fibromyalgia that followed a hydrotherapy treatment regimen. Baseline evaluations were performed once a week before any intervention. FIG. 26 Panels A and B illustrate the cumulative effect of far-infrared emitting bioceramic apparel on the heart rate over a period of 6 weeks before and after hydrotherapy, respectively. FIG. 26 Panel C illustrates the performance-based measure of functional exercise capacity over total distance walked in meters over a period of 6 minutes. Baseline evaluations were performed once a week before any intervention. *$p<0.05$ indicates statistically significant difference between groups. (paired T-Test 95% confidence interval—Graphpad Prism software, USA, 2014).

Figure 27A:
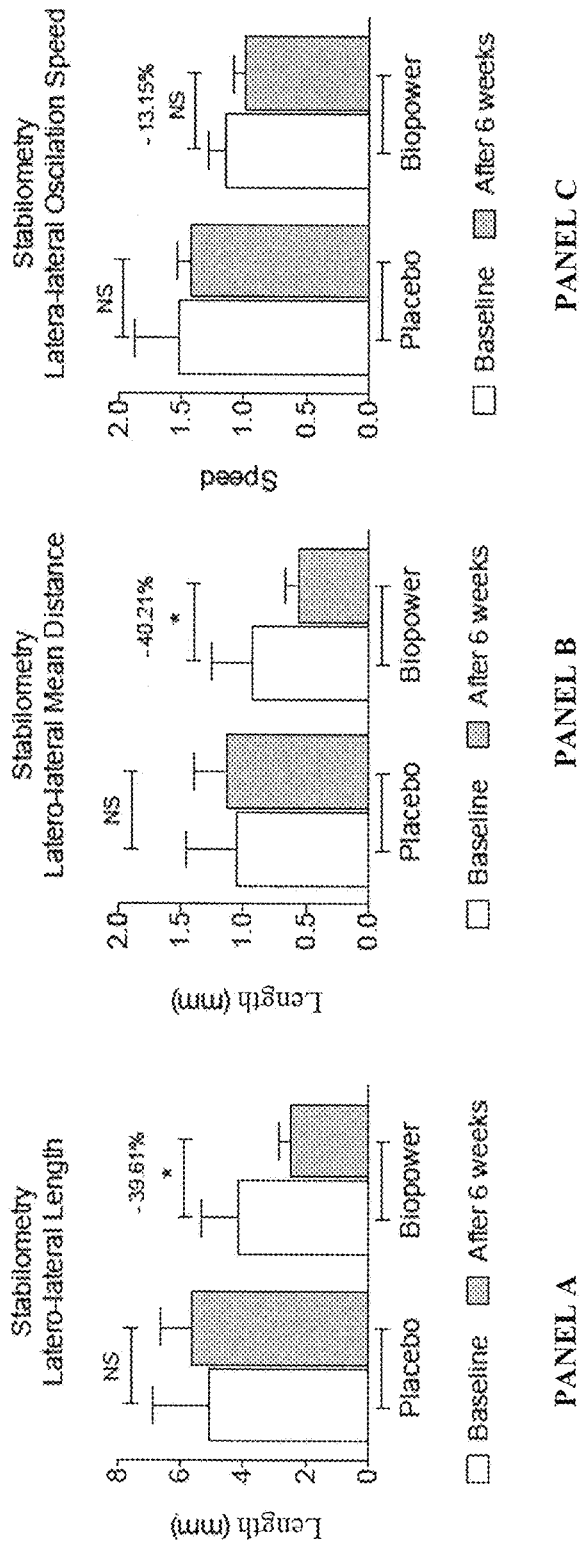
FIG. 27A and FIG. 27B demonstrate that hydrotherapy in combination with the use of control apparel did not affect the balance of the subjects, whereas the use of far-infrared emitting bioceramic statistically reduced latero-lateral oscillations.
Figure 27B:
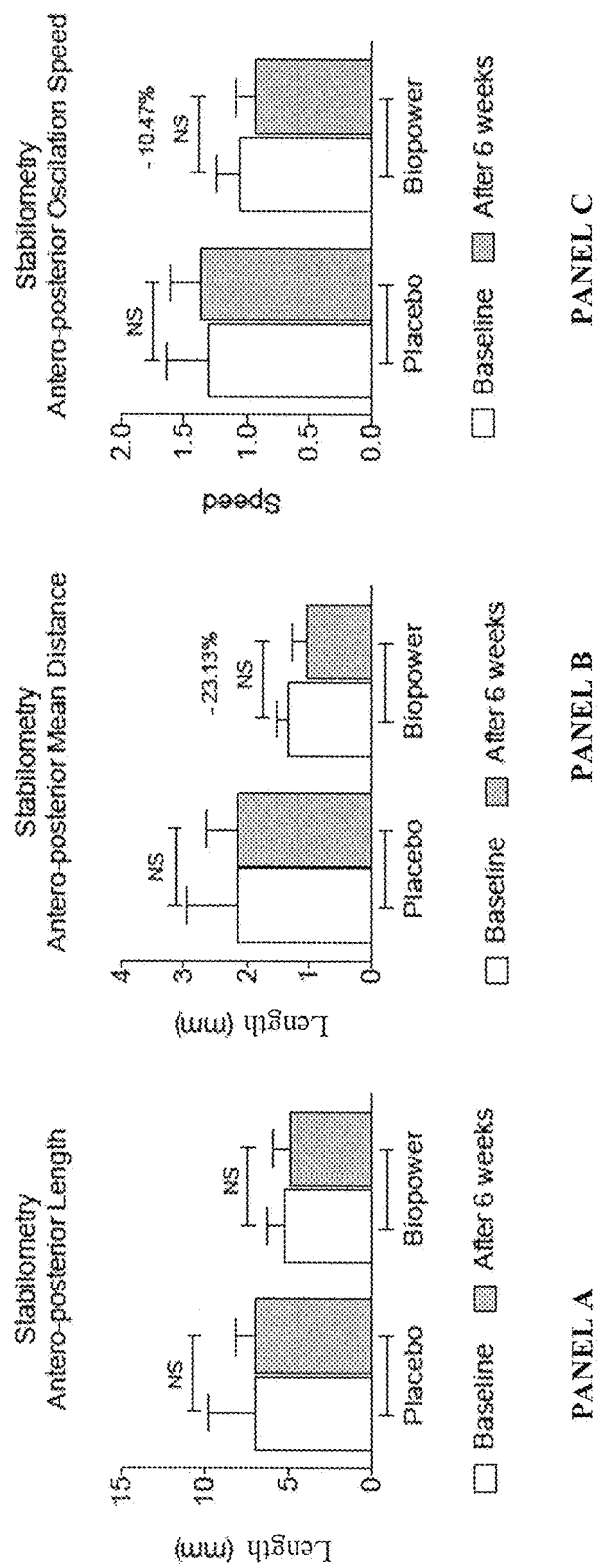

C) Balance: a stabilometry/baropodometry platform (S-Plate-Medicapteurs, France) was used to evaluate the balance of human subjects. Number of evaluations: a baseline evaluation was conducted before the beginning of the tests and a follow-up evaluations was conducted after 6 weeks of treatment. FIG. 27A and FIG. 27B are graphs illustrating the effect of far-infrared emitting bioceramic apparel on the balance of fibromyalgia patients that followed a hydrotherapy treatment regimen. FIG. 27A and FIG. 27B demonstrate that hydrotherapy in combination with the use of control apparel did not affect the balance of the subjects, whereas the use of far-infrared emitting bioceramic statistically reduced latero-lateral oscillations. FIG. 27A and FIG. 27B illustrate cumulative results over a period of 6 weeks. *$p<0.05$ indicates a statistically significant difference between groups. (paired T-Test 95% confidence interval—Graphpad Prism software, USA, 2014).

Figure 28:
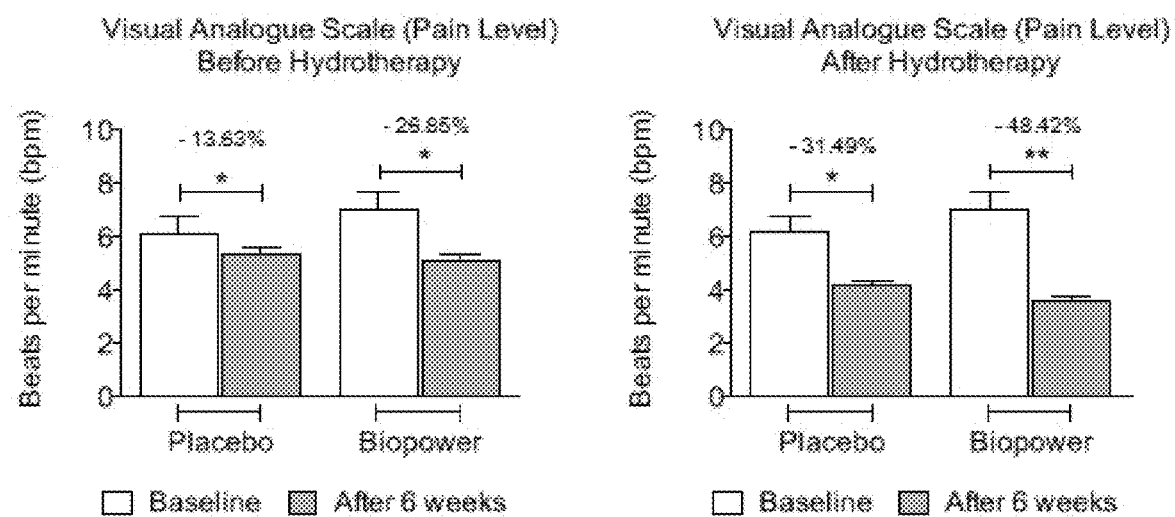
FIG. 28 is a graph illustrating the overall perceived pain level effects of human subjects afflicted with fibromyalgia that are treated with a far-infrared emitting bioceramic apparel or a sham apparel.

D) Overall perceived pain level: Visual Analogue Scale (VAS) was used to assess pain levels. Number of evaluations: a baseline evaluation was conducted before the beginning of the tests. Follow-up evaluations were conducted before and after each hydrotherapy session (3 times a week for 6 weeks). *$p<0.05$ indicates statistically significant difference between groups. Baseline evaluations were performed once a week before any intervention. (paired T-Test 95% confidence interval—Graphpad Prism software, USA, 2014). FIG. 28 is a graph illustrating the overall perceived pain level effects of human subjects afflicted with fibromyalgia that are treated with a far-infrared emitting bioceramic apparel or a sham apparel. Results shown in FIG. 28 suggest that: (1) Hydrotherapy in combination with the use of sham apparel or apparel comprising a bioceramic reduced the patients overall pain levels (compare baseline with before and after for each group—statistical significance not shown in the picture). (2) The results suggest a chronic effect (cumulative) of the combination treatment.

Figure 29A:
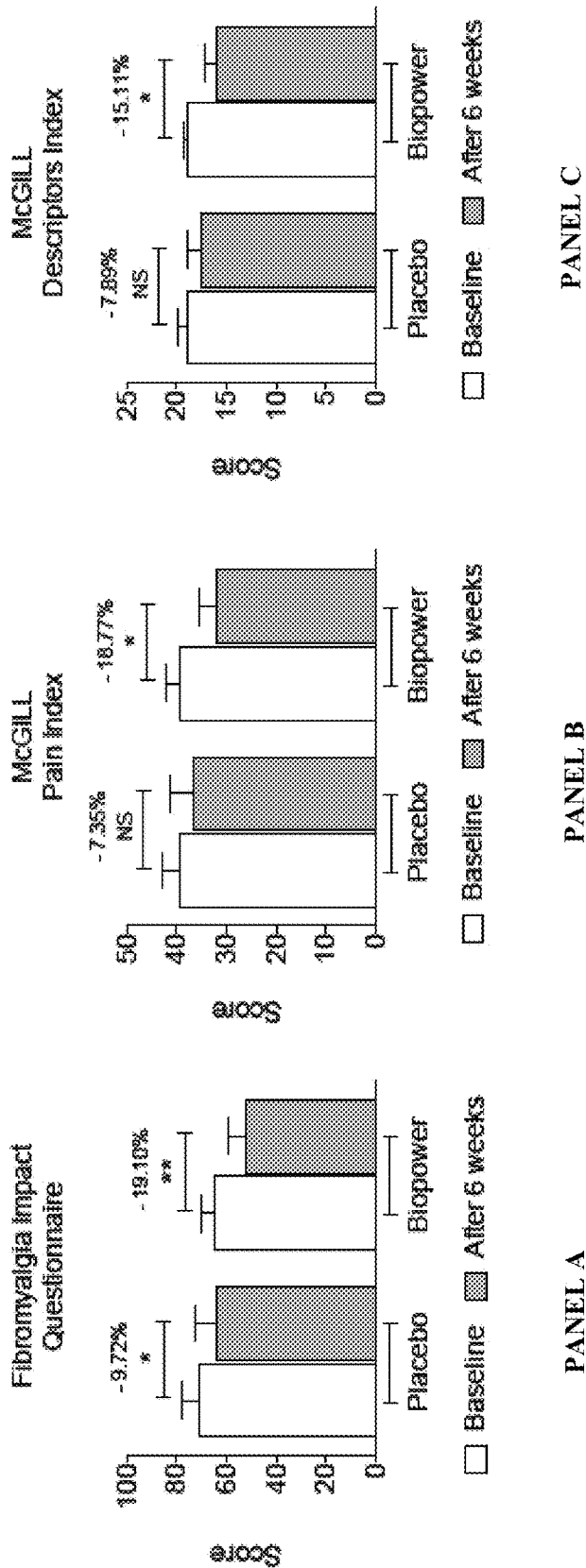
FIG. 29A is a graph illustrating the results of a fibromyalgia impact questionnaire (FIQ) (PANEL A), McGill pain questionnaire (PANEL B), and McGill descriptors index (PANEL C).

E) Fibromyalgia impact, pain, quality of life and health related questionnaires: Fibromyalgia Impact Questionnaire (FIQ), McGill pain questionnaire and McGill descriptors index, and SF-36 questionnaire (Physical Functioning, Pain and overall index) were used to assess the impact of a far-infrared emitting bioceramic on fibromyalgia, pain, quality of fife and other health related aspects. Number of evaluations: Baseline evaluation before the beginning of the tests and after 6 weeks. FIG. 29A is a graph illustrating the results of a fibromyalgia impact questionnaire (FIQ) (PANEL A), McGill pain questionnaire (PANEL B), and McGill descriptors index (PANEL C).*$p<0.05$ and **$p<0.01$ indicate statistically significant difference between groups. Baseline evaluations were performed once a week before any intervention. (paired T-Test 95% confidence interval—Graphpad Prism software, USA, 2014).

Figure 29B:
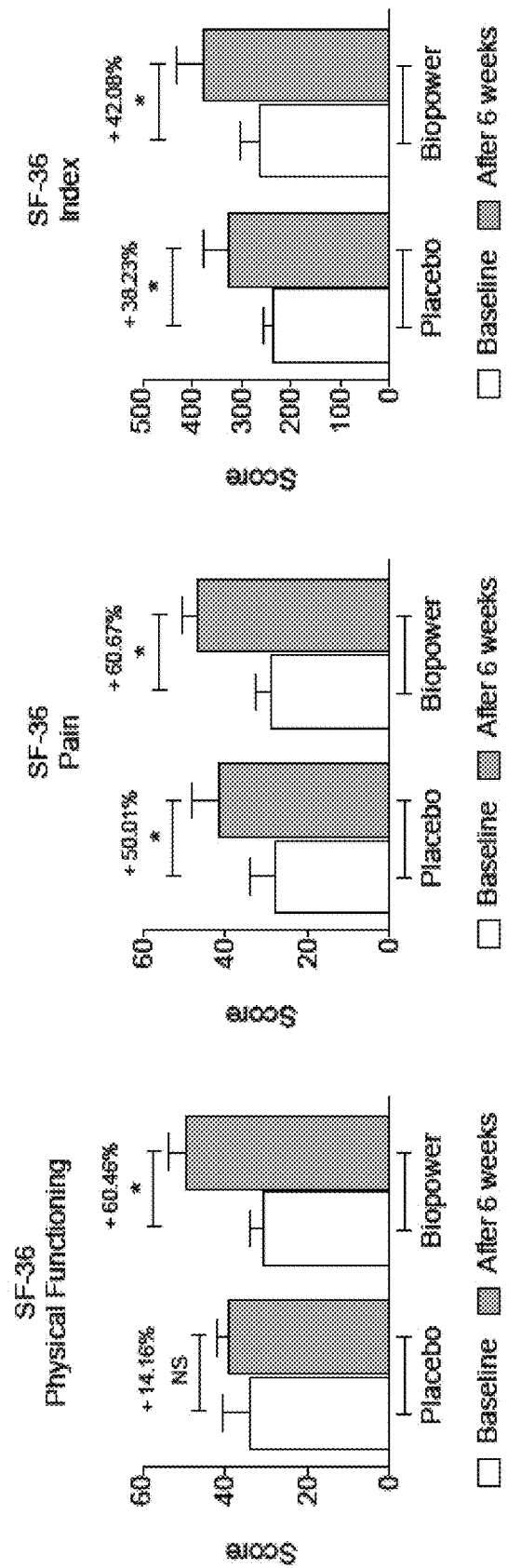
FIG. 29B is a graph illustrating the results of a SF-36 questionnaire; physical functioning (PANEL A), pain (PANEL B), and overall index (PANEL C).

Results depicted in FIG. 29A indicate that: (1) Hydrotherapy in combination with the use of placebo (sham) shirts or bioceramic shirts had a positive effect in the score of the FIQ, although the use of far-infrared emitting bioceramic shirts in combination with hydrotherapy was more effective than hydrotherapy alone (placebo shirt). (2) the use of bioceramic shirts alone statistically affect the McGill pain index and descriptors. Please note that the lower the score the better the result. FIG. 29B is a graph illustrating the results of a SF-36 questionnaire; physical functioning (PANEL A), pain (PANEL B), and overall index (PANEL C). Baseline evaluations were performed once a week before any intervention. (paired T-Test 95% confidence interval—Graphpad Prism software, USA, 2014). Results depicted in FIG. 29B indicate that hydrotherapy in combination with the use of placebo shirts or far-infrared emitting bioceramic had a positive effect in the SF-36 pain as well as overall index whereas the use of bioceramic shirts statistically affected all three scores. Please note that the score can vary from zero to 100, and the lower the score, the worse the prognosis.

F) blood levels of inflammatory and anti-inflammatory cytokines Enzyme-linked Immunoabsorbent Assay (ELISA) was used to assess the blood levels of inflammatory and anti-inflammatory cytokines. Number of evaluations: a baseline evaluation was conducted before the beginning of the tests. Follow-up evaluations were conducted before and after each hydrotherapy session (3 times a week for 6 weeks).

G) blood levels of markers of oxidative stress and activity of anti-oxidative enzymes. Enzyme-linked Immunoabsorbent Assay (ELISA) was used to assess the blood levels of inflammatory and anti-inflammatory cytokines. Number of evaluations: a baseline evaluation was conducted before the beginning of the tests. Follow-up evaluations were conducted before and after each hydrotherapy session (3 times a week for 6 weeks).

Example 35: Effect of Far-Infrared Emitting Bioceramic Apparel on Postural Sway of Judo Athletes Background: Postural control has been defined as the control of the body's position in space for the purposes of balance and orientation. Postural stability/Balance is an essential component in assessing the efficacy of interventions for improving balance.

Objectives: To determine the effects of far-infrared radiation emitting ceramic material-impregnated fabrics on postural sway in university judo fighters.

Design: Single-blinded randomized placebo controlled trial. 17 male and female volunteers who were randomly allocated to an experimental group (cFIR group, formed by 4 male and 4 female fighters that were asked to wear T-shirts impregnated with FIR emitting ceramic material during five months); and a control group (No-cFIR group formed by 5 male and 4 female fighters that were asked to wear sham/placebo T-shirts, i.e., that were not impregnated with cFIR emitting ceramic material). Randomization numbers were generated from a randomization site (randomization.com).

Participants: A total of seventeen judo fighters (nine men and eight women) participated in the present study. The following inclusion criteria were considered: (1) each human subject had to take part in official judo competitions during the calendar year; (2) each human subject had to train at least three times per week; (3) each human subject had to be between the ages of 18 and 35; (4) each human subject had to have been practicing Judo for at least 10. The following exclusion criteria were considered: (5) Individuals that presented a history of musculoskeletal injury to the hips, knees or ankles in the previous 2 months; subjects that made use of pharmacological agents or nutritional supplements; presented musculoskeletal injury during the study or that did not wear the shirt for a minimum of 4 hours a day were excluded from the study. All participants were competing at national level competitions.

Bioceramics and Apparel: The experimental group wore a T-Shirt impregnated with FIR-emitting bioceramic material. The bioceramic material was mixed with a textile ink (Silkscreen Plastisol, Imagine Color, Brazil) and applied to the bioceramic apparel, i.e. the T-shirts. The bioceramic ink was used to silkscreen a repetitive pattern in a 92% polyester, 8% spandex fabric which was used to impregnate the T-shirts with bioceramics. Sham shirts were silkscreened using the same pattern, although with a 100% plastisol ink (without far-infrared emitting ceramic powder). The average absolute emissivity of the ceramic powder was 93% at wavelengths of 9-11 µm, determined with a Scientech calorimeter (Boulder, Colo., USA), Astral series S AC2500S model, attached to a unit detector Scientech, model Astral series S AI310D. The control group wore a placebo shirt (without FIR-emitting ceramic material).

Figure 30:
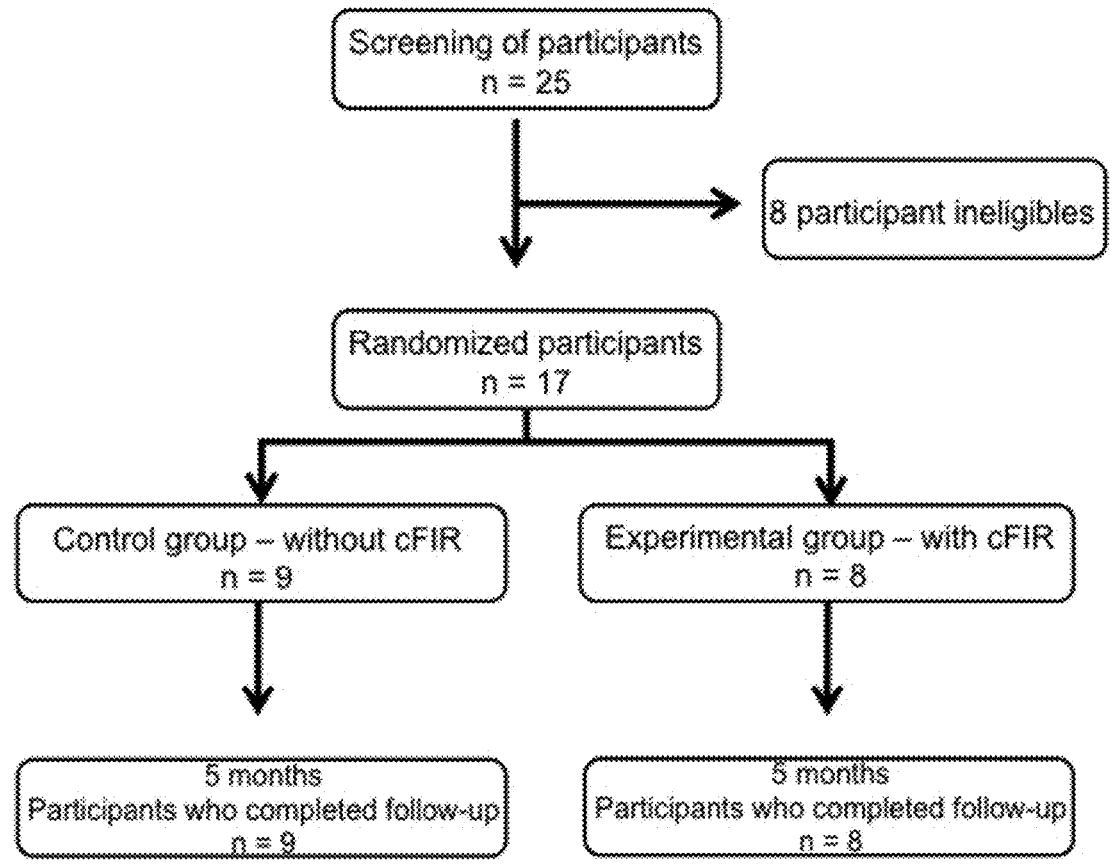
FIG. 30 is an organization flowchart of a study of the disclosure.

Interventions: participants were instructed by a blinded researcher to wear one of the shirts for four (4) hours daily during practice (which includes aerobic training, weight lifting and fight classes) for the duration of the experiments. The intervention lasted five months, with daily use of the bioceramic T-shirts (4 hours during practice). Static balance (stabilometry) was assessed before and after the intervention. The training protocol consisted of a 2 hour focus on fitness in the morning period and a 2 hour technical training specific for tatami in the afternoon period, 5 days a week. FIG. 30 is an organization flowchart describing the set-up of the study.

Endpoints: advancements in technology have provided the scientific community with computerized platform systems for the quantitative assessment of static balance. These systems provide an easy, practical, and cost-effective method to quantitatively assess functional balance through the analysis of postural sway. Such systems record the displacements of the centre of foot pressure (COP) by means of sensors embedded in the platform structure. The movements of the COP reflect both the horizontal location of the centre-of-gravity (COG) and the ground reaction forces due to the muscular activity of the lower limb, transmitted through the foot. Body sway can be measured as the persistent oscillation of the centre of mass (COM) referring to the antero-posterior (AP) and medio-lateral (ML) axes.

Statistical analysis: For the statistical analysis, the Kolmogorov-Smirnov test was used to determine the distribution of the sample, using the parametric test in the analysis of the pressure plate data. Paired and unpaired t tests were used for the intra and intergroup comparisons, respectively. The GraphPad prism program (version 5.0, Mac OS) was used for the statistical analysis, with the level of significance set at 5% ($p<0.05$).

Results: The total length and area of oscillation of the centre of foot pressure (COP) underwent a significant reduction following the treatment in the experimental group, with different degrees of reduction when the eyes were open ($p<0.05$), but not closed ($p>0.05$). Furthermore, the experimental group exhibited a reduction in the mediolateral and anterior-posterior deviations (width) of the COP following treatment in the open eyes analysis.

Analyses were performed for 25 participants (FIG. 30). The anthropometric characteristics of the participants are presented in TABLE 1. There was no statistically significant difference between the groups for personal characteristics.

TABLE 1

|  | Groups | |
| --- | --- | --- |
|  | Control | Experimental |
| Individuals (n) | 9 | 8 |
| Age (years) | 21.4 ± 2.6 | 22.3 ± 4.3 |
| Body mass (Kg) | 80.2 ± 28.2 | 79.5 ± 25.8 |
| Height (m) | 1.74 ± 0.1 | 1.69 ± 0.0 |
| BMI (Kg/m$^2$) | 25.7 ± 6.3 | 27.5 ± 7.4 |
| Men/woman | 5/4 | 4/4 |
| Time of training (years) | 10.5 ± 4.1 | 12.1 ± 4.4 |

Figure 31:
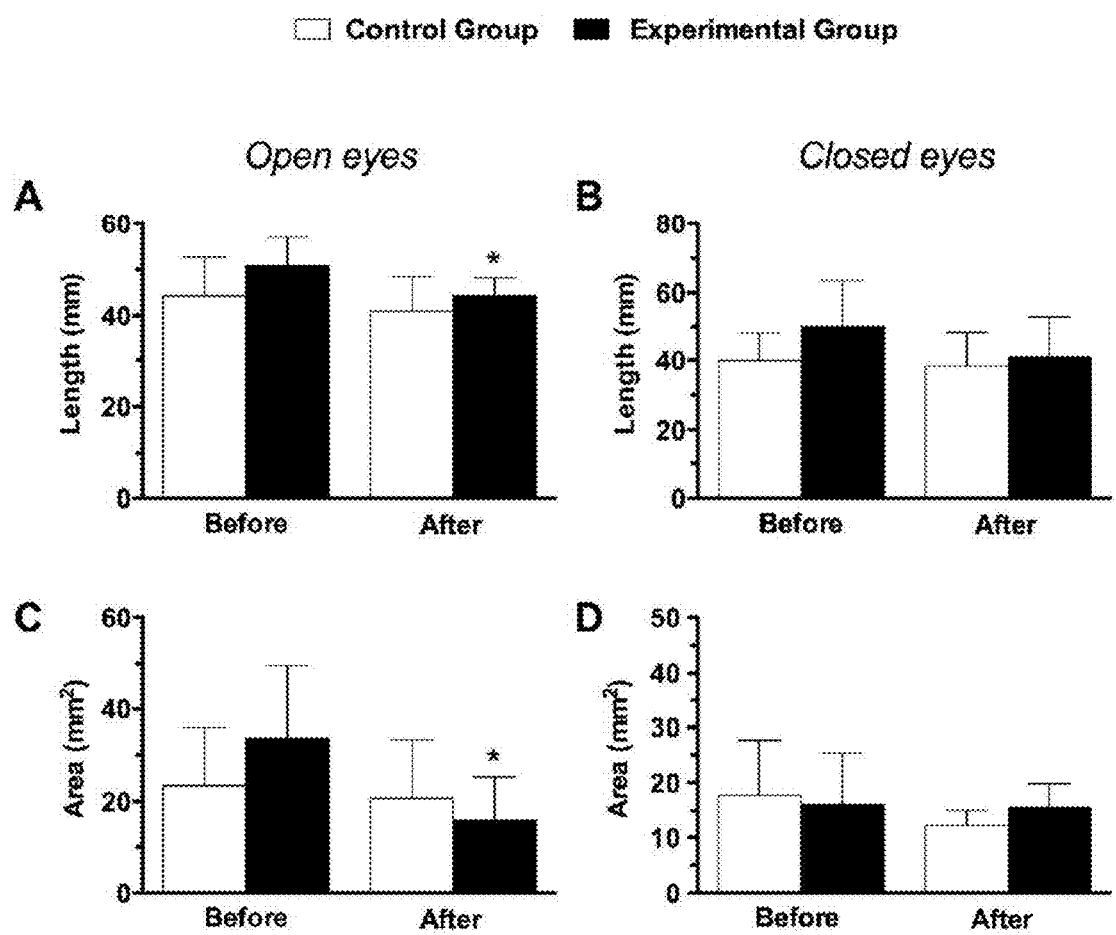
FIG. 31 is a graph illustrating the effect of far-infrared emitting bioceramic apparel on on postural control.

FIG. 31 is a graph illustrating the effect of far-infrared emitting bioceramic apparel on postural control. FIG. 31 displays the results of the variables before and after treatment with placebo FIR or with FIR, with the values expressed as the mean and standard deviation. The total length and area of oscillation of the COP underwent a reduction following treatment in the experimental group, with different degrees of reduction when the eyes were open ($p<0.05$) but not closed ($p>0.05$). Reduction in body oscillations in the control group following placebo treatment with the eyes open and closed ($p>0.05$) was not observed. These findings demonstrate that FIR interventions led to lesser body oscillation and, consequently, greater orthostatic control.

Furthermore, as shown in TABLE 2, the experimental group exhibited a reduction in mediolateral and anterior-posterior deviations (width) of the COP following treatment in open eyes analysis, thereby demonstrating greater orthostatic control, whereas no significant difference was found in the control group ($p>0.05$). The mediolateral and anterior-posterior deviations average speed analysis revealed no statistically significant differences between groups ($p>0.05$).

Conclusion: These findings demonstrate that FIR intervention led to lesser body oscillation and, consequently, greater orthostatic control. The results obtained herein suggest that FIR garments may find practical clinical applications in balance disorders or even for performance enhancing apparel in both leisure activities and competitive sports.

Example 36: Effect of Far-Infrared Emitting Bioceramic Apparel on Human Subjects Undertaking a Pilates Exercise Regimen Objectives: to investigate the effect of far-infrared emitting ceramic apparel on the flexibility, grip strength, balance, heart rate variability, and quality of sleep.

Study Design: Double-blind, placebo controlled trial.

Intervention: Participants followed a beginner Pilates protocol of one hour session, three times a week for a period of eight weeks and were randomly divided in 2 different groups (placebo and bioceramic). Placebo group wore a sham far-infrared emitting ceramic shirt (no bioceramics) while bioceramic group participants wore a bioceramic shirt that emits far-infrared energy for 8 weeks every night during sleep (6 to 8 hours).

Evaluations:

Sample size and population: 30 participants: 15 individuals in each group. Even distribution between sexes/ages.

Flexibility: the sit-and-reach bench test was used to measure flexibility. A baseline evaluation was conducted before the beginning of the tests and before every Pilates session (3 times a week for eight weeks). Grip Strength: a hand dynamometer was used to measure grip strength. A baseline evaluation was conducted before the beginning of the tests and before every Pilates session (3 times a week for eight weeks). Balance: balance was evaluated with a stabilometry/baropodometry platform (S-Plate-Medicapteurs, France). A baseline evaluation before the beginning of the tests and after six weeks.

Figure 32:
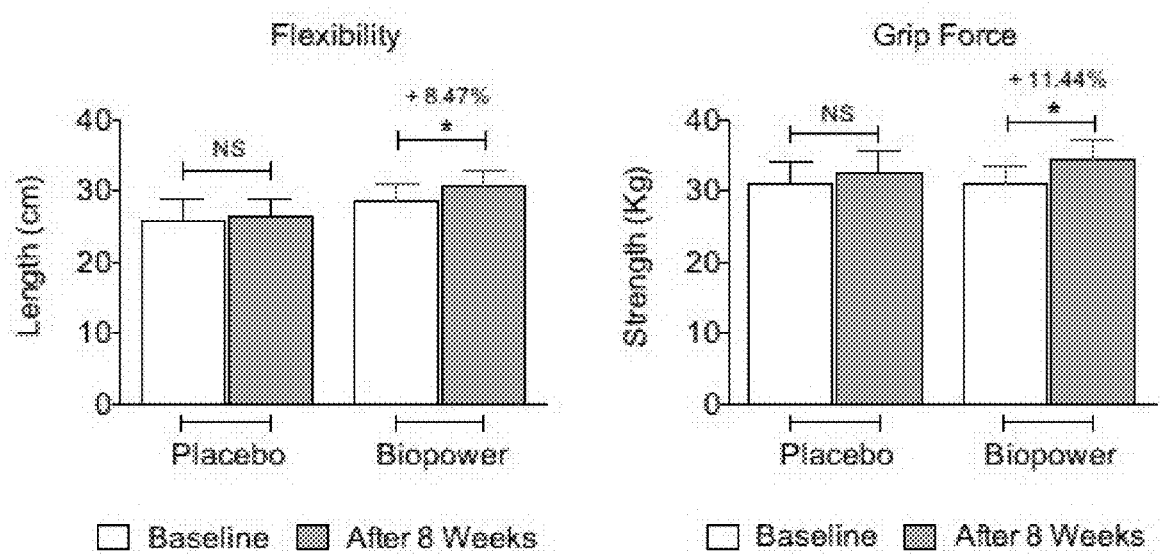
FIG. 32 is a graph illustrating the effect of far-infrared emitting bioceramic apparel on the flexibility and grip strength of pilates practitioners.

FIG. 32 is a graph illustrating the effect of far-infrared emitting bioceramic apparel on the flexibility and grip

TABLE 2

Analysis with open eyes

| Deviation | Control Group | | Experimental Group | |
| --- | --- | --- | --- | --- |
|  | Before | After | Before | After |
| Mediolateral - width (mm) | 4.750 ± 2.308 | 7.060 ± 2.092 | 4.310 ± 2.617 | 4.500 ± 1.619* |
| Mediolateral - average speed (mm/s) | 1.100 ± 0.2160 | 1.300 ± 0.2280 | 1.010 ± 0.1853 | 1.117 ± 0.0408 |
| Anterior-posterior - width (mm) | 5.350 ± 2.178 | 6.633 ± 2.181 | 4.250 ± 2.611 | 4.217 ± 1.333* |
| Anterior-posterior - average speed (mm/s) | 1.200 ± 0.673 | 1.583 ± 0.879 | 1.040 ± 0.607 | 0.950 ± 0.314 |

TABLE 3 shows the FIR treatment had no effect on orthostatic control in the mediolateral and anterior-posterior deviations in all analyzed parameters in human subjects with closed eyes (width and average speed) when compared with placebo FIR.

TABLE 3

Analysis with closed eyes

| Deviation | Control Group | | Experimental Group | |
| --- | --- | --- | --- | --- |
|  | Before | After | Before | After |
| Mediolateral - width (mm) | 3.522 ± 2.228 | 3.533 ± 2.856 | 3.630 ± 2.412 | 4.350 ± 1.773 |
| Mediolateral - average speed (mm/s) | 0.960 ± 0.231 | 1.217 ± 0.337 | 0.910 ± 0.213 | 1.000 ± 0.281 |
| Anterior-posterior - width (mm) | 4.556 ± 4.005 | 4.183 ± 3.056 | 3.0 ± 1.272 | 4.133 ± 1.475 |
| Anterior-posterior - average speed (mm/s) | 1.200 ± 1.715 | 1.467 ± 1.480 | 0.790 ± 0.568 | 0.850 ± 0.301 | strength of pilates practitioners. Baseline evaluations were performed once a week before any intervention. *p<0.05 when comparing with baseline evaluation (T-Test 95% confidence interval—Graphpad Prism software, USA, 2014). The results of FIG. 32 indicate that the use of bioceramic shirts in combination with Pilates sessions statistically increased the participants flexibility and grip force.

Figure 33:
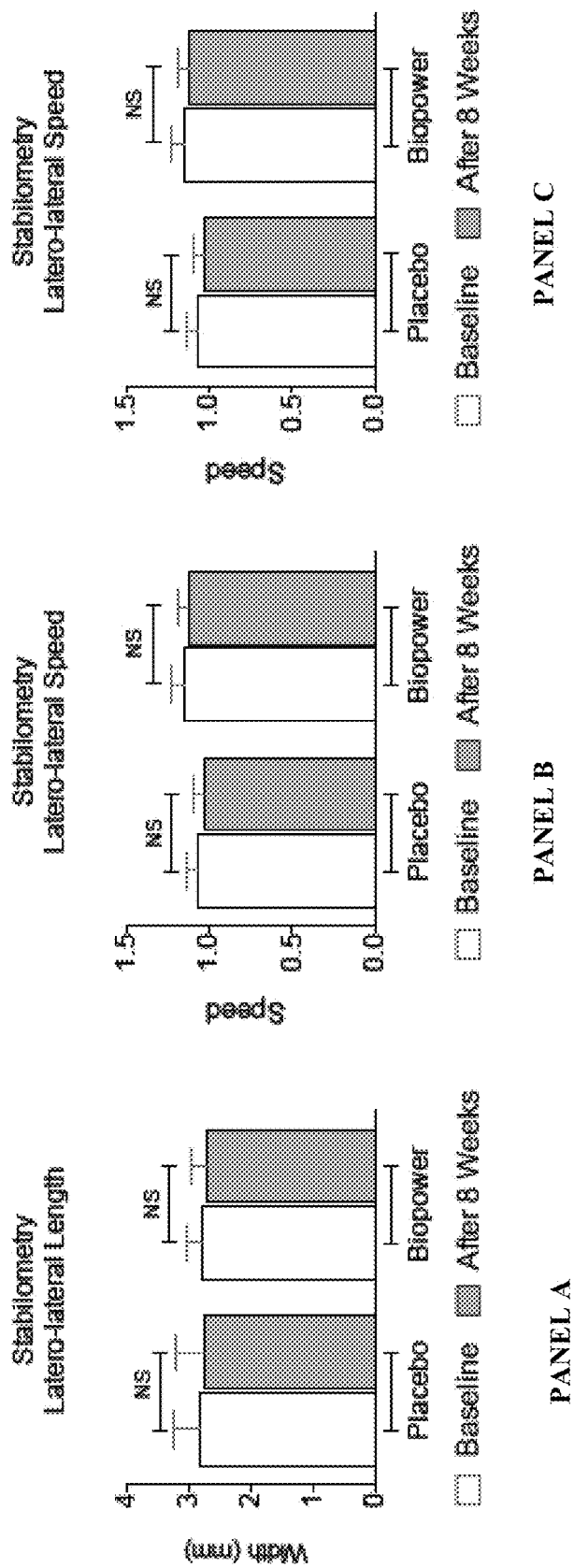
FIG. 33 is a graph illustrating the effect of far-infrared emitting bioceramic apparel on the stabilometry (laterolateral) of pilates practitioners.
Figure 34:
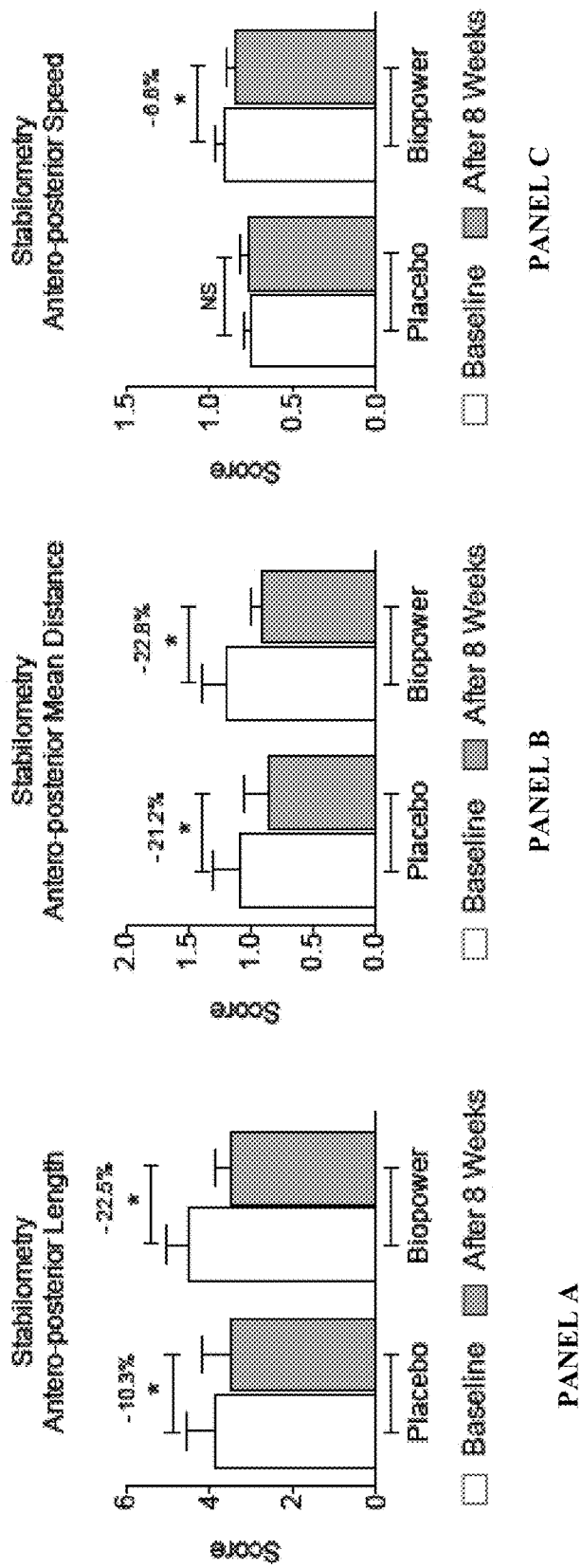
FIG. 34 is a graph illustrating the effect of far-infrared emitting bioceramic apparel on the stabilometry (anteroposterior) of pilates practitioners.

FIGS. 33 and 34 are graphs illustrating the effect of far-infrared emitting bioceramic apparel on the stabilometry of pilates practitioners. FIG. 33 is a graph illustrating the effect of far-infrared emitting bioceramic apparel on the stabilometry (latero-lateral) of pilates practitioners: latero-lateral length (Panel A), latero-lateral distance (Panel B), latero-lateral speed (Panel C). FIG. 34 is a graph illustrating the effect of far-infrared emitting bioceramic apparel on the stabilometry (antero-posterior) of pilates practitioners: antero-posterior length (Panel A), antero-posterior distance (Panel B), antero-posterior speed (Panel C). *p<0.05 indicates statistically significant difference between groups. Baseline evaluations were performed once a week before any intervention. (paired T-Test 95% confidence interval—Graphpad Prism software, USA, 2014). The results shown in FIGS. 33 and 34 indicate that the use of bioceramic shirts in combination with Pilates sessions statistically reduced anteroposterior oscillation—overall length, distance from center and speed, whereas the use of placebo shirts statistically affected (to a lesser extent) overall length and distance from center.

Figure 35:
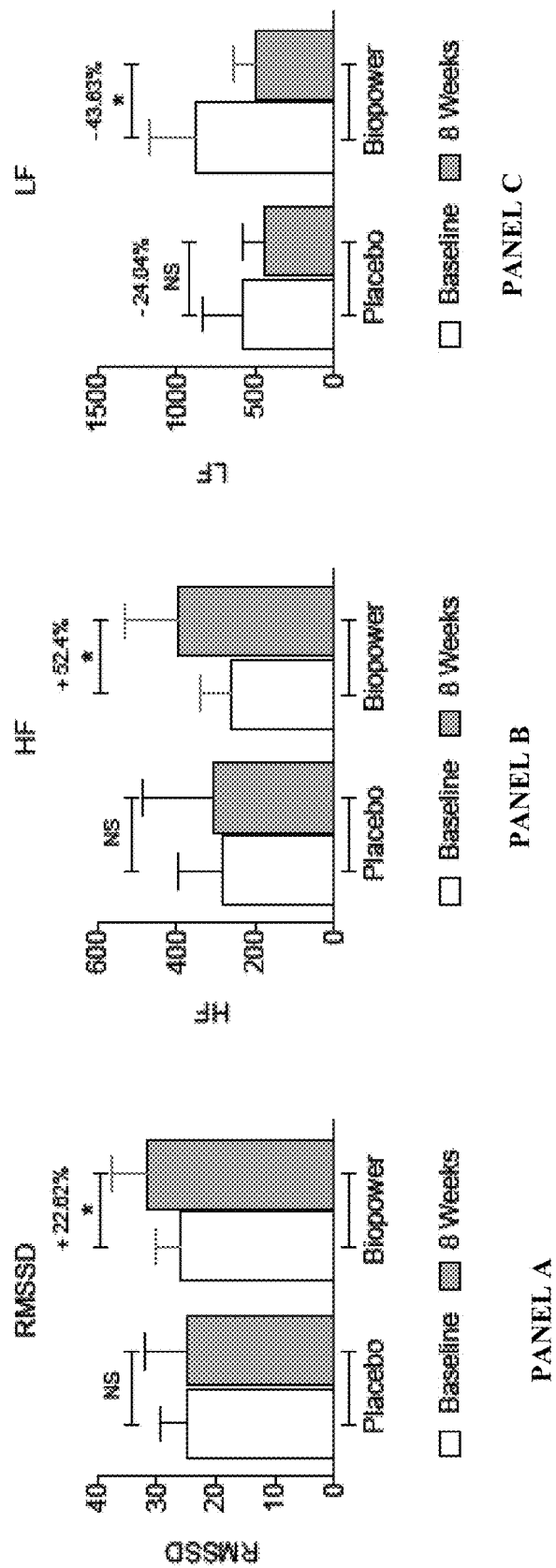
FIG. 35 illustrates the effect of far-infrared emitting bioceramic apparel on the heart rate variability (HRV) of pilates practitioners.

Heart rate variability (HRV): heart rate was evaluated with the nerve express unit (Valley Stream, N.Y., USA). A baseline evaluation before the beginning of the tests and after eight weeks. FIG. 35 illustrates the effect of far-infrared emitting bioceramic apparel on the heart rate variability (HRV) of pilates practitioners. Heart rate variability was evaluated with the nerve express unit (Valley Stream, N.Y., USA). The results of FIG. 35 indicate that indicate that the use of far-infrared emitting bioceramic shirts increased rMSSD and HF (High Frequency Power) as well as decreased LF (Low Frequency Power). The combination of these results indicate an overall increase of the activity of the parasympathetic autonomic nervous system and decrease in the sympathetic branch. (in this case, an increase in the activity of the parasympathetic and a decrease in the activity of the sympathetic indicate a more beneficial result). The RMSSD (The square root of the mean squared difference between adjacent N-N intervals): commonly used as an index of vagally (Vagus Nerve) mediated cardiac control, which captures respiratory sinus arrhythmia (RSA), the frequent changes in heart rate occurring in response to respiration. RMSSD is an accepted measure of parasympathetic activity and correlates with HF of frequency domain analysis. High Frequency Power is a marker of Parasympathetic Activity. Low Frequency Power is a marker of both Parasympathetic and Sympathetic Activity.

Figure 36:
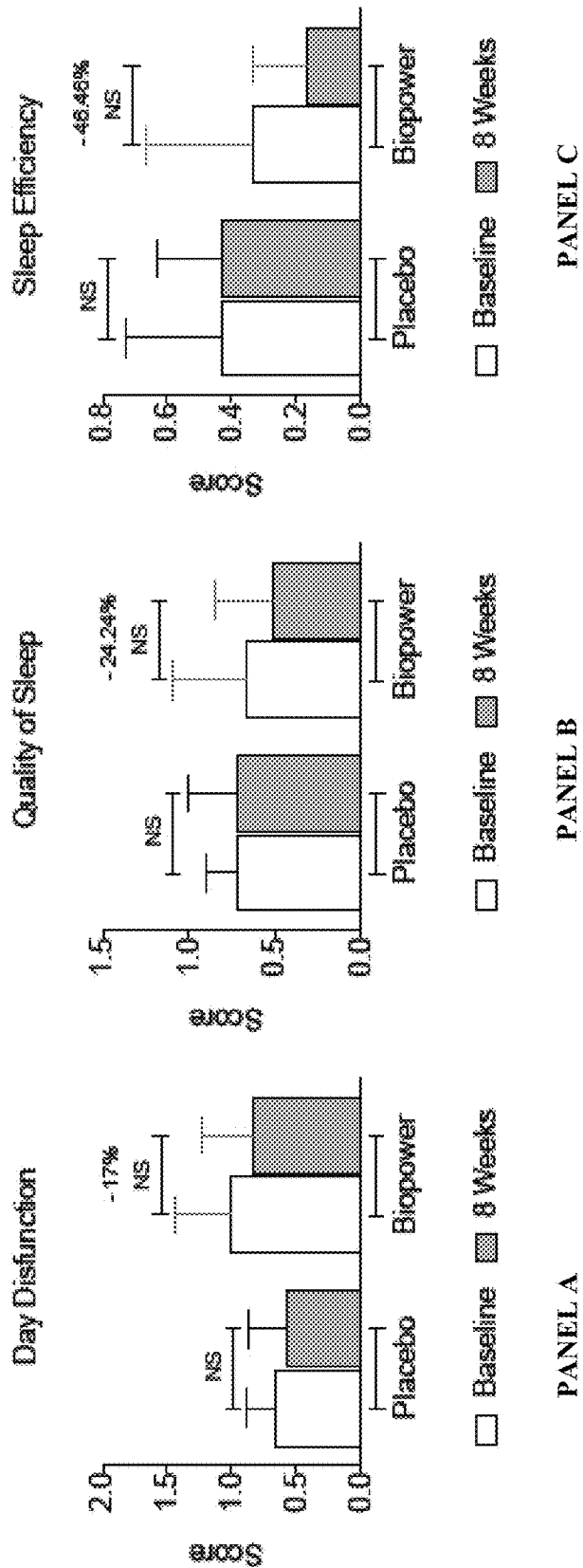
FIG. 36 illustrate the results of far-infrared emitting bioceramic apparel on day dysfunction (Panel A), quality of sleep (Panel B), and sleep efficiency (Panel C).
Figure 37:
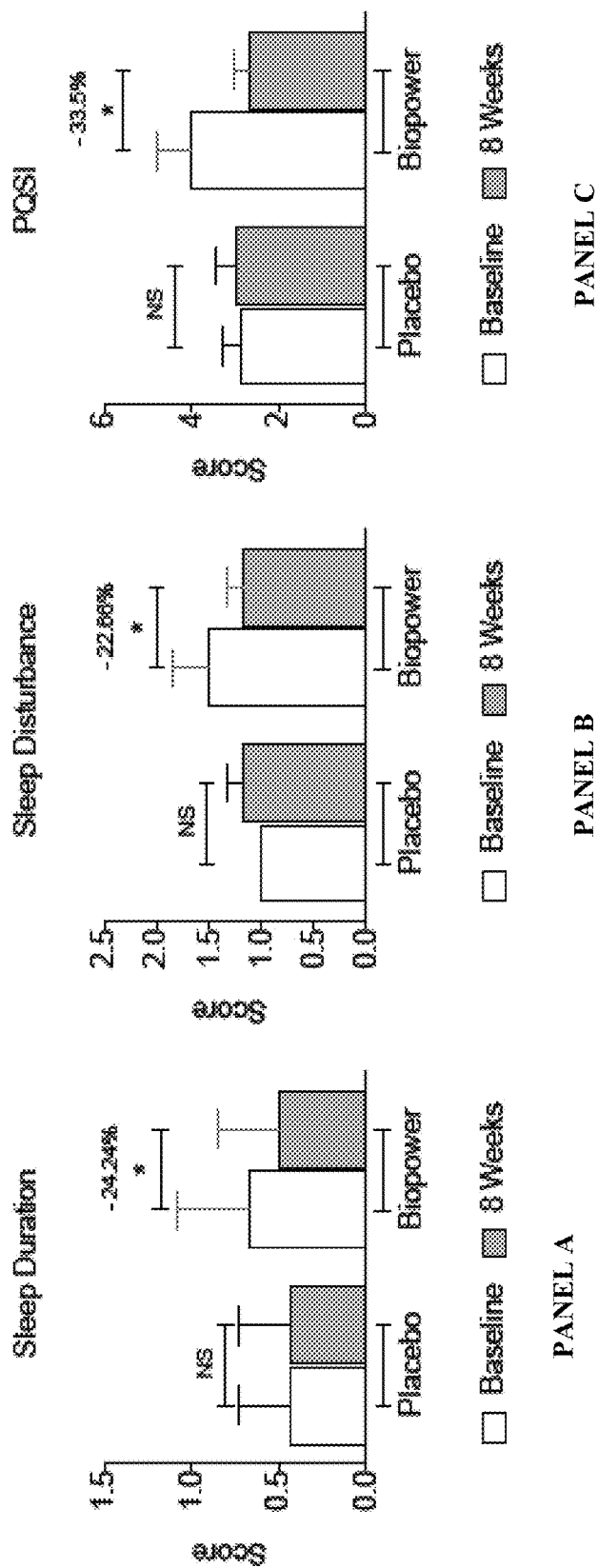
FIG. 37 illustrate the results of far-infrared emitting bioceramic apparel on sleep duration (Panel A), sleep disturbance (Panel B), and PQSI (Panel C).

Quality of Sleep: quality of sleep was evaluated with the The Pittsburgh Quality of Sleep Questionnaire. A baseline evaluation before the beginning of the tests and after eight weeks. FIGS. 36 and 37 illustrate the results of the Pittsburgh Quality of Sleep Questionnaire. *p<0.05 when compared with baseline evaluation (paired T-Test 95% confidence interval—Graphpad Prism software, USA, 2014). Several parameters were evaluated including day dysfunction (FIG. 36 Panel A), quality of sleep (FIG. 36 Panel B), sleep efficiency (FIG. 36 Panel C), sleep duration (FIG. 37 Panel A), sleep disturbance (FIG. 37 Panel B), and PQSI (FIG. 37 Panel C).

Results: Results presented in FIG. 4 indicate that the use of far-infrared emitting bioceramic shirts decreased the following indexes (a lower index indicates a more beneficial result): Sleep Duration: Minimum Score=0 (better); Maximum Score=3 (worse); Sleep Disturbance: Minimum Score=0 (better); Maximum Score=3 (worse); Overall Quality of Sleep: Minimum Score=0 (better); Maximum Score=3 (worse); and The Pittsburgh Quality of Sleep Questionnaire: Minimum Score=0 (better); Maximum Score=21 (worse).

Conclusion: The use of far-infrared emitting bioceramic shirts during sleep increased the duration of sleep and its efficiency, increased the activity of the parasympathetic nervous system as well as decreased the activity of the sympathetic, that can be associated with a more relaxed and better quality sleep. Our studies have demonstrated that far infrared (FIR) produced by Bioceramics promotes microcirculation (A), induces reduction of muscular fatigue (B), reduces the effects of stress (C) as well as promotes analgesia and the decrease of inflammatory conditions (D); it is possible that the combination of these effects leads to a more relaxed and effective sleep.

Example 37: Effect of Far-Infrared Emitting Bioceramic Apparel on Weight Loss, Changes in Body Measurements, and Cellulite Reduction Objectives: to investigate the effect of shorts comprising bioceramics on weight loss, changes in body measurements, and cellulite reduction.

Study type: randomized, double-blind, placebo controlled. Females randomly allocated to an experimental group (cFIR group, participants are asked to wear shorts impregnated with FIR emitting ceramic material); and a control group (control group, participants are asked to wear shorts that are impregnated with a sham ceramic material, i.e.: a ceramic material that does not provide far infrared energy). Randomization numbers are optionally generated in a randomization site (randomization.com).

Materials and Methods: 30 healthy adult women with moderate to severe cellulite (cellulite score of at least II out of IV) as assessed by a physician investigator are randomized in either the experimental group or the control group (15 participants in each group). Participants are blinded as to which group they have been assigned. Participants wear the shorts daily for at least 6 hours a day for a period of 6 weeks.

Exclusion Criteria Include:
participants that have received treatment for cellulite reduction in the thighs within one month of the start time of the study;
participants with a history of deep vein thrombosis within the past two years;
participants with a history of congestive heart failure;
participants diagnosed with exclusive arterial disease of the legs;
pregnant or lactating participants;
participants that have used a topical medication usage (e.g.: corticosteroids) within two weeks of the study period;

Parameters to be evaluated: initial, i.e. baseline, weight, cellulite and body measurements are measured for each participant prior to the start of the study. Follow up measurements are taken approximately every two weeks from the start day of the study. Specific parameters being evaluated include:
weight or body mass index (BMI: weight in kilograms divided by height in meters, squared).

thigh circumference. The measure of thigh circumference at set points with a flexible ruler can give an indirect measurement of localized fat and possibly relates to cellulite. Thigh circumference measurements will be taken of both legs at 18 cm and 26 cm from the superior pole of the patella for the lower and upper thigh, respectively, using a flexible measuring ruler.

cellulite observation. Direct or photographic visualization of skin irregularities such as puckering, dimpling, and nodularities is used to evaluate levels of cellulite. High-quality color digital photographs are taken of the posterior and lateral thighs by an investigator at the following angles:
(a) 90° right thigh (b) 45° right thigh (c) 180° right thigh (d) 90° both thighs
(e) 90° left thigh (f) 45° left thigh (g) 180° left thigh Photographs are reviewed by five blinded, independent board-certified dermatologists.

skin elasticity. Measurement of skin tension with a suction elastometer can give an estimate of the resilience of the dermis, a function of connective tissue helping to gauge the amount of cellulite present.

Skin electrical conductivity. Electrical conductivity is used to measure tissue resistance to electron flow and determine specific percentages of body composition (lean mass, fat mass, water).

Example 38: Effect of Far-Infrared Emitting Bioceramic Apparel on Muscle Recovery and Delayed Onset Muscle Soreness Objectives: to investigate the effect of bioceramics bottoms (shorts) on muscle recovery after muscle damage protocol (strength), delayed onset muscle soreness, blood levels of CK (creatine kinase) and LDH (lactate dehydrogenase), blood levels of inflammatory and anti-inflammatory cytokines (TNF-α, IL-6, IL-1β, IL-10 and IL-4), and blood levels of oxidative stress as well as of anti-oxidative enzymes activity (TBARS Carbonyls, SOD and catalase).

Study type: double-blind, placebo controlled.

Intervention: subjects are randomly divided into 2 groups (placebo and bioceramics). Subjects in the placebo group wear sham bottoms (no bioceramics) while participants in the bioceramics group wear bottoms comprising far-infrared emitting bioceramics. Subjects in both groups wear the intervention for a period of two hours immediately following the start of the damage protocol (day 0). Subjects also wear the bottoms for additional periods of two hours starting at day 1 (24 hours following the start of the muscle damage protocol), day 2 (48 hours following the start of the muscle damage protocol), and day 3 (72 hours following the start of the muscle damage protocol) later.

Evaluations:

a) Muscle recovery after muscle damage protocol: quadriceps strength is evaluated with isokinetic equipment (De Queen, Ark., USA). A baseline evaluation is conducted before the beginning of the tests, immediately after the muscle damage protocol, and on days 1, 2, and 3 (after the use of the bottoms).

b) Delayed onset muscle soreness is calculated with a visual analog scale for pain (VAS) questionnaire. A baseline evaluation is conducted before the beginning of the tests, immediately after the muscle damage protocol, and on days 1, 2, and 3 (after the use of the bottoms).

c) Blood levels of CK (creatine kinase) and LDH (lactate dehydrogenase), inflammatory and anti-inflammatory cytokines (TNF-α, IL-6, IL-1β, IL-10 and IL-4), oxidative stress markers and anti-oxidative enzymes activity (TBARS Carbonyls, SOD and catalase) are measure with biochemical analyses (ELISA). A baseline evaluation is conducted before the beginning of the tests, immediately after the muscle damage protocol, and on days 1, 2, and 3 (after the use of the bottoms).

Sample size and population: 30 participants: 15 individuals in each group. Even distribution between sexes/ages.

Example 39: Evaluation of the Biomodulation Induced by the Use of Infrared Emitting Ceramic Shirts in Patients with Chronic Obstructive Pulmonary Disease (COPD)

Objectives: this study evaluated the biomodulatory effects induced by the use of shirts impregnated with cFIR in patients with Chronic Obstructive Pulmonary Disease (COPD). COPD is defined as a chronic and progressive reduction in the airflow, secondary to an abnormal inflammatory response of the lungs. One of the features of COPD is the reduction of aerobic capacity and muscle strength, which leads to loss of functionality and exercise intolerance, negatively impacting upon the patient's quality of life.

Inclusion criteria: subjects diagnosed with COPD of both sexes were recruited according to the following criteria: present clinical diagnosis of COPD and age (subjects were older than 40 years of age).

Exclusion criteria: present incapacitating comorbidity and/or exacerbations of the COPD in the last 6 months.

For treatment, t-shirts impregnated with a bioceramic of the BioPower® brand were used. The participants wore the t-shirts at night (6-8 hours) for 3 consecutive weeks. The evaluations were performed pre- and post-treatment. In order to classify the functional clinical status of each patient the modified Medical Research Council Dyspnoea Scale (mMRC) was used. To assess functional capacity the London Chest Activity of Daily Living scale (LCADL) and the six-minute walk test (6MWT) were used. The activity of the autonomic nervous system was assessed by the analysis of heart rate variability. 13 patients were recruited and there were 3 dropouts. Thus, the sample consisted of 10 individuals with COPD, with an average of 63.70 years of age, mean BMI of 26.19 kg/m2, smoking history of 24.41 years/pack. 40% of the sample were female and 60% male.

Figure 38:
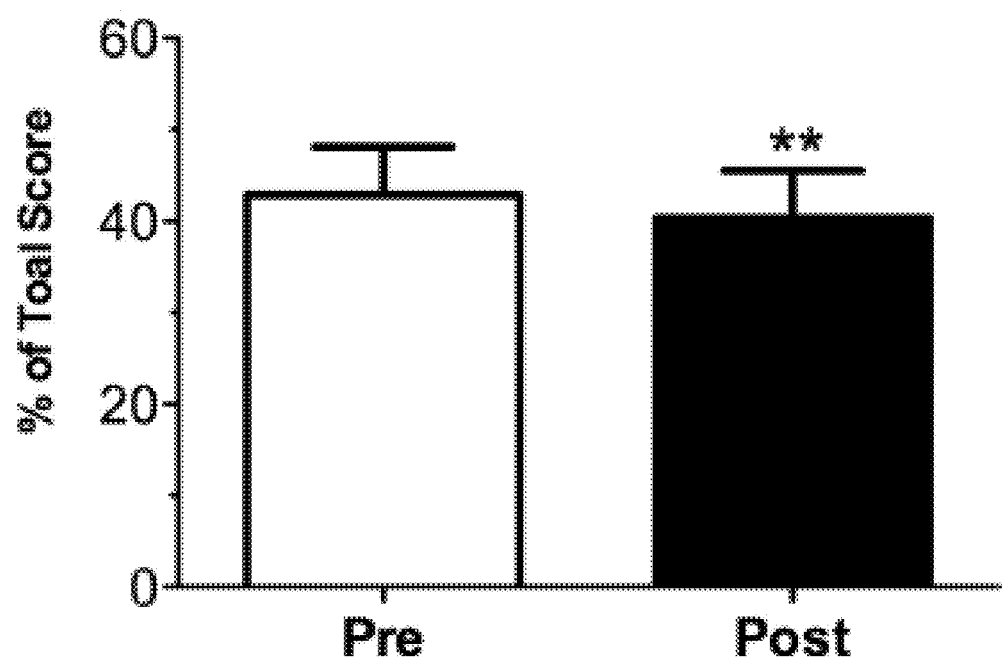
FIG. 38 illustrate the results London Chest Activity of Daily Living Questionnaire (LCADL) in subjects afflicted with Chronic Obstructive Pulmonary Disease (COPD).

The LCADL questionnaire analysis indicated that patients experienced a statistically significant improvement ($p<0.01$) when compared with their pretreatment conditions (FIG. 38). In pretreatment analyses patients had a mean proportion of the total score of 42.88% and 40.36% in the post-treatment assessment.

Figure 39:
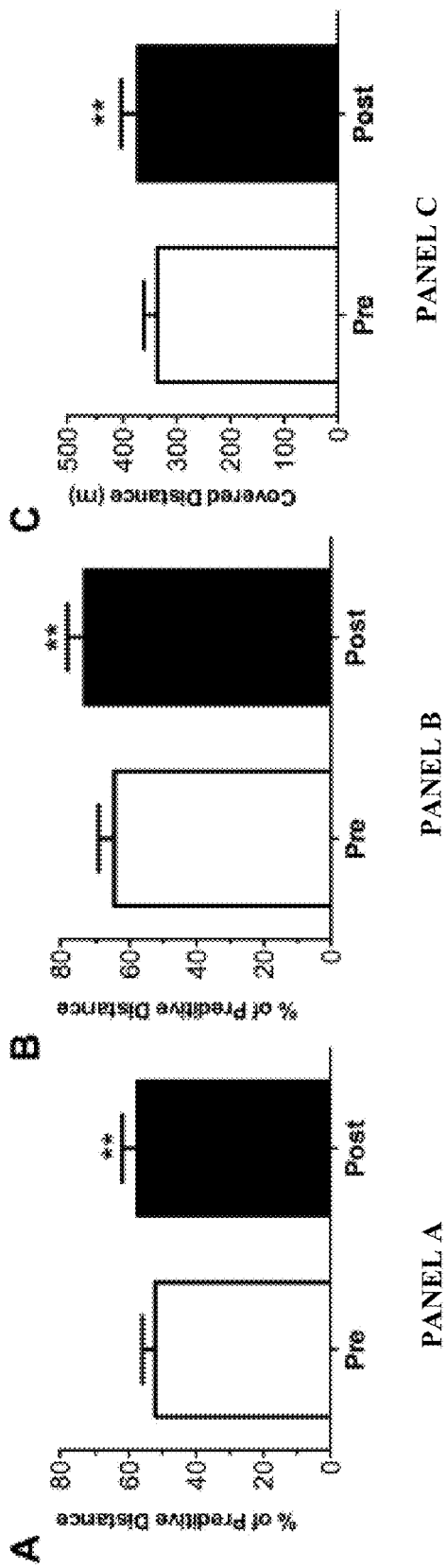
FIG. 39 illustrate the results of the performance-based functional exercise capacity test in subjects afflicted with Chronic Obstructive Pulmonary Disease (COPD).

In the 6MWT, using the BMI reference in equation 1, the patients showed an increase of 5.37% of the predicting distance. FIG. 39 illustrate the results of the 6MWT (performance-based functional exercise capacity test) with equation 1 (PANEL A), equation 2 (PANEL B) and distance walked before and after treatment (PANEL C). The columns represent the mean values of 10 patients and the verticle lines correspond to the standard error of the mean (SEM). **$P<0.01$ when comparing pre to post-treatment condition (paired t-test). These data were corroborated with the analysis of the equation 2 (using the ΔHR in the reference equation), in which the increased 8.32% the predicting distance. Furthermore, the results showed an increase of 36 meters when compared to the pretreatment evaluation.

Figure 40:
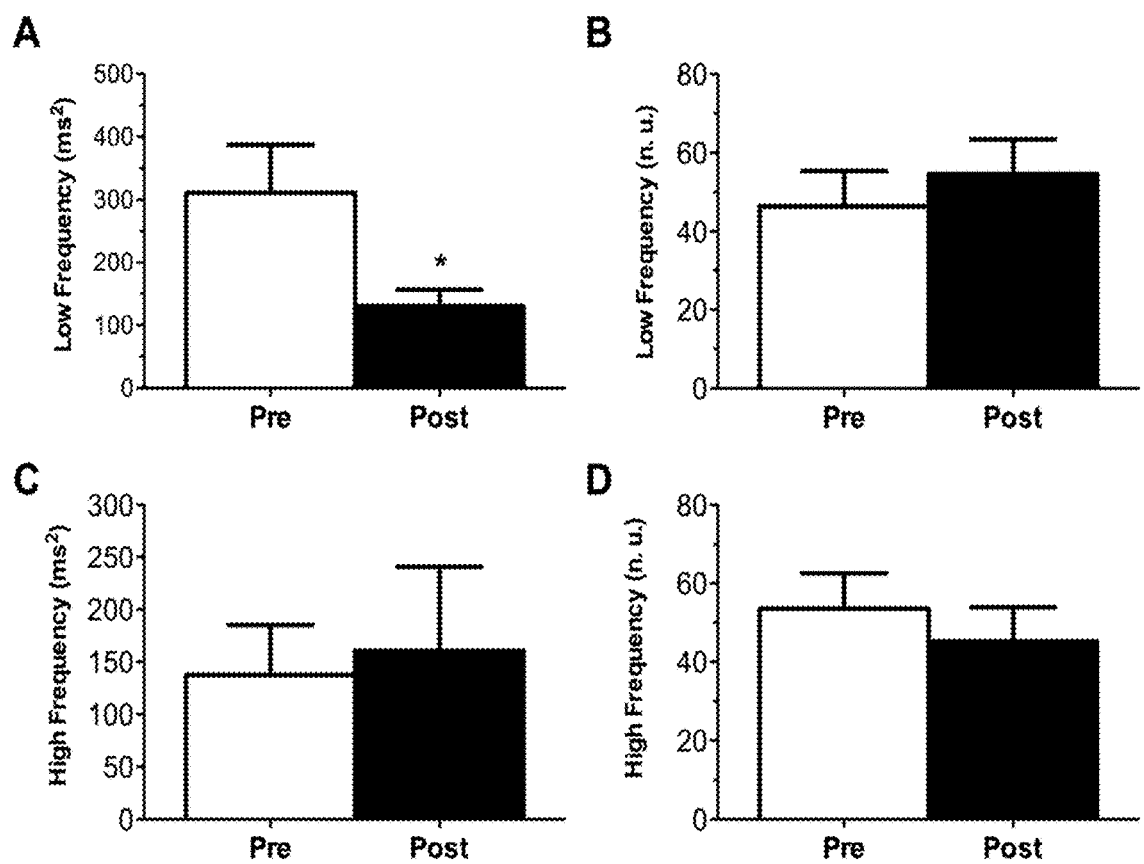
FIG. 40 illustrate the results of a heart rate variance test (HRV) (frequency domain) in subjects afflicted with Chronic Obstructive Pulmonary Disease (COPD) before and after treatment with a bioceramic.

FIG. 40 illustrate the results of the heart rate variance (frequency domain) of COPD patients assessed before and after treatment. (PANEL A) Low frequency (ms2), (PANEL B) low frequency (nu), (PANEL C) high frequency (ms2), (PANEL D) high frequency (nu). The columns represent the mean values of 10 patients and the vertical lines correspond to the standard error of the mean (SEM). **P<0.01 when comparing pre to post-treatment condition (paired t-test).

Figure 41:
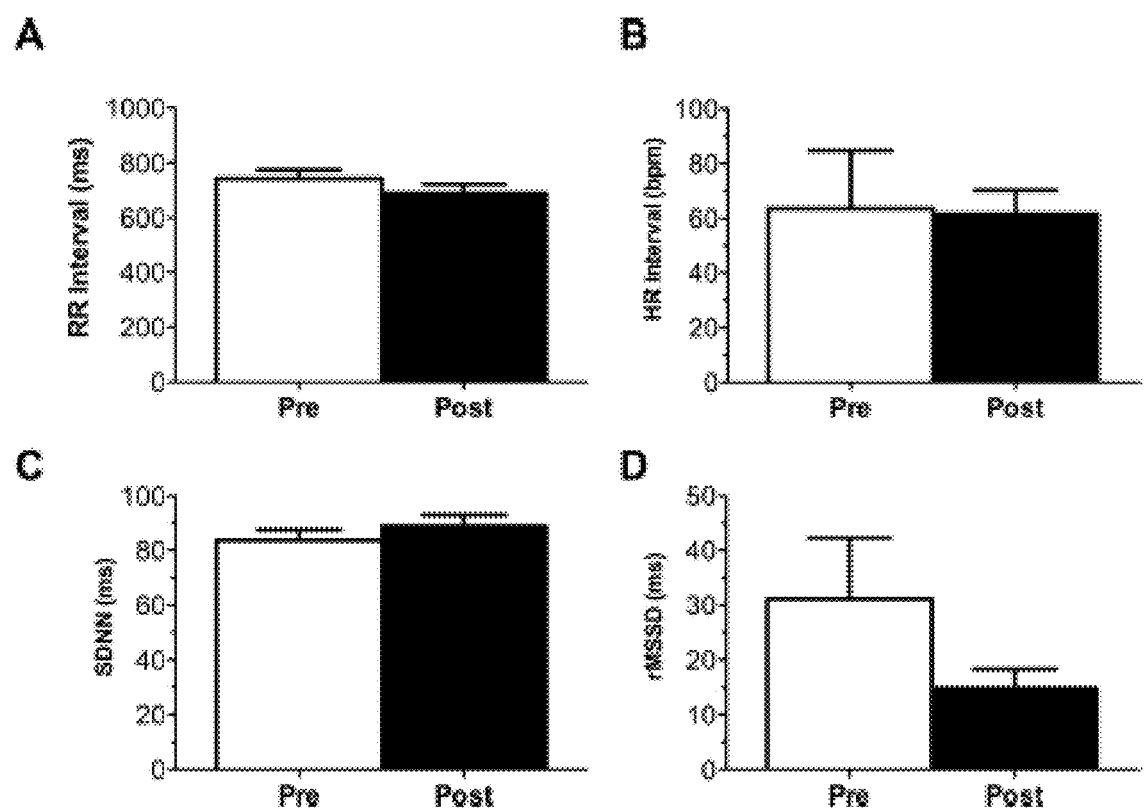
FIG. 41 illustrate the results of a heart rate variance test (HRV) (time domain) in subjects afflicted with Chronic Obstructive Pulmonary Disease (COPD) before and after treatment with a bioceramic.

FIG. 41 illustrate the results of the heart rate variance (time domain) of COPD patients assessed before and after treatment. (PANEL A) RR intervals (PANEL B) HR, intervals (PANEL C) component SDNN, (PANEL D) rMSSD. The columns represent the mean values of 10 patients and the vertical lines correspond to the standard error of the mean (SEM). **P<0.01 when comparing pre to post-treatment condition (paired t-test).

The heart rate variability analyses, showed a reduction in the low frequency parameters, indicating reduced activity of the sympathetic nervous system. Based on these data, far-infrared treatment through cFIR impregnated shirts increased performance-based functional exercise capacity, reduced daily limitations as well as the activity of the sympathetic nervous system in patients with COPD.

Example 40: Evaluation of the Effect of Far-Infrared Emitting Ceramic Shirts on Oxygen Consumption, Heart Rate and Quality of Sleep: Randomized, Double-Blind, Placebo Controlled Trial with Young Baseball Players Objectives: this study investigated the effect of far-infrared emitting ceramic shirts on oxygen consumption, heart rate and quality of sleep.

Study Design: Double-blind, placebo controlled trial.

Intervention: Participants were randomly divided in 2 different groups (Placebo and Biopower). Biopower group wore a Biopower far-infrared emitting ceramic shirt (with bioceramics) while the Placebo group participants wore a sham shirt (with bioceramics) for 6 weeks every night during sleep (6 to 8 hours).

Evaluations: a) Initial $VO_2$ consumption; b) Maximal oxygen consumption ($VO_2Max$); c) Aerobic Threshold (AeT); d) Anaerobic Threshold (AnT); e) Heart Rate (Initial, at VO2Max, AeT and AnT); and f) Quality of Sleep. Oxygen consumption and Heat rate assessments were conducted with the CardioCoach ($VO_2$ evaluation device—KORR Medical Technologies, Salt Lake City, Utah, USA). Quality of sleep was evaluated with the Pittsburgh Quality of Sleep Questionnaire. All participants were evaluated before the beginning of the tests (baseline) and after 6 weeks.

Sample size and population: 30 participants: 15 individuals in a control group (sham shirts) and 15 individuals in an experimental group (bioceramic shirts). All participants were healthy male baseball players.

Figure 42:
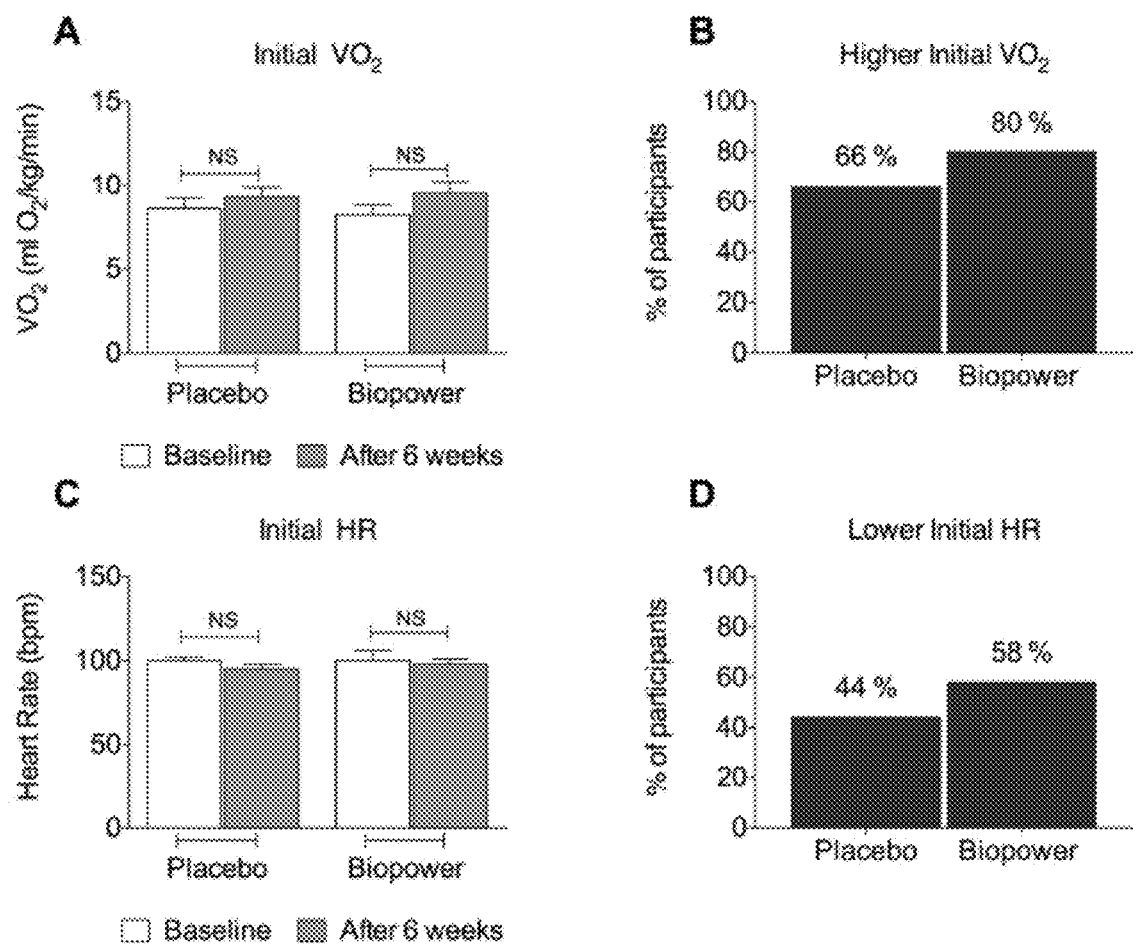
FIG. 42 illustrate the results on the initial $VO_2$ consumption of young baseball players exercising with bioceramic t-shirts or sham t-shirts.

FIG. 42 illustrates the results on the initial $VO_2$ consumption of young baseball players: PANEL A illustrates the initial $VO_2$ consumption. PANEL B illustrates the percentage of participants with higher initial $VO_2$. PANEL C illustrates the initial heart rate and PANEL D illustrates the percentage of participants with lower initial heart rate. Each column represents the mean of 12-15 participants, and the vertical lines indicate the S.E.M. NS stands for not statistically significant (T-Test 95% confidence interval—Graphpad Prism software, USA, 2014). The results presented in FIG. 42 PANEL A suggest that the use of bioceramic shirts increased initial $VO_2$ in a not statistically significant manner.

Figure 43:
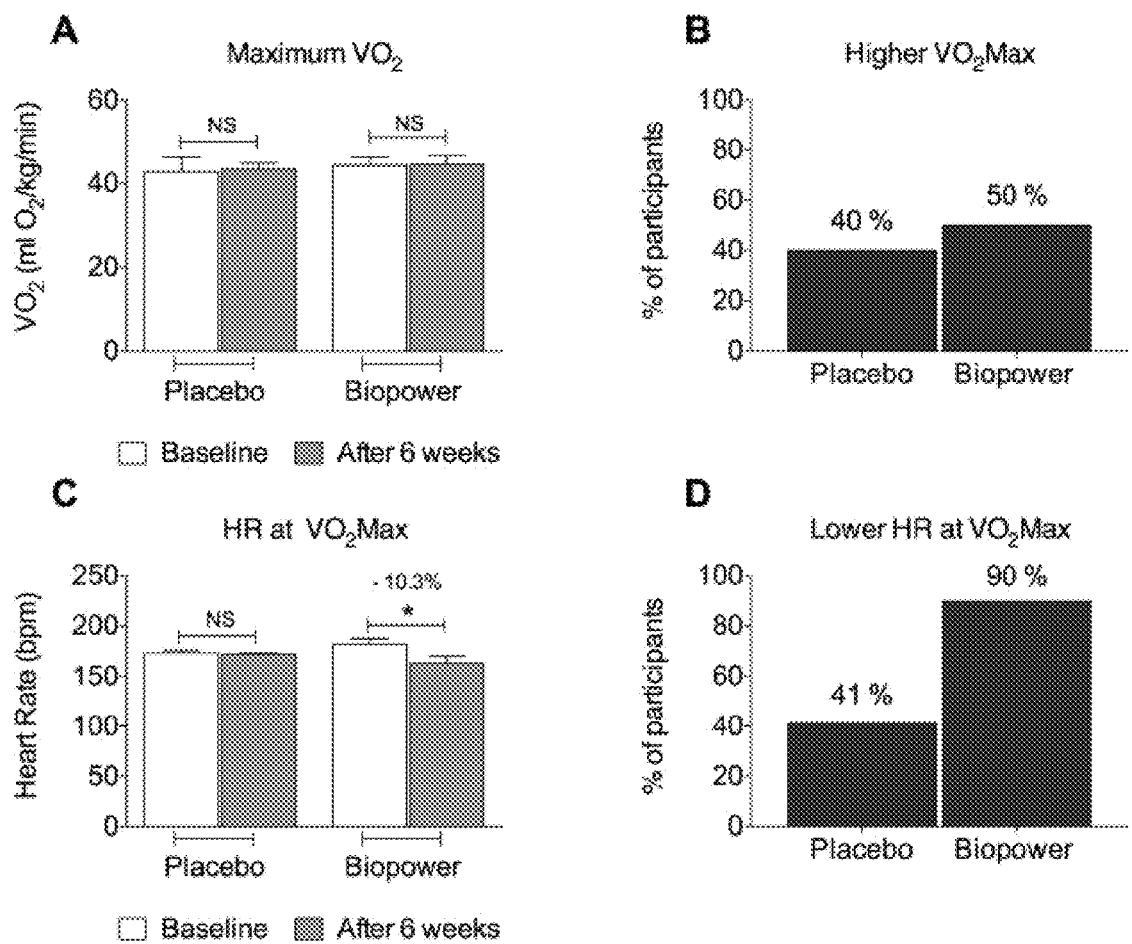
FIG. 43 illustrate the results on the initial $VO_2Max$ of young baseball players exercising with bioceramic t-shirts or sham t-shirts.

FIG. 43 illustrates the results of the $VO_2Max$ consumption of young baseball players: PANEL A illustrates the $VO_2Max$ and PANEL B illustrate the percentage of participants with higher $VO_2Max$. PANEL C illustrate the heart rate of subjects at $VO_2Max$ and PANEL D illustrate the percentage of participants with lower heart rate at $VO_2Max$. Each column represents the mean of 12-15 participants, and the vertical lines indicate the S.E.M. NS stands for not statistically significant. *p<0.05 when comparing with baseline evaluation (T-Test 95% confidence interval—Graphpad Prism software, USA, 2014). FIG. 43 PANEL C suggests that the use of biocermaic shirts decreased the participants heart rate at $VO_2Max$. In addition, a higher percentage of subjects in the group wearing bioceramic t-shirts presented higher $VO_2Max$ and lower heart rate than the Placebo group (PANELS B-D) when comparing baseline. Results were measured after 6 weeks for each group.

Figure 44:
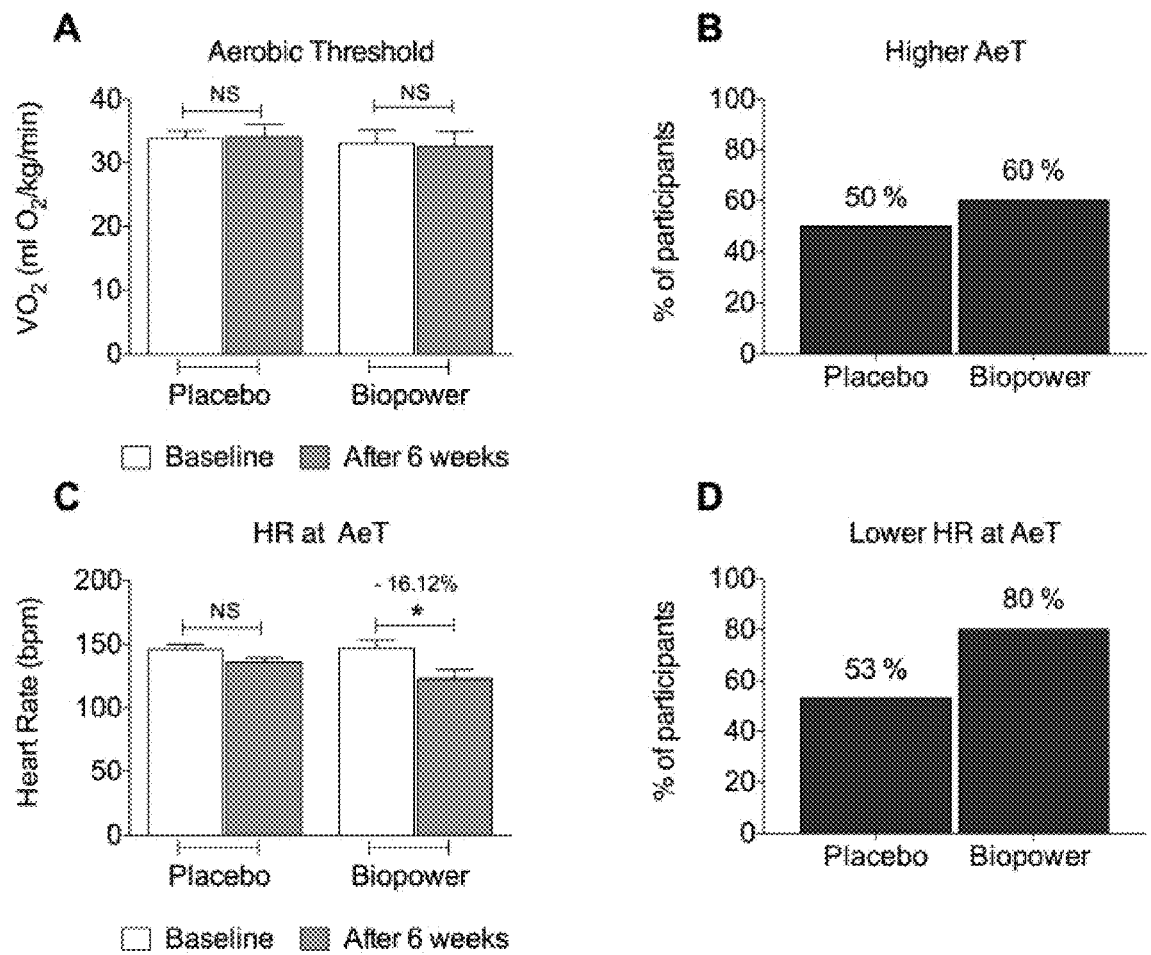
FIG. 44 illustrate the results of the aerobic threshold of young baseball players exercising with bioceramic t-shirts or sham t-shirts.

FIG. 44 illustrates the results of the aerobic threshold of young baseball players: PANEL A illustrates the aerobic threshold (AeT) and PANEL B illustrates the percentage of participants with higher AeT. PANEL C illustrates the heart rate at AeT and PANEL D illustrates the percentage of participants with lower heart rate at AeT. Each column represents the mean of 12-15 participants, and the vertical lines indicate the S.E.M. NS stands for not statistically significant. *p<0.05 when comparing with baseline evaluation (T-Test 95% confidence interval—Graphpad Prism software, USA, 2014). Results shown in FIG. 44 PANEL C suggest that the use of bioceramic shirts decreased the heart rate of subjects at AeT. Additionally, a higher percentage of subjects in the group wearing bioceramic t-shirts presented higher AeT and lower heart rate than the Placebo group (PANELS B-D) when compared with the baseline. Results were measured after 6 weeks for each group.

Figure 45:
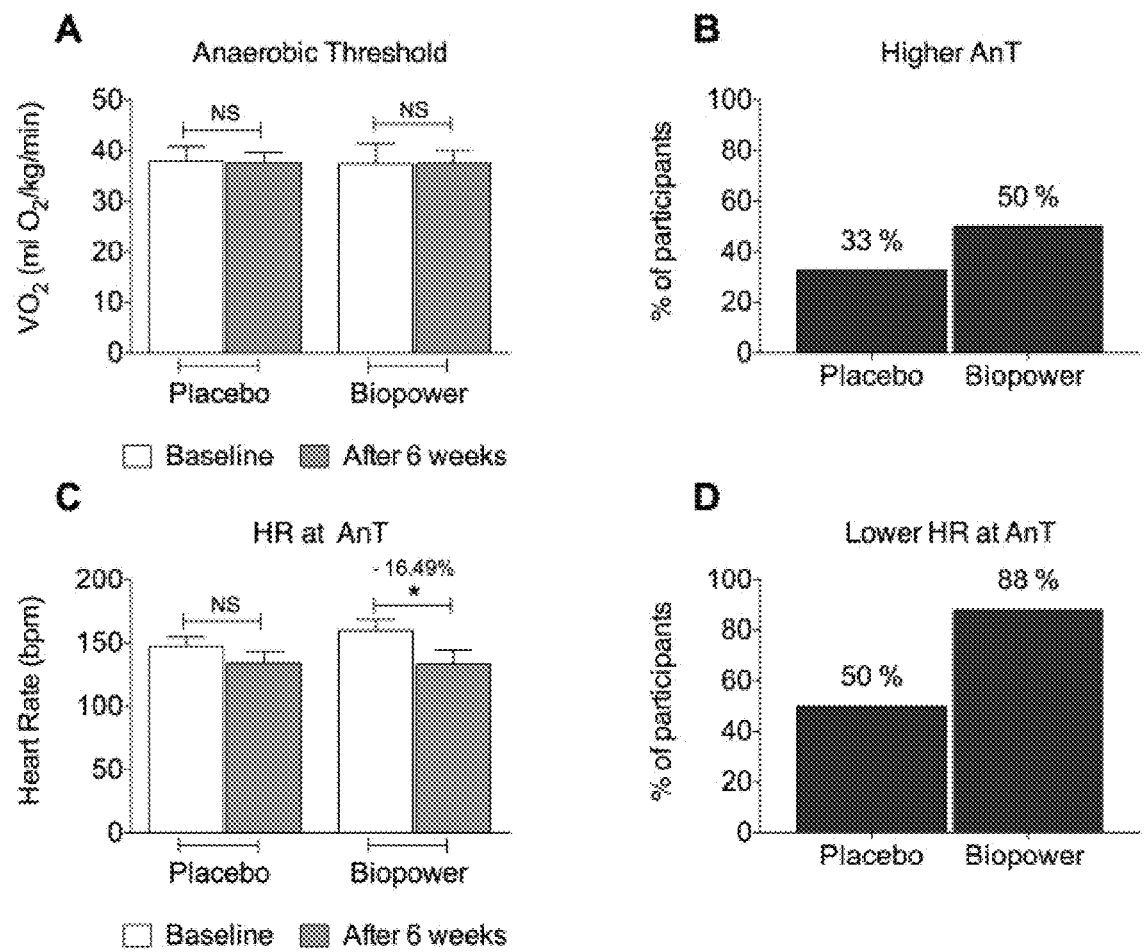
FIG. 45 illustrate the results of the anaerobic threshold of young baseball players exercising with bioceramic t-shirts or sham t-shirts.

FIG. 45 illustrates the results of the anaerobic threshold of young baseball players: PANEL A illustrates the anaerobic threshold (AnT) and PANEL A illustrate the percentage of participants with higher AnT. PANEL C illustrate the heart rate at AnT and PANEL D illustrate the percentage of participants with lower heart rate at AnT. Each column represents the mean of 12-15 participants, and the vertical lines indicate the S.E.M. NS stands for not statistically significant. *p<0.05 when comparing with baseline evaluation (T-Test 95% confidence interval—Graphpad Prism software, USA, 2014). Results shown in FIG. 44 PANEL C suggest that the use of bioceramic shirts decreased the participants heart rate at AnT. Additionally, a higher percentage of Biopower group participants presented higher AnT and lower heart rate than the Placebo group (PANELS B-D) when compared with the baseline. Results were measured after 6 weeks for each group.

Figure 46:
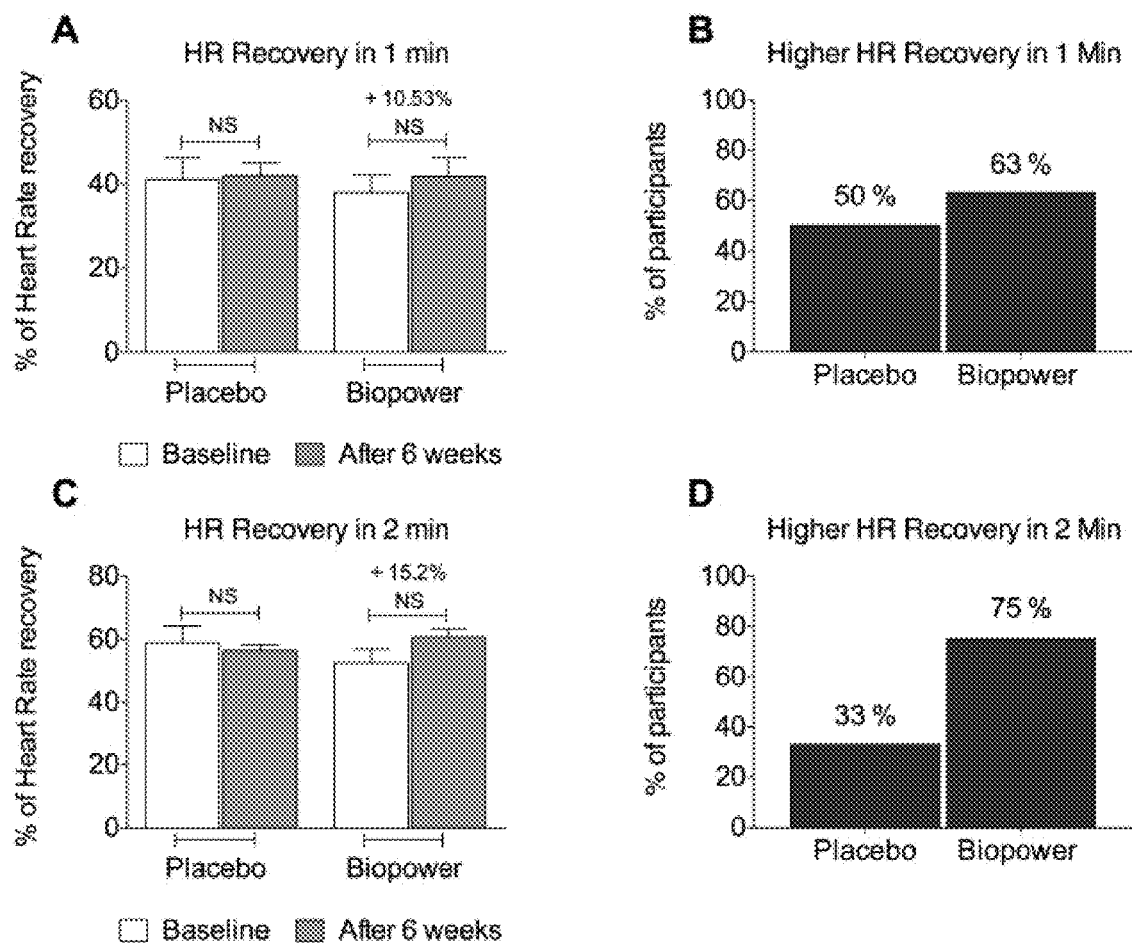
FIG. 46 illustrate the heart rate recovery of young baseball players exercising with bioceramic t-shirts or sham t-shirts.

FIG. 46 illustrates the results of the heart hate recovery 1 minute after evaluation of young baseball players: PANEL A illustrates the heart rate recovery 1 minute after evaluation and PANEL B illustrates the percentage of participants with higher recovery percentage PANEL C illustrates the heart rate recovery 2 minutes after evaluation and PANEL D illustrates the percentage of participants with higher recovery percentage. Each column represents the mean of 12-15 participants, and the vertical lines indicate the S.E.M. NS stands for not statistically significant (T-Test 95% confidence interval—Graphpad Prism software, USA, 2014).

Figure 47A:
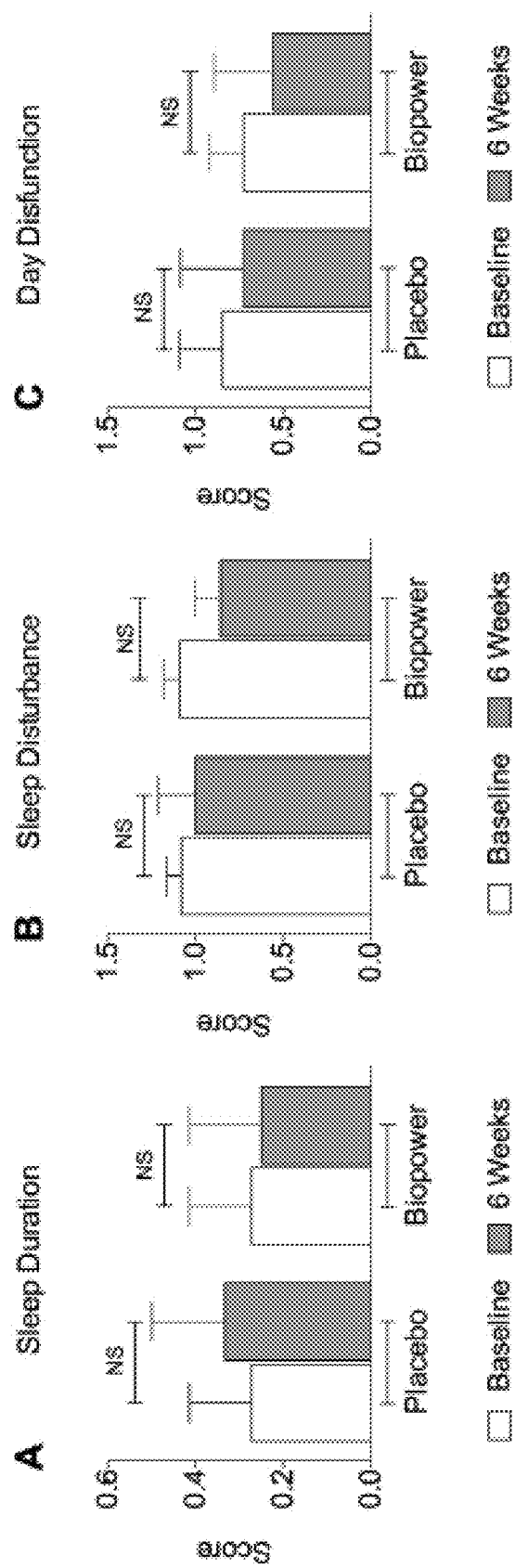
FIG. 47A illustrate the results of far-infrared emitting bioceramic apparel on sleep duration (Panel A), sleep disturbance (Panel B), and day disfunction (Panel C) of young baseball players.
Figure 47B:
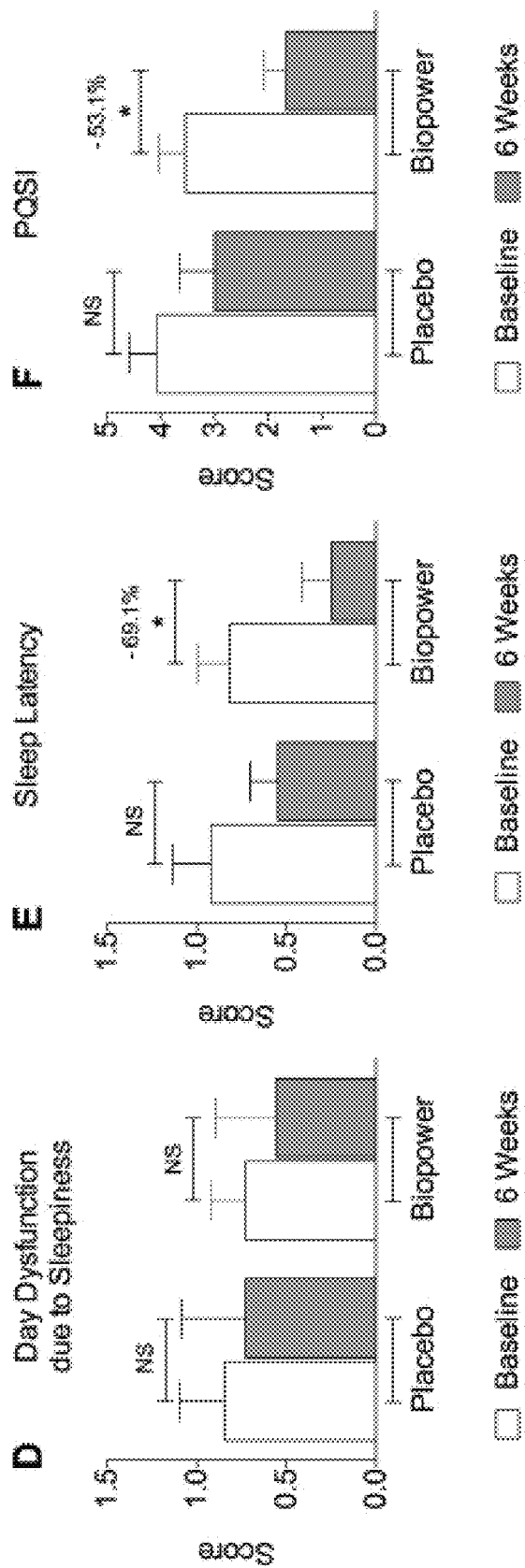
FIG. 47B illustrate the results of far-infrared emitting bioceramic apparel on day dysfunction due to sleepiness (Panel A), sleep latency (Panel B), and PQSI (Panel C) of young baseball players.

FIGS. 47A and 47B illustrate the results of the Pittsburgh Quality of Sleep Questionnaire. Each column represents the mean of 12-15 participants, and the vertical lines indicate the S.E.M. *p<0.05 when comparing with baseline evaluation (paired T-Test 95% confidence interval—Graphpad Prism software, USA, 2014). The overall results shown in FIGS. 47A and 47B suggest that the use of Biopower far-infrared emitting ceramic shirts statistically decreased the following indexes (a lower index is indicative of a more beneficial result). FIG. 47B PANEL E sleep latency: Minimum Score=0 (better); Maximum Score=3 (worse); and FIG. 47B PANEL F The Pittsburgh Quality of Sleep Questionnaire: Minimum Score=0 (better); Maximum Score=21 (worse). The differences between the bioceramics and the control groups for FIG. 47A PANELS A-C (sleep duration, sleep disturbance, day dysfunction) and FIG. 47B PANEL A (day dysfunction due to sleepiness) were not statistically significant.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparel that comprises a coat of a bioceramic, the coat consisting of
    a) about 40 wt % to about 60 wt % kaolinite ($Al_2Si_2O_5(OH)_4$);
    b) about 5 wt % to about 15 wt % tourmaline;
    c) about 15 wt % to about 25 wt % aluminum oxide ($Al_2O_3$);
    d) about 10 wt % to about 20 wt % silicon dioxide ($SiO_2$); and
    e) one other oxide provided that the amounts are by total weight of the bioceramic, and wherein when heated or exposed to heat, the bioceramic provides a biomodulatory or physiological effect when the apparel is applied to a subject.

2. The apparel of claim 1, provided that the biomodulatory or physiological effect comprises: a reduction of pain, an increase in muscle endurance, a modulation of the cardio-respiratory system, a modulation of cellular metabolism, analgesia, an anti-oxidative effect, an anti-fibromyalgia effect, a decrease in inflammation, a decrease in oxidative stress, a modulation of cytokine levels, a modulation of blood circulation, a reduction in intolerance to a cold environment, a reduction in a symptom of arthritis or vascular disease, an increase in cutaneous perfusion, a decrease in heart rate, a decrease in blood pressure, an esthetic effect, or a reduction in cellulite of the subject.

3. The apparel of claim 1, provided that the bioceramic emits, transmits, or reflects an infrared wavelength when heated or exposed to heat.

4. The apparel of claim 3, provided that the infrared wavelength is far infrared that comprises a wavelength from about 1 micrometer to about 1 millimeter.

5. The apparel of claim 3, provided that the infrared wavelength is from about 3 micrometers to about 15 micrometers.

6. The apparel of claim 1, provided that the reflectance of a far infrared energy by the bioceramic at a room temperature of 25° C. is at least 80% of a far infrared range between about 7 micrometers and about 12 micrometers.

7. The apparel of claim 1, provided that the apparel is selected from the group consisting of patches, pads, insoles, body supports, headwear, and combinations thereof.

8. The apparel of claim 1, provided that the apparel comprises a shirt, a jacket, shorts, or trousers.

9. The apparel of claim 1, provided that the apparel comprises a wrist band, a pad, a knee brace, an ankle brace, a sleeve, or a patch.

10. The apparel of claim 1, provided that the kaolinite ranges from 45 wt % to 55 wt %.

11. The apparel of claim 1, provided that the tourmaline comprises $NaFe^{2+}_3Al_6Si_6O_{18}(BO_3)_3(OH)_3OH$.

12. The apparel of claim 1, provided that the largest dimension of any particle in the bioceramic is from about 0.1 micrometers to about 250 micrometers.

13. The apparel of claim 1, provided that the biomodulatory or physiological effect comprises a change that is statistically significant.

14. The apparel of claim 2, provided that the pain is caused by a physical activity.

15. An apparel that comprises a coat of a bioceramic, the coat consisting of
    a. 40 wt % to 60 wt % kaolinite ($Al_2Si_2O_5(OH)_4$);
    b. 5 wt % to 15 wt % tourmaline;
    c. 15 wt % to 25 wt % aluminum oxide ($Al_2O_3$);
    d. 10 wt % to 20 wt % silicon dioxide ($SiO_2$);

provided that the amounts are by total weight of the bioceramic, and wherein when heated or exposed to heat, the bioceramic provides a biomodulatory or physiological effect when the article is applied to a subject.

\* \* \* \* \*